United States Patent
Leavitt et al.

(10) Patent No.: US 9,994,518 B2
(45) Date of Patent: Jun. 12, 2018

(54) ALPHA-7 NICOTINIC ACETYLCHOLINE RECEPTOR MODULATORS AND USES THEREOF

(71) Applicant: MERCK SHARP & DOHME CORP., Rahway, NJ (US)

(72) Inventors: Kenneth Leavitt, Mount Laurel, NJ (US); Brendan Crowley, Collegeville, PA (US); Ian M. Bell, Harleysville, PA (US); Andrew Harvey, Thebarton (AU); Thomas Avery, Thebarton (AU); Dharam Paul, Thebarton (AU); Justin Ripper, Thebarton (AU); Belinda Huff, Thebarton (AU); Rajinder Singh, Thebarton (AU); Laurent Schaeffer, Illkirch (FR); Christophe Joseph, Illkirch (FR); Christophe Morice, Illkirch (FR); Bruno Giethlen, Illkirch (FR); Patrick Bazzini, Illkirch (FR); Aurelie Fromeyer, Illkirch (FR)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days. days.

(21) Appl. No.: 15/318,207

(22) PCT Filed: Jun. 11, 2015

(86) PCT No.: PCT/US2015/035232
§ 371 (c)(1),
(2) Date: Dec. 12, 2016

(87) PCT Pub. No.: WO2015/191799
PCT Pub. Date: Dec. 17, 2015

(65) Prior Publication Data
US 2017/0152221 A1 Jun. 1, 2017

(30) Foreign Application Priority Data
Jun. 13, 2014 (AU) ................. 2014902265

(51) Int. Cl.
*C07D 239/34* (2006.01)
*C07C 311/29* (2006.01)
*C07C 311/08* (2006.01)
*C07D 213/69* (2006.01)
*C07C 307/10* (2006.01)
(Continued)

(52) U.S. Cl.
CPC ............ *C07C 311/29* (2013.01); *A61K 31/18* (2013.01); *C07C 307/10* (2013.01); *C07C 311/08* (2013.01); *C07C 323/67* (2013.01); *C07D 213/64* (2013.01); *C07D 213/69* (2013.01); *C07D 239/34* (2013.01)

(58) Field of Classification Search
CPC ... C07C 307/10; C07C 311/08; C07C 311/29; C07C 323/67; C07D 213/64; C07D 213/65; C07D 213/69; C07D 239/34; A61K 31/18

USPC ............. 544/298; 546/296, 300; 564/84; 514/269, 348, 351, 602
See application file for complete search history.

(56) References Cited

U.S. PATENT DOCUMENTS

| 2004/0167188 A1 | 8/2004 | Xin et al. |
| 2004/0214870 A1* | 10/2004 | Xin .................. C07D 261/18 514/362 |
| 2010/0041763 A1 | 2/2010 | Elworthy |

FOREIGN PATENT DOCUMENTS

| WO | WO2012103583 | 8/2012 |
| WO | WO2014019023 | 2/2014 |

(Continued)

OTHER PUBLICATIONS

Damaj et al., Medline Abstract (Psychopharmacologia, vol. 120, Issue 4, pp. 483-490) Aug. 1995.*

(Continued)

*Primary Examiner* — Deepak R Rao
(74) *Attorney, Agent, or Firm* — Matthew A. Leff; Gloria M. Fuentes

(57) ABSTRACT

Disclosed are compounds of Formula (IVA), or a salt thereof, and pharmaceutical formulations (pharmaceutical compositions) comprising those compounds, or a salt thereof: Formula (IVA), wherein "$R^{Ia}$", "$R^{Ib}$", "$R^{Ic}$", "$R^{Id}$", "$R^{Ie}$", are defined herein above, which compounds are believed suitable for use in positive modulation of the alpha 7 nicotinic acetylcholine receptor (α7 nAChR) receptors, for example, those found in the cerebral cortex and the hippocampus. Such compounds and pharmaceutical formulations are believed to be useful in treatment or management of neurodegenerative diseases, for example, Alzheimer's disease (AD), schizophrenia, and Parkinson's disease (PD), or movement disorders arising from use of certain medications used in the treatment or management of Parkinson's disease.

(IV A)

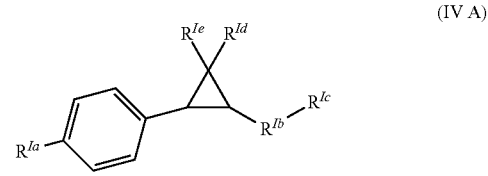

7 Claims, No Drawings

(51) Int. Cl.
    *C07C 323/67*     (2006.01)
    *C07D 213/64*     (2006.01)
    *A61K 31/18*     (2006.01)

(56) References Cited

FOREIGN PATENT DOCUMENTS

| WO | WO2014172759 | | 10/2014 |
|----|--------------|---|---------|
| WO | WO 2015/042243 | * | 3/2015 |
| WO | WO 2015/119899 | * | 8/2015 |

OTHER PUBLICATIONS

Layzer, Degenerative Diseases of the Nervous System, Cecil Textbook of Medicine, 20th Edition, vol. 2, pp. 2050-2057, 1996.*

Damasio, Alzheimer's Disease and related dementias, Cecil Textbook of Medicine, 20th Edition, vol. 2, pp. 1992-1996, 1996.*

Mirza et al., PubMed Abstract (Psychopharmacology (Berl). 148(3):243-50), Feb. 2000.*

Terry et al., PubMed Abstract (Neuroscience, 101 (2):357-68), 2000.*

Court et al., PubMed Abstract (J Chem Neuroanat. 20(3-4):281-98), Dec. 2000.*

Kozikowski et al., Structural Remodeling of Cocaine: Design and Synthesis of Trisubstituted Cyclopropanes as Selective Serotonin Reuptake Inhibitors, ChemMedChem, 1, pp. 58-65, 2006.*

Dey, Journal of Biomolecular Structure, in Search of Allosteric Modulators of Alpha 7, 2011, 695-715, 29(6).

Kozikowski et al, Structural Remodeling of Cocaine: Design and Synthesis of Trisubstituted Cyclopropanes as Selective Serotonin Reuptake Inhibitors, Chemmedchem, 2006, 58-65, 1.

* cited by examiner

ALPHA-7 NICOTINIC ACETYLCHOLINE RECEPTOR MODULATORS AND USES THEREOF

FIELD

The present invention relates to chemical compounds useful in the positive modulation of the alpha 7 nicotinic acetylcholine receptor (α7 nAChR). The invention also relates to the use of these compounds in the treatment or prevention of a broad range of diseases in which the positive modulation of α7 nAChR is advantageous, including neurodegenerative and neuropsychiatric diseases and also neuropathic pain and inflammatory diseases.

BACKGROUND

The α7 nAChRs are rapidly desensitizing ligand-gated ion channels that are abundantly expressed in the cerebral cortex and the hippocampus, a limbic structure intimately linked to attention processing and memory formation, see for example, Seguela et al. J. Neuroscience 1993 (13) pp 596-604. α7 nAChRs modulate neurotransmitter release and are responsible for direct fast excitatory neurotransmission. At the cellular level, activation of α7 nAChRs can regulate interneuron excitability, modulate the release of excitatory and inhibitory neurotransmitters, and contribute to neuroprotective effects.

Several lines of evidence indicate that impaired attention and cognition, which are characteristic of neurological and psychiatric disorders such as Alzheimer's disease (AD), see for example, Kem, Behav. Brain Res. 2000 (13) pp 169-81), schizophrenia, Parkinson's disease (PD), multiple sclerosis, attention deficit hyperactivity disorder (ADHD), mild cognitive impairment (MCI), age associated memory impairment (AAMI), may involve degeneration or hypo-function of cholinergic input, see for example, Rezvani and Levin Biological Psychiatry 2001 (49) pp 258-267. Moreover, genetic linkage has identified α7 nAChRs as a predisposing factor related to sensory gating deficits, see for example, (Freedman et al., Proceed. Nat. Acad. Sci. USA, 1997 (94) pp 587-92. Thus, targeting the α7 nAChRs represents a therapeutic strategy for ameliorating cognitive deficits associated with neurodegenerative and neuropsychiatric diseases.

A number of reports also suggest that α7 nAChRs mediate protection against neurotoxicity induced by amyloid beta and excitotoxic insults. Peripherally, α7 nAChRs are expressed in macrophages and their stimulation is essential for inhibiting the release of proinflammatory cytokines (e.g. TNF-a, IL-1) via the cholinergic anti-inflammatory pathway which is triggered in response to signals from the vagus nerve, see for example, (Wang, et al., J. of Neurochem. 2000 (75) pp. 1155-1161. Thus, the clinical use of positive modulators of the α7 nAChRs could also represent a strategy against inflammatory diseases.

Selective positive allosteric modulation (PAM) of the α7 nAChR is a recently proposed therapeutic approach for treating these disease states. A key advantage of this approach is that modulation only occurs in the presence of endogenous agonist thereby preserving the temporal and spatial integrity of neurotransmission, see for example, Picciotto, 2003 Trends in Pharm. Sciences, September 24(9), pp 493-499). Several different profiles have been described for PAMs of the α7 nAChR ranging from Type I modulators that predominately affect the peak current and may also increase channel affinity for the agonist, to Type II modulators that affect the peak current, delay the desensitization of the receptor and may reactivate desensitized receptors, see for example, Gronlein et al., Mol Pharmacol 2007 (72) pp. 715-724. Several PAMs have been described in the literature with some Type I examples including: 5-Hydroxyindole (Gurley et al., Soc Neurosci Abs. 2000, 716, p. 15), NS-1738 (Timmerman, et al., J Pharmacol Exp Ther, 2007 (323) pp 294-307), Ivermectin (Krause et al., Mol Pharmacol 1998 (53), pp 283-294), Galantamine (Lopes, et al., J Pharmacol Exp Ther. 2007 (322), pp. 48-58) and Genistein (Charpantier, et al., J Neurosci 2005 (25), pp 9836-9849); Type II examples including PNU-120596 Hurst, et al., 2005 (25), pp 4396-4405), TQS (Gronlien, et al., Mol Pharmacol, 2007 (72), pp 715-724) 2007, and A-867744 (Faghih, et al., J Med Chem 2009, (52), pp. 3377-3384), and some intermediate examples: SB-206553 (Dunlop, et al., J. Pharmacol. Exp Ther., 2009 (328), pp. 766-776) and JNJ-1930942 (Dinklo, et al., J Pharmacol Exp Ther., 2011 (336), pp. 560-574). 2011; 336:560-74). In general, PAMs demonstrate enhanced receptor responses to the endogenous ligands acetylcholine and choline, as well as to nicotine and other agonists.

The present invention seeks to address some of the shortcomings of the prior art compounds and is directed to a new class of compounds which exhibit positive modulation of α7 nAChR.

SUMMARY OF THE INVENTION

In one aspect the invention provides compounds of formula (I) or salts thereof:

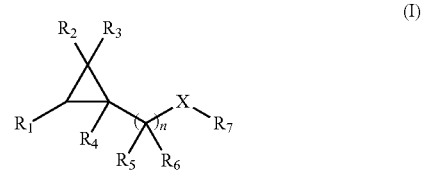

wherein
R$_1$ is selected from aryl which is independently substituted at least one time by a group consisting of cyano, fluoro, nitro, optionally substituted C$_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted C$_{3-7}$ cycloalkyl, optionally substituted C$_{2-10}$ alkoxy, —P=O(OH)NH$_2$, —C(O)R, —C(O)OR, —OC(O)R (where each R is independently selected from hydrogen, optionally substituted C$_{2-10}$ alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R''', —NR'S(O)$_2$R", —S(O)$_2$—NR'R" and NR'R" (where each R" and R''' are independently selected from hydrogen, optionally substituted C$_{1-4}$ alkyl, optionally substituted C$_{3-7}$ cycloalkyl or optionally substituted heterocyclyl, or R' and R" or R' and R''' or R" and R''' together form optionally substituted heterocyclyl), or —S(O)R"" and —S(O)$_2$R"" (where R"" is optionally substituted C$_{1-4}$ alkyl, or C$_{3-7}$ cycloalkyl);

R₂ and R₃ are independently selected from hydrogen, F, CN, C₁-C₄ alkyl, C₃₋₉ cycloalkyl, C₃₋₉ heterocyclyl, phenyl or C₁-C₄ haloalkyl; or R₂ and R₃ together form C₃₋₉ cycloalkyl, C₃₋₉ heterocyclyl or C₄₋₉ cycloalkenyl;

R₄-R₆ are independently selected from hydrogen, halogen or optionally substituted C₁₋₄ alkyl;

n is 1-3;

X is selected from O, S, S(O), S(O)₂ or CR$^A$R$^B$ (wherein R$^A$ and R$^B$ are independently selected from hydrogen or optionally substituted C₁₋₆ alkyl or together form C₄-C₉ cycloalkyl); and R₇ is selected from optionally substituted heteroaryl or optionally substituted aryl.

In an embodiment R₁ is phenyl substituted at least one time with a group as aforementioned described in relation to compounds of formula (I).

Accordingly, in a further aspect the invention provides compounds of formula (Ia) or salts thereof:

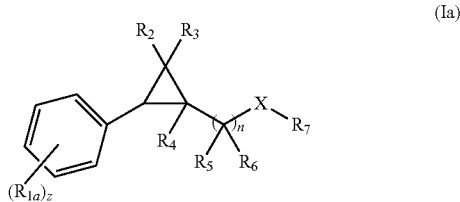

(Ia)

wherein

R$_{1a}$ is selected from the group consisting of cyano, fluoro, nitro, optionally substituted C₁₋₁₀ alkyl, optionally substituted aryl, optionally substituted aryloxy, optionally substituted benzyl, optionally substituted six-membered heteroaryl, five-membered heteroaryl, optionally substituted heterocyclyl, optionally substituted C₃₋₇ cycloalkyl, optionally substituted C₂₋₁₀ alkoxy, —P═O(OH)NH₂, —C(O)R, —C(O)OR, —OC(O)R (where each R is independently selected from hydrogen, optionally substituted C₂₋₁₀ alkyl, optionally substituted alkenyl, optionally substituted alkynyl, optionally substituted C₃₋₇ cycloalkyl, optionally substituted heterocyclyl, optionally substituted heteroaryl, and optionally substituted aryl), —C(O)NR'R", —NR'C(O)R", —NR'S(O)₂—NR"R'", —NR'S(O)₂R", —S(O)₂—NR'R" and NR'R" (where each R', R" and R'" are independently selected from hydrogen, optionally substituted C₁₋₄ alkyl, optionally substituted C₃₋₇ cycloalkyl or optionally substituted heterocyclyl, or R' and R" or R' and R'" or R" and R'" together form heterocyclyl), or —S(O)R"" and —S(O)₂R"" (where R"" is optionally substituted C₁₋₄ alkyl, or C₃₋₇ cycloalkyl);

z is 1-4;

R₂ and R₃ are independently selected from hydrogen, F, CN, C₁-C₄ alkyl, C₃₋₉ cycloalkyl, C₃₋₉ heterocyclyl, phenyl or C₁-C₄ haloalkyl; or R₂ and R₃ together form C₃-C₉ cycloalkyl, C₃₋₉ heterocyclyl or C₄-C₉ cycloalkenyl;

R₄-R₆ are independently selected from hydrogen, halogen or optionally substituted C₁₋₄ alkyl;

n is 1-3;

X is selected from O, S S(O), S(O)₂ or CR$^A$R$^B$ (wherein R$^A$ and R$^B$ are independently selected from hydrogen or optionally substituted C₁₋₆ alkyl or together form C₄-C₉ cycloalkyl); and R₇ is selected from optionally substituted heteroaryl or optionally substituted aryl.

In some embodiments, z is 4. In some embodiments, z is 3.

In some embodiments, z is In some embodiments, z is 1. In some embodiments in which z is 1, R1a is in the para position.

In an embodiment, R$_{1a}$ is independently selected from the group consisting of —C(O)NR'R", —NR'C(O)R", —NR'S(O)₂—NR"R'", —NR'S(O)₂R", —S(O)₂—NR'R" and NR'R" (where each R', R" and R'" are independently selected from hydrogen, optionally substituted C₁₋₄ alkyl, optionally substituted C₃₋₇ cycloalkyl or optionally substituted heterocyclyl, or R' and R" or R' and R'" or R" and R'" together form heterocyclyl), —S(O)R"" and —S(O)₂R"" (where R"" is optionally substituted C₁₋₄ alkyl, or C₃₋₇ cycloalkyl).

In another embodiment R₂ is hydrogen or C₁-C₃ alkyl and R₃ is hydrogen or C₁-C₃ alkyl.

Accordingly, in a further aspect the invention provides compounds of formula (Ib) or salts thereof:

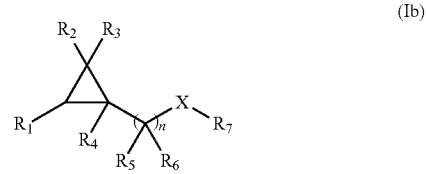

(Ib)

wherein

R₁ is selected from aryl which is independently substituted at least one time by a group consisting of cyano, fluoro, nitro, optionally substituted C₁₋₁₀ alkyl, optionally substituted aryl, optionally substituted aryloxy, optionally substituted benzyl, optionally substituted six-membered heteroaryl, five-membered heteroaryl, optionally substituted heterocyclyl, optionally substituted C₃₋₇ cycloalkyl, optionally substituted C₂₋₁₀ alkoxy, —P═O(OH)NH₂, —C(O)R, —C(O)OR, —OC(O)R (where each R is independently selected from hydrogen, optionally substituted C₂₋₁₀ alkyl, optionally substituted alkenyl, optionally substituted alkynyl, optionally substituted C₃₋₇ cycloalkyl, optionally substituted heterocyclyl, optionally substituted heteroaryl, and optionally substituted aryl), —C(O)NR'R", —NR'C(O)R", —NR'S(O)₂—NR"R'", —NR'S(O)₂R", —S(O)₂—NR'R" and NR'R" (where each R', R" and R'" are independently selected from hydrogen, optionally substituted C₁₋₄ alkyl, optionally substituted C₃₋₇ cycloalkyl or optionally substituted heterocyclyl, or R' and R" or R' and R'" or R" and R'" together form optionally substituted heterocyclyl), or —S(O)R"" and —S(O)₂R"" (where R"" is optionally substituted C₁₋₄ alkyl, or C₃₋₇ cycloalkyl);

R₂ and R₃ is selected from hydrogen, F, CN, C₁-C₄ alkyl, C₃₋₉ cycloalkyl, C₃₋₉ heterocyclyl, phenyl or C₁-C₄ haloalkyl;

R₂ and R₃ are independently selected from hydrogen or C₁-C₃ alkyl;

R₄-R₆ are independently selected from hydrogen, halogen or optionally substituted C₁₋₄ alkyl;

n is 1-3;

X is O, S S(O), S(O)₂ or CR$^A$R$^B$ (wherein R$^A$ and R$^B$ are independently selected from hydrogen or optionally substituted C₁₋₆ alkyl or together form C₄-C₉ cycloalkyl); and $R_7$ is selected from optionally substituted heteroaryl or optionally substituted aryl.

In an embodiment, $R_1$ in (Ib) is a phenyl group substituted with $R_{1a}$ wherein $R_{1a}$ is selected from cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form heterocyclyl), or —S(O)R"" and —S(O)$_2$R"" (where R"" is optionally substituted $C_{1-4}$ alkyl, or $C_{3-7}$ cycloalkyl).

In an embodiment and with reference to formulae (I), (Ia) and (Ib), $R_4$-$R_6$ are independently selected from hydrogen, halogen or $C_{1-4}$ alkyl.

In an embodiment and with reference to formulae (I), (Ia) and (Ib), $R_4$-$R_6$ are independently selected from hydrogen or $C_{1-2}$ alkyl.

In an embodiment and with reference to formulae (I), (Ia) and (Ib), $R_4$-$R_6$ are all hydrogen.

Accordingly, in a further aspect the invention provides compounds of formula (Ic) or salts thereof:

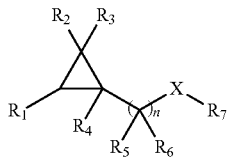

(Ic)

wherein
$R_1$ is selected from aryl which is independently substituted at least one time by a group consisting of cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form optionally substituted heterocyclyl), or —S(O)R"" and —S(O)$_2$R"" (where R"" is optionally substituted $C_{1-4}$ alkyl, or $C_{3-7}$ cycloalkyl);

$R_2$ and $R_3$ is selected from hydrogen, F, CN, $C_1$-$C_4$ alkyl, $C_{3-9}$ cycloalkyl, $C_{3-9}$ heterocyclyl, phenyl or $C_1$-$C_4$ haloalkyl; or $R_2$ and $R_3$ together form $C_{3-9}$ cycloalkyl, $C_{3-9}$ heterocyclyl or $C_{4-9}$ cycloalkenyl;

$R_4$-$R_6$ are all hydrogen;

n is 1-3;

X is selected from O, S, S(O), S(O)$_2$ or CR$^A$R$^B$ (wherein R$^A$ and R$^B$ are independently selected from hydrogen or optionally substituted $C_{1-6}$ alkyl or together form $C_4$-$C_9$ cycloalkyl); and $R_7$ is selected from optionally substituted heteroaryl or optionally substituted aryl.

In an embodiment, $R_1$ in (Ic) is a phenyl group substituted with $R_{1a}$ wherein $R_{1a}$ is selected from cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form heterocyclyl), or —S(O)R"" and —S(O)$_2$R"" (where R"" is optionally substituted $C_{1-4}$ alkyl, or $C_{3-7}$ cycloalkyl).

In some embodiments, with reference to formulae (I), (Ia), (Ib) and (Ic), X is selected from O, S, S(O) or S(O)$_2$. In some embodiments, and with reference to formulae (I), (Ia), (Ib) and (Ic), X is selected from O, S and S(O). In some embodiments, and with reference to formulae (I), (Ia), (Ib) and (Ic), X is selected from O and S. In some embodiments, and with reference to formulae (I), (Ia), (Ib) and (Ic), X is O.

Accordingly, in a further aspect the invention provides compounds of formula (Id) or salts thereof:

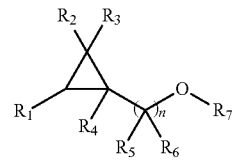

(Id)

wherein
$R_1$ is selected from aryl which is independently substituted at least one time by a group consisting of cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and —NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form optionally substituted heterocyclyl), or —S(O)R"" and —S(O)$_2$R"" (where R"" is optionally substituted $C_{1-4}$ alkyl, or $C_{3-7}$ cycloalkyl);

$R_2$ and $R_3$ is selected from hydrogen, F, CN, $C_1$-$C_4$ alkyl, $C_{3-9}$ cycloalkyl, $C_{3-9}$ heterocyclyl, phenyl or $C_1$-$C_4$ haloalkyl; or $R_2$ and $R_3$ together form $C_{3-9}$ cycloalkyl, $C_{3-9}$ heterocyclyl or $C_{4-9}$ cycloalkenyl;

$R_4$-$R_6$ are independently selected from hydrogen, halogen or optionally substituted $C_{1-4}$ alkyl;

n is 1-3; and $R_7$ is selected from optionally substituted heteroaryl or optionally substituted aryl.

In an embodiment, $R_1$ in (Id) is a phenyl group substituted with $R_{1a}$ wherein $R_{1a}$ is selected from cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form heterocyclyl), or —S(O)R"" and —S(O)$_2$R"" (where R"" is optionally substituted $C_{1-4}$ alkyl, or $C_{3-7}$ cycloalkyl).

In an embodiment, $R_7$ is selected from either:

(i) aryl which is independently substituted at least one time by a group consisting of cyano, halo, nitro, optionally substituted $C_{1-10}$ alkyl, optionally substituted $C_{1-10}$ haloalkyl, optionally substituted $C_{1-10}$ alkoxy, optionally substituted aryl, optionally substituted aryloxy, optionally substituted benzyl, optionally substituted heteroaryl, optionally substituted heterocyclyl, optionally substituted $C_{4-7}$ cycloalkyl, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form heterocyclyl), —S(O)R"" and —S(O)$_2$R"" (where R"" is optionally substituted $C_{1-4}$ alkyl, or $C_{3-7}$ cycloalkyl); or (ii) optionally substituted heteroaryl.

Accordingly, in a further aspect the invention provides compounds of formula (Ie) or salts thereof:

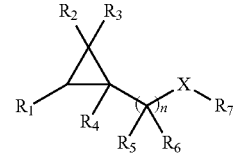

(Ie)

wherein $R_1$ is selected from aryl which is independently substituted at least one time by a group consisting of cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form optionally substituted heterocyclyl), or —S(O)R"" and —S(O)$_2$R"" (where R"" is optionally substituted $C_{1-4}$ alkyl, or $C_{3-7}$ cycloalkyl);

$R_2$ and $R_3$ are independently selected from hydrogen, F, CN, $C_1$-$C_4$ alkyl, $C_{3-9}$ cycloalkyl, $C_{3-9}$ heterocyclyl, phenyl or $C_1$-$C_4$ haloalkyl; or $R_2$ and $R_3$ together form $C_{3-9}$ cycloalkyl or $C_{4-9}$ cycloalkenyl;

$R_4$-$R_6$ are independently selected from hydrogen, halogen or optionally substituted $C_{1-4}$ alkyl;

n is 1-3;

X is selected from O, S, S(O), S(O)$_2$ or $CR^AR^B$ (wherein $R^A$ and $R^B$ are independently selected from hydrogen or optionally substituted $C_{1-6}$ alkyl or together form $C_4$-$C_9$ cycloalkyl); and $R_7$ is selected from either (i) aryl which is independently substituted at least one time by a group consisting of cyano, halo, nitro, optionally substituted $C_{1-10}$ alkyl, optionally substituted $C_{1-10}$ haloalkyl, optionally substituted $C_{1-10}$ alkoxy, optionally substituted aryl, optionally substituted aryloxy, optionally substituted benzyl, optionally substituted heteroaryl, optionally substituted heterocyclyl, optionally substituted $C_{4-7}$ cycloalkyl, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R''', —NR'S(O)$_2$R", —S(O)$_2$—NR'R" and NR'R" (where each R', R" and R''' are independently selected from hydrogen, optionally substituted $C_{1-4}$ alkyl, optionally substituted $C_{3-7}$ cycloalkyl or optionally substituted heterocyclyl or R' and R" or R' and R''' or R" and R''' together form heterocyclyl), —S(O)R"" and —S(O)$_2$R"" (where R"" is optionally substituted $C_{1-4}$ alkyl, or $C_{3-7}$ cycloalkyl); or (ii) optionally substituted heteroaryl.

In a further aspect, the invention provides compounds of formula (II) or salts thereof:

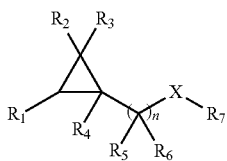

(II)

wherein $R_1$ is substituted aryl;

$R_2$ and $R_3$ are independently selected from hydrogen, F, CN, $C_1$-$C_4$ alkyl, $C_{3-9}$ cycloalkyl, $C_{3-9}$ heterocyclyl, phenyl or $C_1$-$C_4$ haloalkyl; or $R_2$ and $R_3$ together form $C_{3-9}$ cycloalkyl, $C_{3-9}$ heterocyclyl or $C_{4-9}$ cycloalkenyl;

$R_4$-$R_6$ are independently selected from hydrogen, halogen or optionally substituted $C_{1-4}$ alkyl;

n is 1-3;

X is selected from O, S, S(O), S(O)$_2$ or $CR^A R^B$ (wherein $R^A$ and $R^B$ are independently selected from hydrogen or optionally substituted $C_{1-6}$ alkyl or together form a $C_4$-$C_9$ cycloalkyl);

$R_7$ is selected from either (i) aryl which is independently substituted at least one time by a group consisting of cyano, halo, nitro, optionally substituted $C_{1-10}$ alkyl, optionally substituted $C_{1-10}$ haloalkyl, optionally substituted $C_{2-10}$ alkoxy, optionally substituted aryl, optionally substituted aryloxy, optionally substituted benzyl, optionally substituted heteroaryl, optionally substituted heterocyclyl, optionally substituted $C_{4-7}$ cycloalkyl, —P=O(OH)NH$_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R''', —NR'S(O)$_2$R", —S(O)$_2$—NR'R" and NR'R" (where each R', R" and R''' are independently selected from hydrogen, optionally substituted $C_{1-4}$ alkyl, optionally substituted $C_{3-7}$ cycloalkyl or optionally substituted heterocyclyl or R' and R" or R' and R''' or R" and R''' together form heterocyclyl), —S(O)R"" and —S(O)$_2$R"" (where R"" is optionally substituted $C_{1-4}$ alkyl, or $C_{3-7}$ cycloalkyl); or (ii) optionally substituted heteroaryl;

whereby the following compounds are excluded:

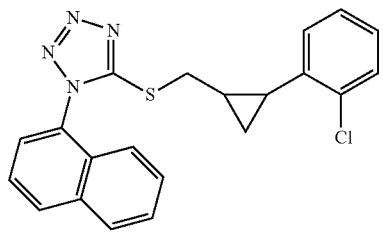

(a)

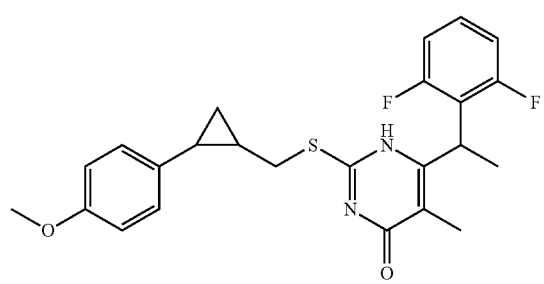

(b)

In still a further aspect the invention provides compounds of formula (III) or salts thereof:

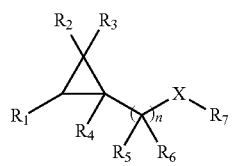

(III)

wherein $R_1$ is substituted aryl;

$R_2$ and $R_3$ are independently selected from hydrogen, F, CN, $C_1$-$C_4$ alkyl, $C_{3-9}$ cycloalkyl, $C_{3-9}$ heterocyclyl, phenyl or $C_1$-$C_4$ haloalkyl; or $R_2$ and $R_3$ together form $C_{3-9}$ cycloalkyl, $C_{3-9}$ heterocyclyl or $C_{4-9}$ cycloalkenyl;

$R_4$-$R_6$ are independently selected from hydrogen, halogen or optionally substituted $C_{1-4}$ alkyl;

n is 1-3;

X is selected from O, S, S(O), S(O)$_2$ or $CR^A R^B$ (wherein $R^A$ and $R^B$ are independently selected from hydrogen or optionally substituted $C_{1-6}$ alkyl or together form a $C_4$-$C_9$ cycloalkyl); and $R_7$ is selected from optionally substituted heteroaryl or optionally substituted aryl;

whereby the following compounds are excluded:

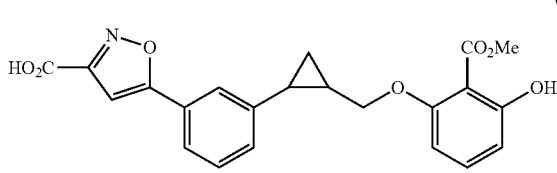

(i)

-continued (ii)
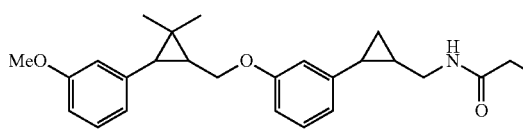

(iii)
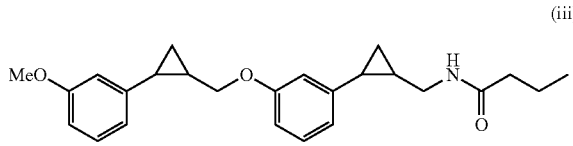

(iv)
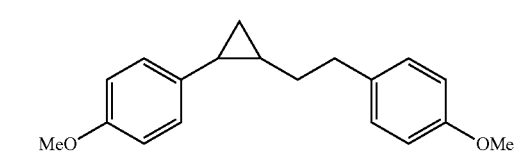

(v)
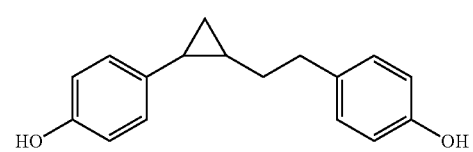

(vi)
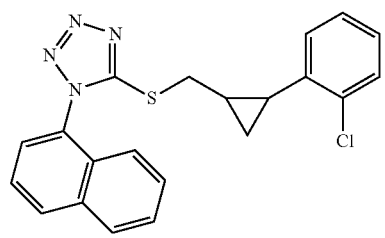

(vii)
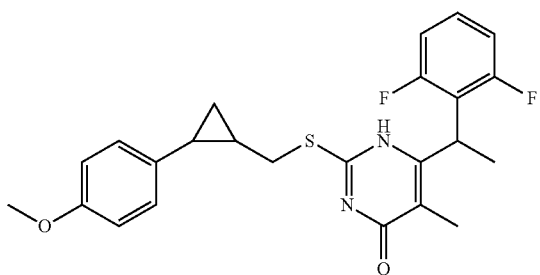

In a further aspect, the invention provides a method for the treatment or prevention of cognitive deficits associated with neurodegeneration or neuropsychiatric diseases, said method including the step of administering a compound of formula (I), (Ia), (Ib), (Ic), (Id), (Ie), (II) or (III), or a pharmaceutically acceptable salt thereof, or a composition comprising a compound of formula (I), (Ia), (Ib), (Ic), (Id), (Ie), (II) or (III), and related formulae as herein defined or a pharmaceutically acceptable salt thereof.

In still a further aspect, the invention provides a method for the treatment or prevention of inflammatory diseases, said method including the step of administering a compound of formula (I), (Ia), (Ib), (Ic), (Id), (Ie), (II) or (III), and related formulae as herein defined or a pharmaceutically acceptable salt thereof, or a composition comprising a compound of formula (I), (Ia), (Ib), (Ic), (Id), (Ie), (II) or (III), and related formulae as herein defined or a pharmaceutically acceptable salt thereof.

In still a further aspect the invention provides a method for the treatment or prevention of neuropathic pain, said method including the step of administering a compound of formula (I), (Ia), (Ib), (Ic), (Id), (Ie), (II) or (III), and related formulae as herein defined or a pharmaceutically acceptable salt thereof, or a composition comprising a compound of formula (I), (Ia), (Ib), (Ic), (Id), (Ie), (II) or (III), and related formulae as herein defined or a pharmaceutically acceptable salt thereof.

In another aspect the invention provides the use of a compound of formula (I), (Ia), (Ib), (Ic), (Id), (Ie), (II) or (III), and related formulae as herein defined or a salt thereof in the manufacture of a medicament for the treatment or prevention of cognitive deficits associated with neurodegeneration or neuropsychiatric diseases.

In another aspect the invention provides the use of a compound of formula (I), (Ia), (Ib), (Ic), (Id), (Ie), (II) or (III), and related formulae as herein defined or a salt thereof in the manufacture of a medicament for the treatment or prevention of inflammatory diseases.

In another aspect the invention provides the use of a compound of formula (I), (Ia), (Ib), (Ic), (Id), (Ie), (II) or (III), and related formulae as herein defined or a salt thereof in the manufacture of a medicament for the treatment or prevention of neuropathic pain.

In another aspect of the invention there is provided a method of positively modulating α7 nAChRs in a cell by contacting the cell with a compound of formula (I), (Ia), (Ib), (Ic), (Id), (Ie), (II) or (III), and related formulae as herein defined or a pharmaceutically acceptable salt thereof, to said cell.

In a further aspect of the invention there is provided a pharmaceutical composition for use as a neuroprotective agent, the composition comprising an effective amount of a compound of formula (I), (Ia), (Ib), (Ic), (Id), (Ie), (II) or (III), and related formulae as herein defined or a pharmaceutically acceptable salt thereof and optionally a carrier or diluent.

In still a further aspect of the invention there is provided a pharmaceutical composition for use as an anti-inflammatory agent, the composition comprising an effective amount of a compound of formula (I), (Ia), (Ib), (Ic), (Id), (Ie), (II) or (III), and related formulae as herein defined or a pharmaceutically acceptable salt thereof and optionally a carrier or diluent.

I In still a further aspect of the invention there is provided a pharmaceutical composition for treating neuropathic pain, the composition comprising an effective amount of a compound of formula (I), (Ia), (Ib), (Ic), (Id), (Ie), (II) or (III), and related formulae as herein defined or a pharmaceutically acceptable salt thereof and optionally a carrier or diluent.

In another aspect of the invention there is provided a process for the preparation of compounds of formula (I), (Ia), (Ib), (Ic), (Id), (Ie), (II) or (III), and related formulae as herein defined or salts thereof.

In some embodiments, a compound of the invention is preferably a compound of Formula IVA:

Formula IV A
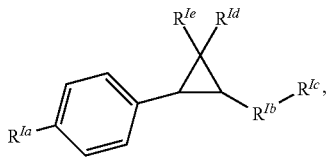

or a pharmaceutically acceptable salt thereof, wherein:

$R^{Ia}$ is a moiety of the formula: (a) $NH_2$—$SO_2$—; (b) $NR'_2$—$SO_2NR''$—, wherein R' is independently for each occurrence: (i) —H; (ii) linear-, branched-, or cyclic-alkyl of up to 6 carbon atoms; or (iii) one of R' is —H and the other is t-BOC; and R'' is: (a) —H; or (b) linear-, branched-, or cyclic-alkyl of up to 6 carbon atoms; or (iv) one of R' is —H and the other R' together with R'' and the —N—$SO_2$—N— moiety to which they are attached form a heterocycle of up to 6 ring atoms;

$R^{Ib}$ has the formula: —$CH_2$—X—, wherein X is —O—, —S—, $CH_2$—;

$R^{Id}$ and $R^{Ie}$ are independently for each occurrence —H or linear-, branched-, or cyclic-alkyl of up to 6 carbon atoms; or $R^{Id}$ and $R^{Ie}$ together with the cyclopropyl moiety to which they are attached from a spirocycl of up to 8 carbon atoms;

$R^{Ic}$ is:

(a) a heteroaryl of the formula:

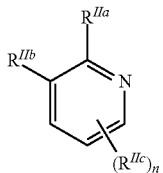

wherein:

n=0, 1, or 2;

one of $R^{IIa}$ or $R^{IIb}$ is a bond to the cyclopropyl core of Formula IVA and the other is —H or —$R^{IIc}$, wherein:

$R^{IIc}$ is: (i) linear-, branched-, or cyclic-alkoxy of up to 6 carbon atoms which may be optionally substituted with one or more halogen; (ii) linear-, branched-, or cyclic-alkyl of up to 6 carbon atoms, which may optionally be substituted with halogen or linear-, branched-, or cyclic-alkoxy of up to 6 carbon atoms;

(b) heteroaryl of the formula

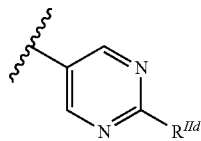

wherein:

$R^{IId}$ is H or linear-, branched-, or cyclic-alkyl of up to 6 carbon atoms; or (c) aryl of the formula

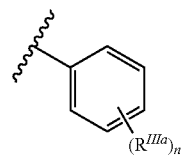

wherein:

n=1 or 2;

$R^{IIIc}$ is: (i) halogen; (ii) —CN; (iii) linear-, branched-, or cyclic-alkoxy of up to 6 carbon atoms which may optionally be substituted with one or more (1) halogen;

or (2) linear-, branched-, or cyclic alkoxy of up to 6 carbon atoms; (iv) linear-, branched-, or cyclic-alkyl of up to 6 carbon atoms which may optionally be substituted with one or more: (1) halogen; or (2) linear-, branched-, or cyclic alkoxy of up to 6 carbon atoms.

In some embodiments, $R^{Ia}$ is preferably $H_2N$—$SO_2$—, $H_2N$—$SO_2$—NH—, or $H_3C$—$SO_2$—NH—.

In some embodiments, $R^{Id}$ and $R^{Ie}$ are preferably —H or methyl. In some embodiments it is preferred for $R^{Id}$ and $R^{Ie}$ to be joined to gether to form, together with the cyclopropyl moiety to which they are attached, a spirocyclo moiety of 7 carbon atoms.

In some embodiments, $R^{Ib}$-$R^{Ic}$ is preferably —$CH_2$—X—$R^{AH}$, wherein:

X is —$CH_2$—, —S—, or —O—; and $R^{AH}$ is:

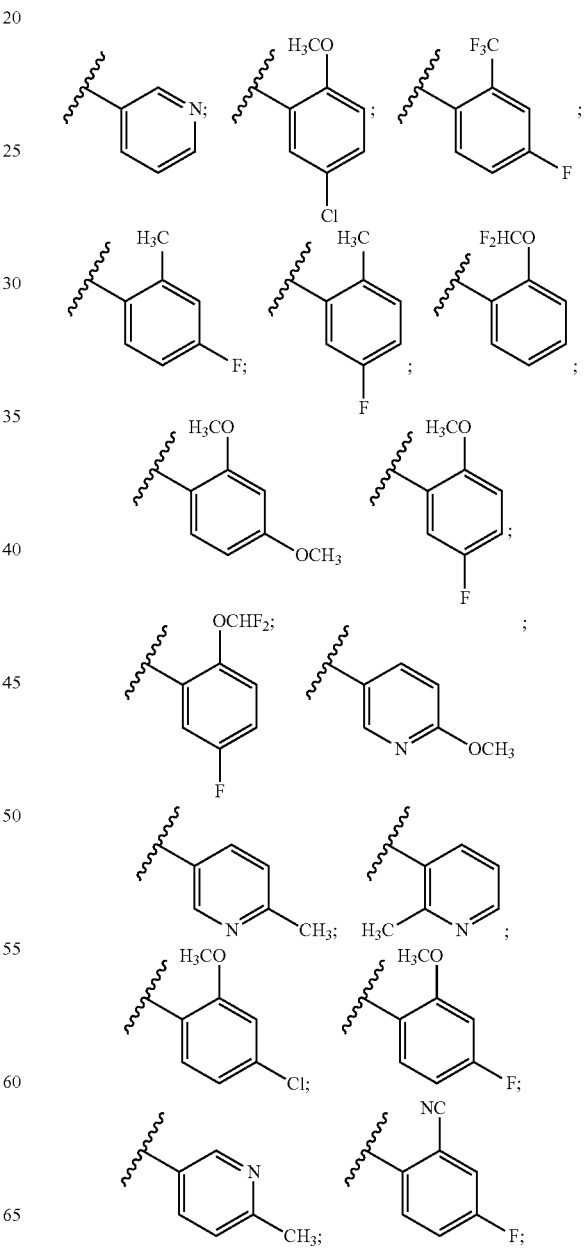

-continued

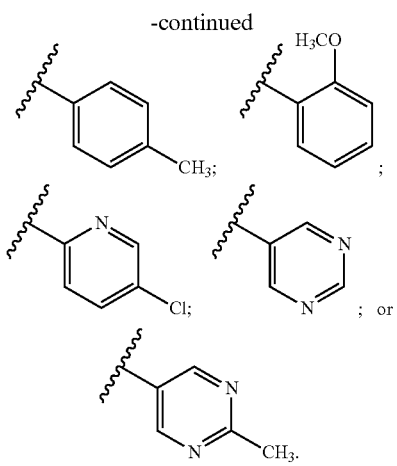

In some embodiments, a compound of the invention is preferably:
±trans 4-{3-[(5-chloro-2-methoxyphenoxy)methyl]-2,2-dimethylcyclopropyl}benzene-sulfonamide;
±trans 4-{2-[(5-chloro-2-methoxyphenoxy)methyl]spiro[2.4]hept-1-yl}benzenesulfonamide;
±trans 4-[(1R,3R)-3-{[4-fluoro-2-(trifluoromethyl)phenoxy]methyl}-2,2-dimethylcyclopropyl]-benzenesulfonamide;
±trans 4-{(1R,2R)-2-[2-(5-chloro-2-methoxyphenyl)ethyl]spiro[2.4]hept-1-yl}benzene-sulfonamide;
N-(4-{(1S,3S)-3-[(5-chloro-2-methoxyphenoxy)methyl]-2,2-dimethylcyclopropyl}phenyl)-methanesulfonamide;
N-{4-[(1S,3S)-3-{[(6-methoxypyridin-3-yl)oxy]methyl}-2,2-dimethylcyclopropyl]phenyl}-methanesulfonamide;
N-(4-{(1S,3S)-3-[(4-fluoro-2-methylphenoxy)methyl]-2,2-dimethylcyclopropyl}phenyl)-methanesulfonamide;
N-(4-{(1S,3S)-3-[(4-fluoro-2-methylphenoxy)methyl]-2,2-dimethylcyclopropyl}phenyl)sulfuric diamide;
N-(4-{(1S,3S)-3-[(5-fluoro-2-methylphenoxy)methyl]-2,2-dimethylcyclopropyl}phenyl)sulfuric diamide;
4-[(1S,3S)-3-{[4-fluoro-2-(trifluoromethyl)phenoxy]methyl}-2,2-dimethylcyclopropyl]benzene-sulfonamide;
4-{(1S,3S)-3-[(5-chloro-2-methoxyphenoxy)methyl]-2,2-dimethylcyclopropyl}benzene-sulfonamide;
4-{(1R,3R)-3-[(5-chloro-2-methoxyphenoxy)methyl]-2,2-dimethylcyclopropyl}benzene-sulfonamide;
4-[(1S,3S)-2,2-dimethyl-3-{[(4-methylphenyl)sulfanyl]methyl}cyclopropyl]benzene-sulfonamide;
4-[(1R,3R)-3-{[(5-chloro-2-methoxyphenyl)sulfanyl]methyl}-2,2-dimethylcyclopropyl]benzene-sulfonamide;
4-[(1R,3R)-2,2-dimethyl-3-{[(4-methylphenyl)sulfanyl]methyl}cyclopropyl]benzene-sulfonamide;
4-[(1S,3S)-3-{[(5-chloro-2-methoxyphenyl)sulfanyl]methyl}-2,2-dimethylcyclopropyl]benzene-sulfonamide;
N-{4-[(1S,3S)-3-{[(6-methoxypyridin-3-yl)oxy]methyl}-2,2-dimethylcyclopropyl]phenyl}-sulfuric diamide;
N-{4-[(1S,3S)-2,2-dimethyl-3-{[(6-methylpyridin-3-yl)oxy]methyl}cyclopropyl]phenyl}sulfuric diamide;
N-{4-[(1S,3S)-2,2-dimethyl-3-{[(2-methylpyridin-3-yl)oxy]methyl}cyclopropyl]phenyl}-methanesulfonamide;
N-{4-[(1S,3S)-2,2-dimethyl-3-{[(2-methylpyridin-3-yl)oxy]methyl}cyclopropyl]phenyl}sulfuric diamide;
4-[(1R,3R)-3-{[(2,6-dimethoxypyridin-3-yl)oxy]methyl}-2,2-dimethylcyclopropyl]benzene-sulfonamide;
4-[(1R,3R)-3-{[2-(difluoromethoxy)-5-fluorophenoxy]methyl}-2,2-dimethylcyclopropyl]-benzenesulfonamide;
N-(4-{(1S,3S)-3-[(4-chloro-2-methoxyphenoxy)methyl]-2,2-dimethylcyclopropyl}phenyl)-sulfuric diamide;
N-(4-{(1S,3S)-3-[(4-fluoro-2-methoxyphenoxy)methyl]-2,2-dimethylcyclopropyl}phenyl)-sulfuric diamide;
4-{(1S,3S)-2,2-dimethyl-3-[(pyridin-3-yloxy)methyl]cyclopropyl}benzenesulfonamide;
4-[(1S,3S)-3-{[(2,6-dimethoxypyridin-3-yl)oxy]methyl}-2,2-dimethylcyclopropyl]-benzenesulfonamide;
4-[(1R,3R)-2,2-dimethyl-3-{[(6-methylpyridin-3-yl)oxy]methyl}cyclopropyl]benzene-sulfonamide;
4-{(1R,3R)-3-[(2-cyano-4-fluorophenoxy)methyl]-2,2-dimethylcyclopropyl}benzene-sulfonamide;
4-{(1R,3R)-3-[(4-fluoro-2-methoxyphenoxy)methyl]-2,2-dimethylcyclopropyl}benzene-sulfonamide;
4-{(1S,3S)-3-[(4-fluoro-2-methoxyphenoxy)methyl]-2,2-dimethylcyclopropyl}benzene-sulfonamide;
4-{(1S,3S)-3-[(4-fluoro-2-methylphenoxy)methyl]-2,2-dimethylcyclopropyl}benzene-sulfonamide;
4-{(1S,3S)-3-[(2-cyano-4-fluorophenoxy)methyl]-2,2-dimethylcyclopropyl}benzene-sulfonamide;
4-[(1S,3S)-2,2-dimethyl-3-{[(6-methylpyridin-3-yl)oxy]methyl}cyclopropyl]benzene-sulfonamide;
4-[(1S,3S)-2,2-dimethyl-3-{[(2-methylpyridin-3-yl)oxy]methyl}cyclopropyl]benzene-sulfonamide;
4-{(1R,3R)-3-[(4-fluoro-2-methylphenoxy)methyl]-2,2-dimethylcyclopropyl}benzene-sulfonamide;
4-{(1S,3S)-3-[(5-fluoro-2-methoxyphenoxy)methyl]-2,2-dimethylcyclopropyl}benzene-sulfonamide;
4-{(1R,2R)-2-[(2-cyano-4-fluorophenoxy)methyl]cyclopropyl}benzenesulfonamide;
4-[(1R,2R)-2-{[4-fluoro-2-(trifluoromethyl)phenoxy]methyl}cyclopropyl]benzenesulfonamide;
4-[(1R,2R)-2-{[(2,6-dimethoxypyridin-3-yl)oxy]methyl}cyclopropyl]benzenesulfonamide;
4-{(1R,2R)-2-[(5-chloro-2-methoxyphenoxy)methyl]cyclopropyl}benzenesulfonamide;
4-{(1R,2R)-2-[(4-fluoro-2-methoxyphenoxy)methyl]cyclopropyl}benzenesulfonamide;
4-[(1R,3R)-3-{[2-(difluoromethoxy)phenoxy]methyl}-2,2-dimethylcyclopropyl]benzene-sulfonamide;
4-{(1R,3R)-3-[(5-fluoro-2-methoxyphenoxy)methyl]-2,2-dimethylcyclopropyl}benzene-sulfonamide;
4-{(1S,2S)-2-[(4-fluoro-2-methoxyphenoxy)methyl]cyclopropyl}benzenesulfonamide;
4-{(1S,2S)-2-[(2-cyano-4-fluorophenoxy)methyl]cyclopropyl}benzenesulfonamide;
4-[(1S,2S)-2-{[4-fluoro-2-(trifluoromethyl)phenoxy]methyl}cyclopropyl]benzenesulfonamide;
4-{(1S,2S)-2-[(5-chloro-2-methoxyphenoxy)methyl]cyclopropyl}benzenesulfonamide;
4-{(1R,3R)-3-[2-(2-methoxyphenyl)ethyl]-2,2-dimethylcyclopropyl}benzenesulfonamide;
4-{(1R,2R)-2-[2-(5-chloro-2-methoxyphenyl)ethyl]spiro[2.4]hept-1-yl}benzenesulfonamide;
4-{(1S,2S)-2-[2-(5-chloro-2-methoxyphenyl)ethyl]spiro[2.4]hept-1-yl}benzenesulfonamide;
4-{(1S,2S)-2-[2-(5-chloro-2-methoxyphenyl)ethyl]cyclopropyl}benzenesulfonamide;
4-{(1S,3S)-3-[2-(5-chloro-2-methoxyphenyl)ethyl]-2,2 dimethylcyclopropyl}benzene-sulfonamide;
4-{(1S,2R)-2-[(5-chloro-2-methoxyphenoxy)methyl]cyclopropyl}benzenesulfonamide;
4-{(1R,3R)-3-[2-(5-chloro-2-methoxyphenyl)ethyl]-2,2-dimethylcyclopropyl}benzene-sulfonamide; or
4-[(1R,3R)-3-{[(5-chloropyridin-2-yl)oxy]methyl}-2,2-dimethylcyclopropyl]benzene-sulfonamide;

4-[(1S,3S)-2,2-dimethyl-3-{[(2-methylpyrimidin-5-yl)oxy]
methyl}cyclopropyl]benzene-sulfonamide;
4-{(1S,3S)-2,2-dimethyl-3-[(pyrimidin-5-yloxy)methyl]
cyclopropyl}benzenesulfonamide; or
4-{(1S,2R)-2-[(2-cyano-4-fluorophenoxy)methyl]
cyclopropyl}benzenesulfonamide,
or a pharmaceutically acceptable salt of any of the foregoing.

DEFINITIONS

The term "alkyl" as used alone or in combination herein refers to a straight or branched chain saturated hydrocarbon group. The term "$C_{1-10}$ alkyl" refers to such a group containing from one to ten carbon atoms. Examples include methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "$C_{4-9}$ cycloalkyl", for instance, refers to such a group having from 4 to 9 carbon atoms. Examples include cyclobutyl, cyclopentyl and cyclohexyl.

The term "alkenyl" refers to a straight or branched hydrocarbon containing one or more double bonds, preferably one or two double bonds. Examples of alkenyl include allyl, 1-methylvinyl, butenyl, iso-butenyl, 1, 3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1, 3, 5-hexatrienyl.

The term "cycloalkenyl" refers to cyclic alkenyl groups having a single cyclic ring or multiple condensed rings, and at least one point of internal unsaturation. The term "$C_4$-$C_9$ cycloalkenyl", for instance, refers to such a group containing from four to eleven carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. Examples include 2-propynyl and 2- or 3-butynyl.

The term "alkoxy" as used alone or in combination refers to a straight or branched chain alkyl group covalently bound via an oxygen linkage (—O—). Examples include methoxy, ethoxy, propoxy, isopropoxy, butoxy, t-butoxy and the like.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "substituted" means that one or more of the moieties enumerated as substituents (or, where a list of substituents are not specifically enumerated, the substituents specified elsewhere in this application) for the particular type of substrate to which said substituent is appended, provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution by a moiety is described (e.g. "optionally substituted") the term means that if substituents are present, one or more of the enumerated (or default) moieties listed as optional substituents for the specified substrate can be present on the substrate in a bonding position normally occupied by the default substituent, for example, a hydrogen atom on an alkyl chain can be substituted by one of the optional substituents, in accordance with the definition of "substituted" presented herein.

Default substituents where the term "optionally substituted" is used and no list of such optional substituents is enumerated means that one or more hydrogen atoms on the group may be replaced by substituent groups independently selected from halogens (for example halo alkyl such as —$CF_3$), $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4$ S(O)$_q C_{1-6}$ alkyl, —C(Ph)$_3$, —CN, —OR$^c$, —O—(CH$_2$)$_{1-6}$—R$^c$, —O—(CH$_2$)$_{1-6}$—OR$^c$, —OC(O)R$^c$, —C(O) R$^c$, —C(O)OR$^c$, —OC(O)NR$^d$R$^e$, —NR$^d$R$^e$, —NR$^c$C(O)

$R^d$, —$NR^cC(O)NR^dR^e$, —$NR^cC(S)NR^dR^e$, —$NR^cS(O)_2R^d$, —$NR^cC(O)OR^d$, —$C(NR^c)NR^dR^e$, —$C(=NOR^d)R^c$, —$C(=NOH)NR^dR^e$, —$C(O)NR^dR^e$, —$C(=NCN)$—$NR^dR^e$, —$C(=NR^c)NR^dR^e$, —$C(=NR^d)SR^e$, —$NR^dC(=NCN)SR^e$, —$CONR^cSO_2R^d$, —$C(S)NR^dR^e$, —$S(O)_qR^c$, —$SO_2NR^dR^e$, —$SO_2NR^cC(O)R^d$, —$OS(O)_2R^c$, —$PO(OR^c)_2$ and —$NO_2$;

where p is 0-6, q is 0-2 and each $R^c$, $R^d$ and $R^e$ is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —$CO_2H$, $CF_3$, CN, phenyl, $NH_2$ and —$NO_2$; or when $R^d$ and $R^e$ are attached to the same nitrogen atom, they may, together with the atom to which they are attached, form a 5 to 7 membered nitrogen containing heterocyclic ring.

In some embodiments, optional substituents are preferably: fluoro, $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$P=O(OH)(NH_2)$, —$S(O)_2NH_2$, —$NHS(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$, —$S(O)R'''$ (where $R'''$ is lower alkyl or cycloalkyl) and —$S(O)_2R'''$ (where $R'''$ is lower alkyl, cycloalkyl or OH).

Unless otherwise defined and only in respect of the ring atoms of non-aromatic carbocyclic or heterocyclic compounds, the term "optional substituents" includes one or two oxy moieties (=O) appended to a carbon atom in the ring of such compounds, instead of or in addition to the above described "default" and "preferred default" list of optional substituents.

When the optional substituent is or contains an alkyl, alkenyl, alkynyl, cycloalkyl, aryl, heteroaryl or heterocyclyl group, the group may itself be optionally substituted with one to six of the same or different substituents selected from fluoro, $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$P=O(OH)(NH_2)$, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$, —$S(O)R'''$ (where $R'''$ is lower alkyl or cycloalkyl) and —$S(O)_2R'''$ (where $R'''$ is lower alkyl, cycloalkyl or OH).

DETAILED DESCRIPTION OF THE INVENTION

In relation to the aforementioned compounds one or more of the following preferred definitions (where appropriate) may also apply:

a) each $R_{1a}$ is independently selected from the group consisting of —C(O)NR'R", —NR'C(O)R", —NR'S(O)$_2$—NR"R'", —NR'S(O)$_2$R", —S(O)$_2$—NR'R" and —NR'R" (where each R', R" and R'" are independently selected from hydrogen, optionally substituted $C_{1-4}$ alkyl, optionally substituted $C_{3-7}$ cycloalkyl or optionally substituted heterocyclyl or R' and R" or R' and R'" or R" and R'" together form heterocyclyl), —S(O)R"" and —S(O)$_2$R"" (where R"" is optionally substituted $C_{1-4}$ alkyl, or $C_{3-7}$ cycloalkyl); when and b) z is 1.

In a further embodiment and with reference to all of the aforementioned formulae, the following additional definitions may also apply.

$R_7$ is selected from:

(a)

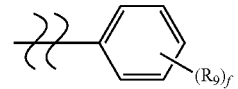

wherein r is 0, 1, 2 or 3 and each $R_9$ is independently selected from halogen, CN, $NO_2$, haloalkyl, aryl, heteroaryl, optionally substituted $C_{2-10}$ alkoxy, optionally substituted $C_{1-10}$ alkyl, or $CO_2R'$ (where R' is a $C_{1-10}$ alkyl or hydrogen); or (b) a heteroaryl substituted from 1 to 3 times from a group selected from optionally substituted $C_1$-$C_3$ alkyl, optionally substituted $C_{1-6}$ alkoxy, $C_{2-6}$alkenyl, $C_{2-6}$alkynyl, $C_{1-6}$ haloalkyl (in particular —$CF_3$), $C_{1-6}$haloalkoxy (such as —$OCF_3$), phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{2-10}$ alkoxycarbonyl, $CO_2H$, —$S(O)R''''$ (where R"" is lower alkyl or cycloalkyl) and $S(O)_2R''''$ (where R"" is lower alkyl, cycloalkyl or OH). Preferred heteroaryl groups include pyridinyl, pyrazolyl and thiazolyl.

In yet a further embodiment and with reference to the compounds of the invention of formulae (I), (Ib), (Ic), (Id), (Ie), (II) and (III):

$R_1$ is phenyl independently substituted by one or two substituents independently selected from the group consisting of cyano, fluoro, nitro, optionally substituted $C_{1-10}$ alkyl, optionally substituted aryl, optionally substituted aryloxy, optionally substituted benzyl, optionally substituted six-membered heteroaryl, five-membered heteroaryl, optionally substituted heterocyclyl, optionally substituted $C_{3-7}$ cycloalkyl, optionally substituted $C_{2-10}$ alkoxy, —$P=O(OH)NH_2$, —C(O)R, —C(O)OR, —OC(O)R (where each R is independently selected from hydrogen, optionally substituted $C_{2-10}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R'", —NR'S(O)$_2$R", —S(O)$_2$—NR'R" and NR'R" (where each R', R" and R'" are independently selected from hydrogen, optionally substituted $C_{1-4}$ alkyl, optionally substituted $C_{3-7}$ cycloalkyl or optionally substituted heterocyclyl, or R' and R" or R' and R'" or R" and R'" together form heterocyclyl), or —S(O)R"" and —S(O)$_2$R"" (where R"" is optionally substituted $C_{1-4}$ alkyl, or $C_{3-7}$ cycloalkyl);

$R_2$ and $R_3$ are the same and represent hydrogen, $C_{1-4}$ alkyl, or together a $C_4$-$C_6$ cycloalkyl or heterocyclyl;

$R_7$ is heteroaryl or heteroaryl independently substituted one or two times by cyano, halo, nitro, optionally substituted $C_{1-10}$ alkyl, optionally substituted aryl, optionally substituted aryloxy, optionally substituted benzyl, optionally substituted heteroaryl, optionally substituted heterocyclyl, optionally substituted $C_{3-7}$ cycloalkyl, optionally substituted $C_{1-10}$ alkoxy, —P=O(OH)NH$_2$, —C(O)R, —C(O)OR, —OC(O)R (where each R is independently selected from hydrogen, optionally substituted C$_{1-10}$ alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R", —NR'C(O)R", —NR'S(O)$_2$—NR"R''', —NR'S(O)$_2$R", —S(O)$_2$—NR'R" and —NR'R" (where each R', R" and R''' are independently selected from hydrogen, optionally substituted C$_{1-4}$ alkyl, optionally substituted C$_{3-7}$ cycloalkyl or optionally substituted heterocyclyl, or R' and R" or R' and R''' or R" and R''' together form heterocyclyl), or —S(O)R"" and —S(O)$_2$R"" (where R"" is optionally substituted C$_{1-4}$ alkyl, or C$_{3-7}$ cycloalkyl).

In a further embodiment and with reference to any one of formula (I), (Ia), (Ib), (Ic), (Id), (Ie), (II) and (III), n is 1-3, for instance, n=1, n=2, or n=3. Preferably n=1.

In an embodiment z is 1 and R$_{1a}$ is selected from:
—S(O)$_2$R''' (where R''' is C$_{1-4}$ alkyl, or cycloalkyl);
—S(O)$_2$NR'R" (where R' is hydrogen and R" is selected from hydrogen or C$_{1-4}$ alkyl);
—NR'S(O)$_2$—NR"R''' (where R' and R" are hydrogen and R''' is selected from hydrogen, C$_{1-4}$ alkyl, C$_3$-C$_7$ cycloalkyl, heterocyclyl, or heteroaryl); or
—NR'—S(O)$_2$R' (where each R' is independently selected from hydrogen or lower alkyl, C$_3$-C$_7$ cycloalkyl, heterocyclyl, or heteroaryl).

In a further embodiment the R$_{1a}$ substituent is in the para position.

In an embodiment z is 1 and R$_{1a}$ is selected from

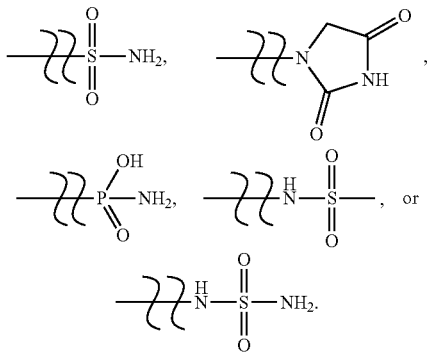

In the list below (which are representative examples of compounds of the present invention) the structures contain one or more stereogenic centers, the respective structures are depicted in an arbitrary absolute configuration. These structures also include the respective structure having the opposite stereochemistry as well as mixtures of isomers in all ratios including racemates:

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula IA, and of the salts, solvates and prodrugs of the compounds of Formula IA, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

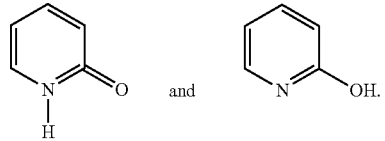

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the protected compound is subjected to particular reaction conditions aimed at modifying another region of the molecule. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}$I and $^{125}$I. It will be appreciated that other isotopes may be incorporated by know means also.

Certain isotopically-labeled compounds of the invention (e.g., those labeled with $^3$H, $^{11}$C and $^{14}$C) are recognized as being particularly useful in compound and/or substrate tissue distribution assays using a variety of known techniques. Tritiated (i.e., $^3$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

In one aspect, as mentioned above, the present invention provides pharmaceutical compositions for use in antagonizing $A_{2A}$ receptors, believed to be useful in treating, amolerating, or managing central nervous system (CNS) disorders, for example, movement disorders associated with Parkinson's disease or the treatment or management thereof, wherein the compositions comprising at least one compound, or pharmaceutically acceptable salt thereof, of Formulae G, A, B or C, as defined herein and at least one other excipient (described below).

It will be appreciated that pharmaceutically formulations of the invention may comprise more than one compound of the invention, for example, the combination of two or three compounds of the invention, each present in such a composition by adding to the formulation the desired amount of the compound in a pharmaceutically acceptably pure form. It will be appreciated also that in formulating compositions of the invention, a composition may comprise, in addition to one or more of compounds of the invention, one or more other compounds which also have pharmacological activity, for example, as described herein below.

The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of the invention, or salts thereof. Pharmaceutically acceptable derivatives may include any pharmaceutically acceptable hydrate or any other compound or prodrug which, upon administration to a subject, is capable of providing (directly or indirectly) a compound of the invention, or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of salt thereof.

It will be appreciated that the compounds of the invention have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

It will be appreciated that in respect of the cyclopropyl carbons which connect variables $R_1$ and $R_4$ that these chiral positions give rise to various stereoisomers. In an embodiment the invention contemplates trans-isomers. In another embodiment the invention contemplates cis-isomers. In a further embodiment the invention contemplates an enantiomeric mixture of trans-isomers. In a further embodiment the invention provides a single trans-enantiomer, or an enantiomerically enriched mixture thereof. In a further embodiment, the invention contemplates S,S isomers. In a further embodiment, the invention contemplates R,R isomers.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use as a positive allosteric modulator of α7 nAChRs, for instance in the treatment or prevention of cognitive deficits associated with neurodegeneration or neuropsychiatric diseases, or in treating inflammation or in treating neuropathic pain, the composition comprising an effective amount of a compound of the invention, or a pharmaceutically acceptable salt thereof, including a pharmaceutically acceptable derivative thereof, and optionally a pharmaceutically acceptable carrier or diluent.

Accordingly these compositions may be thought as either antiinflammatory or neuroprotective agents or analgesics.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy. For example the pharmaceutical preparation of the active compound may be co-administered (for example, separately, concurrently or sequentially), with one or more other agents used to treat cognitive impairment or mood disorders such as acetylcholine esterase inhibitors, antipsychotics, and antidepressants.

It is believed that the compounds of the invention may be beneficial in treating patients with cognition impairment or aid in increasing cognition. It is believed that this effect may be brought about by positive allosteric modulation of α7 nAChRs. Positive allosteric modulators (PAMs) of nicotinic acetylcholine receptors (nAChRs) can be characterised by two types (type I and type II). Whilst both potentiate peak agonist-induced responses, they have different effects on the rate of agonist-induced receptor desensitization. Type I PAMs have little or no effect on the rapid rate of desensitization that is characteristic of α7 nAChRs, whereas type II PAMs cause dramatic slowing of receptor desensitization.

In one embodiment the compounds of formula (I), (Ia), (Ib), (Ic), (Id), (Ie), (II) and (III) are characterised as type I.

In one embodiment the compounds of formula (I), (Ia), (Ib), (Ic), (Id), (Ie), (II) and (III) are characterised as type II.

It is envisaged that the compounds may additionally be useful in the treatment of patients, including a mammal and especially a human, suffering from neuropsychiatric diseases and neurodegenerative diseases involving a dysfunction of the cholinergic system, and further conditions of memory and/or cognitive impairment, including, for example, schizophrenia, Attention Deficit Hyperactivity Disorder, anxiety, mania, depression, manic depression (as examples of neuropsychiatric disorders), Tourette's syndrome, Parkinson's disease, Huntington's disease (as examples of neurodegenerative diseases), and/or cognitive disorders (such as Alzheimer's disease, Lewy Body Dementia, Amyotrophic Lateral Sclerosis, memory impairment, memory loss, cognition deficit).

Neurodegenerative disorders include, but are not limited to, treatment and/or prophylaxis of Alzheimer's diseases, Pick's disease, diffuse Lewy Body disease, progressive supranuclear palsy (or Steel-Richardson syndrome), multisystem degeneration (or Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia.

The invention provides methods of treating subjects suffering from memory impairment due to, for example, Alzheimer's disease, mild cognitive impairment due to aging, schizophrenia, Attention Deficit Hyperactivity Disorder, Parkinson's disease, multiple sclerosis, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases.

For certain of the abovementioned conditions it is clear that the compounds may be used prophylactically as well as for the alleviation of symptoms.

References herein to "treatment" or the like are to be understood to include such prophylactic treatment, as well as therapeutic treatments.

The compounds of the present invention as agents which modulate the α7 nAChR may be particularly useful in the therapeutic or prophylactic treatment of diseases such as schizophrenia, bi-polar disorder, anxiety, AD, ADHD, mild cognitive impairment, Parkinson's Disease, Huntington's disease, Tourette's syndrome, brain trauma, jetlag and nicotine addiction.

Accordingly in a further aspect of the invention, there is provided a means for ameliorating the cognitive deficits associated with neurodegenerative and neuropsychiatric diseases and also inflammatory diseases by the application of a positive allosteric modulators of α7 nAChRs selected from a compound of the invention, or salt thereof, including a pharmaceutically acceptable derivative thereof, or a composition comprising the compound of the invention, or salt thereof, or a pharmaceutically acceptable derivative thereof.

In another aspect of the invention a method is provided for preventing or treating cognitive deficits involving dysfunction of the cholinergic system including the step of administrating a compound of the invention, or salt thereof, or a composition comprising the compound or salt thereof.

In another preferred form of the invention there is provided a method for preventing or treating neurodegenerative or neuropsychiatric disorders including the step of administrating a compound of the invention, or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect of the present invention, there is provided the use of a compound of the invention, or salt thereof, in the preparation of a medicament for the treatment (therapeutic or prophylactic) of disease states in which modulation of α7 nAChRs would be beneficial.

In a further aspect of the invention there is provided a process for the production of the compounds of the invention, or salts thereof, including pharmaceutically acceptable derivatives thereof.

Compounds of the invention may be prepared according to the following general schemes:

Acronyms

For convenience, many chemical moieties are represented using well known abbreviations, including but not limited to, methyl (Me), ethyl (Et), n-propyl (n-Pr), iso-propyl (i-Pr), n-butyl (n-Bu), tert-butyl (t-Bu), n-hexyl (n-Hex), cyclohexyl (c-Hex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), ethyl acetate (EtOAc), triethylamine ($Et_3N$), dichloromethane (methylene chloride, DCM), trifluoroacetic acid (TFA), trifluoroethanol (TFE), dimethylformamide (DMF), sodium sulphate ($Na_2SO_4$), tetrahydrofuran (THF), meta-chloroperbenzoic acid (m-CPBA), hexamethyldisilazane sodium salt (NaHMDS), O-(7-azabenzotriazol-1-yl)-N,N,N',N'-tetramethyluroniumhexafluorophosphate (HATU), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl) carbodiimide hydrochloride salt (EDCl.HCl), tetra-n-butylammonium fluoride (TBAF), N,N-diisopropylethylamine (DIPEA), 1-hydroxybenzotriazole (HOBt), trans-dichlorobis(triphenylphosphine)palladium(II) ($PdCl_2(PPh_3)_2$), 2-di-tert-butylphosphino-2',4',6'-triisopropylbiphenyl (t-BuXPhos), tris(dibenzylideneacetone) dipalladium(0) ($Pd_2(dba)_3$), tri-t-butyl phosphoniumtetrafluoroborate (t-$Bu_3PH.BF_4$), 4,5-bis(diphenylphosphino)-9,9-dimethylxanthene (Xantphos), triphenylphosphine ($PPh_3$), diisopropylazodicarboxylate (DIAD), pyridiniumchlorochromate (PCC), boranedimethylsulfide (BMS) and 1,2-dichloroethane (DCE).

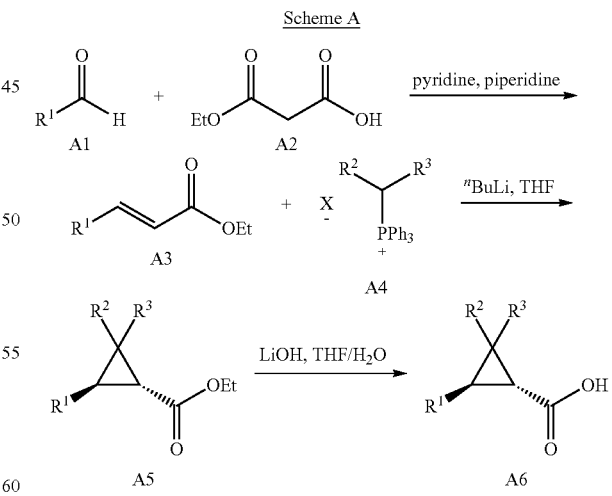

Scheme A outlines the synthesis of cyclopropyl esters A5 and acids A6 Cinnamate esters A1 may be from commercial sources or prepared by Doebner modification of Knoevenagel condensation of an aryl/heteroaryl aldehyde. Typically, an aryl/heteroaryl aldehyde A1 and ester of malonic acid A2 is heated in pyridine/piperidine mixture. Numerous modifications of this procedure as well as alternatives such as Aldol-type condensation or Wittig reaction of aryl or heteroaryl carbonyl compounds with ylides are possible and will be readily apparent to those skilled in the art.

Cyclopropanation of olefin was carried out by reacting cinnamate ester A3 with phosphorus ylides derived from phosphonium salts A4 (where X=Cl, Br, I) as described in *J. Med. Chem.* 2001, 44, 3302. The requisite phosphonium salts can be purchased or prepared by known methods. Those skilled in the art will understand that cyclopropanation of olefins could be achieved by alternative methods, such as Simmons-Smith type reaction of cinnamate ester with Furukawa reagents as described in *Tetrahedron* 1969, 25, 2647 or Michael initiated ring closing reaction of cinnamate ester with sulphur ylides as described in *Synthesis* 2008, 20, 3279. Additionally, treatment of olefins with diazoesters in the presence of metal catalysts can afford access to cyclopropane esters of type A5 with either cis or trans orientation of $R^1$ to the ester moiety favoured depending on catalyst used (*Tetrahedron* 2008, 7041). Numerous modifications of this procedure such as use of trichloroacetic acid in acetic anhydride as described in *J. Org. Chem.* 1988, 53, 4945 are possible and will be readily apparent to those skilled in the art. Esters A4 where $R^2$ and $R^3$ together form a cycloalkyl or cycloalkenyl group can be prepared by from corresponding spiro group containing phosphorus ylides. Alternatively, phosphorus ylides where $R^2$ and $R^3$ contains terminal alkene group can be reacted with cinnamate esters, followed by ring-closure metathesis as described in *J. Chem. Res.* 2006, 9, 591 to form ester A5 where $R_2$ and $R_3$ together form cycloalkenyl group, which could be further reduced to form corresponding cycloalkyl group containing ester A5. Ester A5 can be alternatively prepared by the reaction of styrenes with diazoesters giving cyclopropanes in high enantiomeric and diastereomeric excess using chiral ligands and metal catalysts as outlined in *J. Am. Chem. Soc.* 1991, 726.

Ester A5 can be hydrolysed to acid A6 by using known procedures. Conversely, the commercially purchased acid A6 can be esterified to ester A5 using standard literature conditions, such as heating the acid A6 with trimethylorthoformate in ethanol in presence of sulphuric acid.

Scheme B

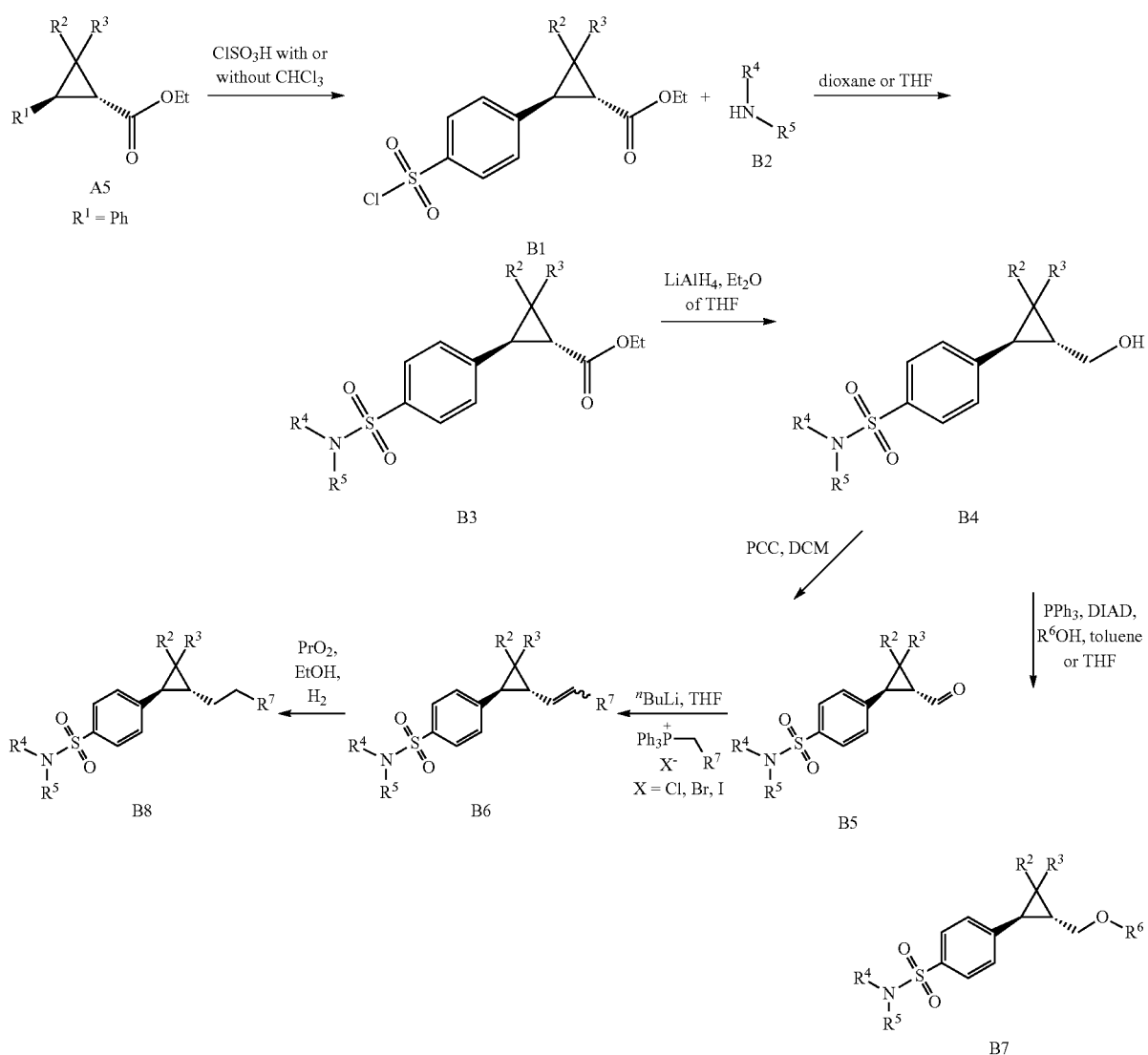

Ester A5 can be converted to sulfonyl chloride B1, through treatment with chlorosulfonic acid and subsequently allowed to react with amine B2 to generate sulfonamide ester B3. Ester B3 may be reduced using standard conditions, such as lithium aluminium hydride in anhydrous diethyl ether or THF, to give alcohol B4. Mitsunobu reaction between alcohol B4 and an optionally substituted phenol or hydroxyl substituted heterocycle can be achieved using standard procedures to provide ether derivatives of formula B7. Alcohol B4 may be oxidised using standard conditions, such as pyridinium chlorochromate in dichloromethane, to give aldehyde B5. Alternative oxidation conditions such as Swern Oxidation or $MnO_2$ could be used to generate aldehyde B5. Wittig reaction of aldehyde B5 allows access to compounds B6 which upon reduction using standard conditions, such as platinum oxide and hydrogen in ethanol, gives rise to compounds of formula B8.

With reference to Scheme C, below, bromination of cyclopropyl acid A6 to give compound C1 can be achieved in reaction with bromine in aqueous sodium hydrogen carbonate solution. Access to alcohol C3 can be achieved via direct reduction of cyclopropyl acid C1 using sodium borohydride in the presence of iodine in THF or other similar reagent systems. Alternatively, a step-wise process of esterification of C1 using standard conditions to ester C2, followed by reduction again using standard conditions, such as lithium aluminium hydride in anhydrous diethyl ether or THF, gives access to alcohol C3. Mitsunobu reaction between alcohol C3 and an optionally substituted phenol or hydroxyl substituted heterocycle can be achieved using standard procedures to provide ethers of formula C4. Palladium catalysed coupling of C4 with an optionally substituted sulfonamide C6 can generate sulfonamides of formula C7. Similarly, palladium catalysed coupling of bromo derivative C4 with an optionally substituted sulfamide C5 or C8 can generate sulfamides of formula C9 or C10, respectively. N-boc group of C9 can be removed with standard methods such as treating with TFA in DCM to provide sulfamide of formula C11.

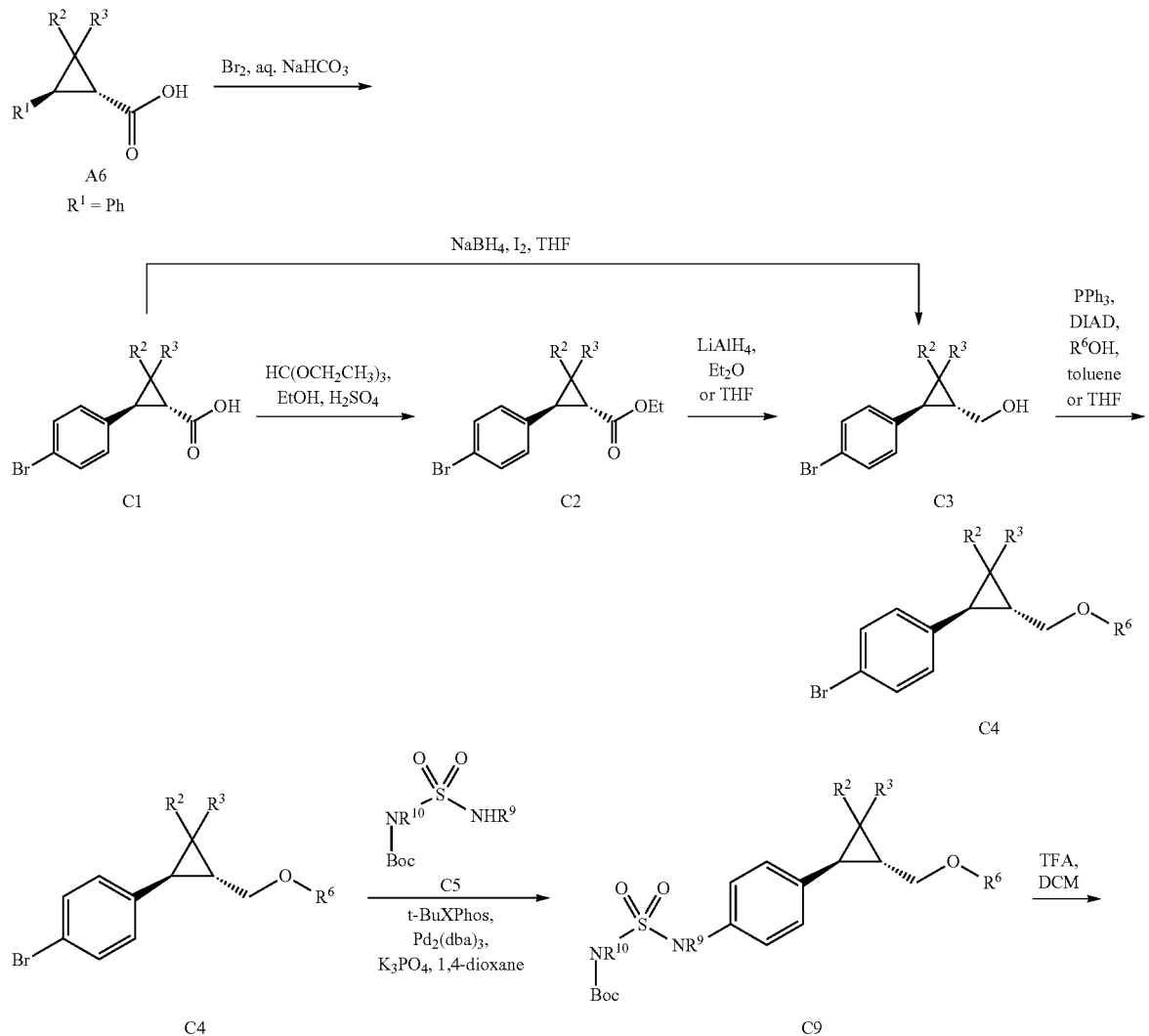

Scheme C

-continued
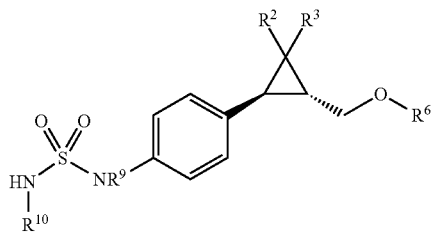
C11
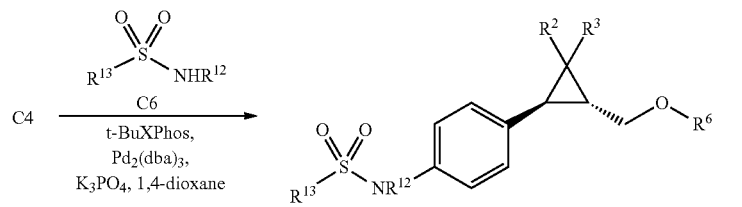
C7
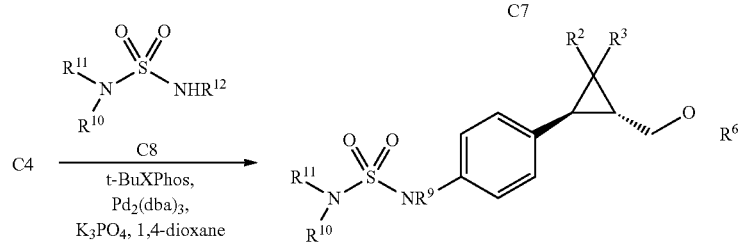
C10

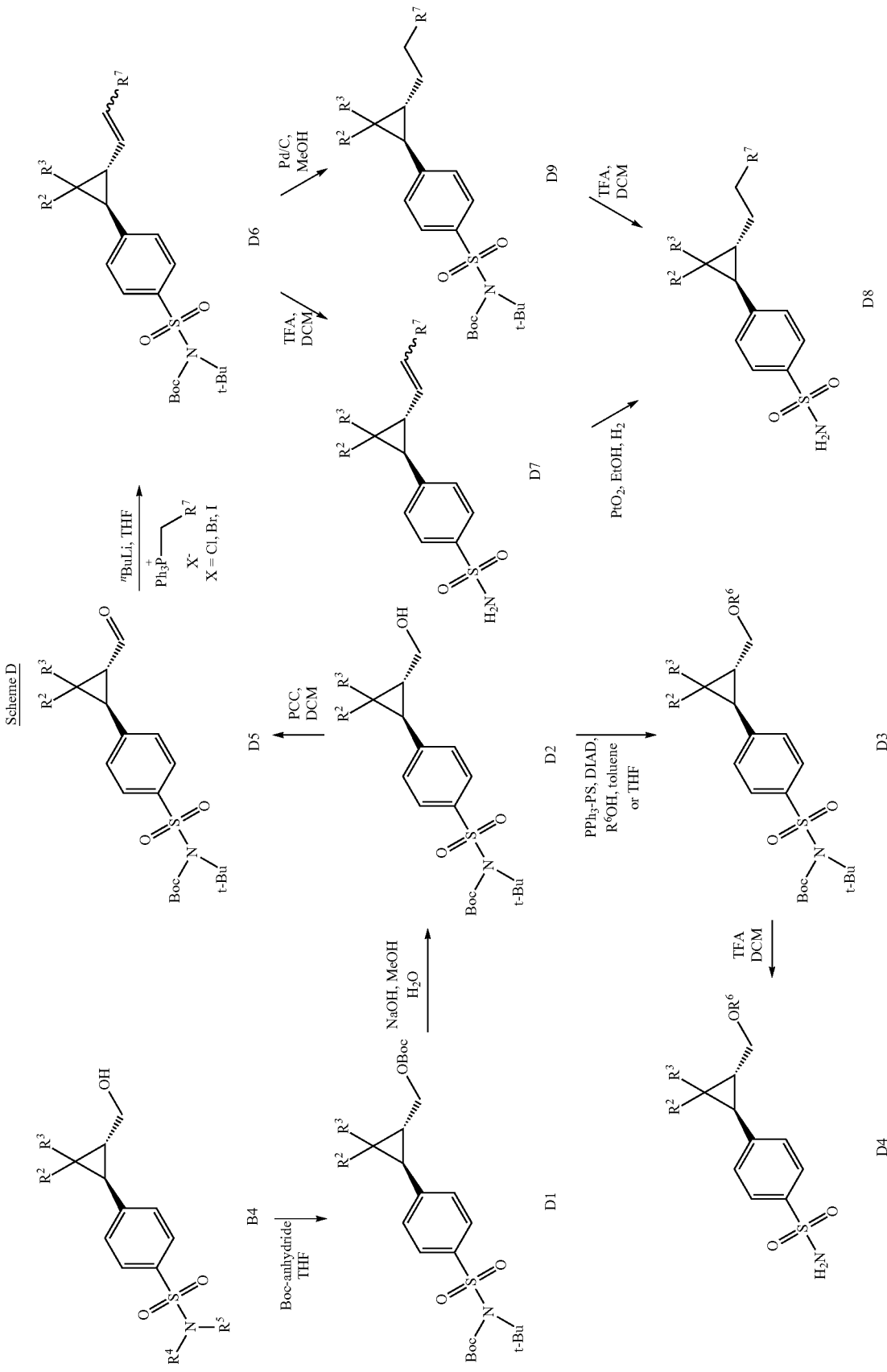
Scheme D

With reference to Scheme D, above, alcohol B4 ($R^4$, $R^5$=H) may be treated with di-tert-butyl dicarbonate to yield the protected sulfonamide alcohol D1, followed by selective deprotection of O-boc to give N-boc-N-tert-butyl protected sulfonamide D2. Sulfonamide D2 can be condensed with phenols using Mitsunobu conditions to yield the protected ethers of formula D3. N-boc-N-tert-butyl groups of D3 can be removed by using literature reported reaction conditions such as TFA in DCM etc. to offer ethers compounds of invention D4. Alcohol D2 may be oxidized using standard conditions, such as pyridinium chlorochromate in dichloromethane, to give aldehyde D5. Alternative oxidation conditions such as Swern Oxidation or $MnO_2$ could be used to generate aldehyde D5. Wittig reaction of aldehyde D5 allows access to compounds of formula D6 which can be treated with acidic conditions, such as TFA in DCM to offer the compounds of formula D7. Transition metal catalysed reduction of D7, such as platinum oxide and hydrogen in ethanol, gives rise to compounds of formula D8. Alternatively, D8 can made by metal, eg palladium over charcoal catalysed reduction of D6 to D9, followed by treatment with acidic conditions, such as TFA in DCM.

toluene, followed by base catalysed saponification can generate required aryl or heteroaryl thiol E3. Thiol E3 can be treated with mild oxidising system, such as iodine in ethanol to offer disulfide E4. Alcohol D2 can be condensed with disulphide E4 using tri-n-butylphosphine in dry pyridine to offer the thioethers of formula E5, which can be treated with TFA in DCM to offer the compounds of invention E6. Alternatively, thioethers of formula E6 can be accessed through the aldehyde D5 by reaction with aromatic or heteroaromatic thiol E3 in the presence of triethylsilane and trifluoroborane monohydrate.

Another variation is to add, remove or modify the substituents of the products and intermediates outlined in Schemes A, B and C to form new derivatives. This could be achieved again by using standard techniques for functional group inter-conversion, well known in the industry such as those described in Comprehensive Organic Transformations: A Guide to Functional Group Preparations by Larock R C, New York, VCH Publishers, Inc. 1989.

General Experimental Details

Unless otherwise stated the following generalisations apply.

In the examples below, in case the structures contain one or more stereogenic centres and the stereochemistry is Scheme E

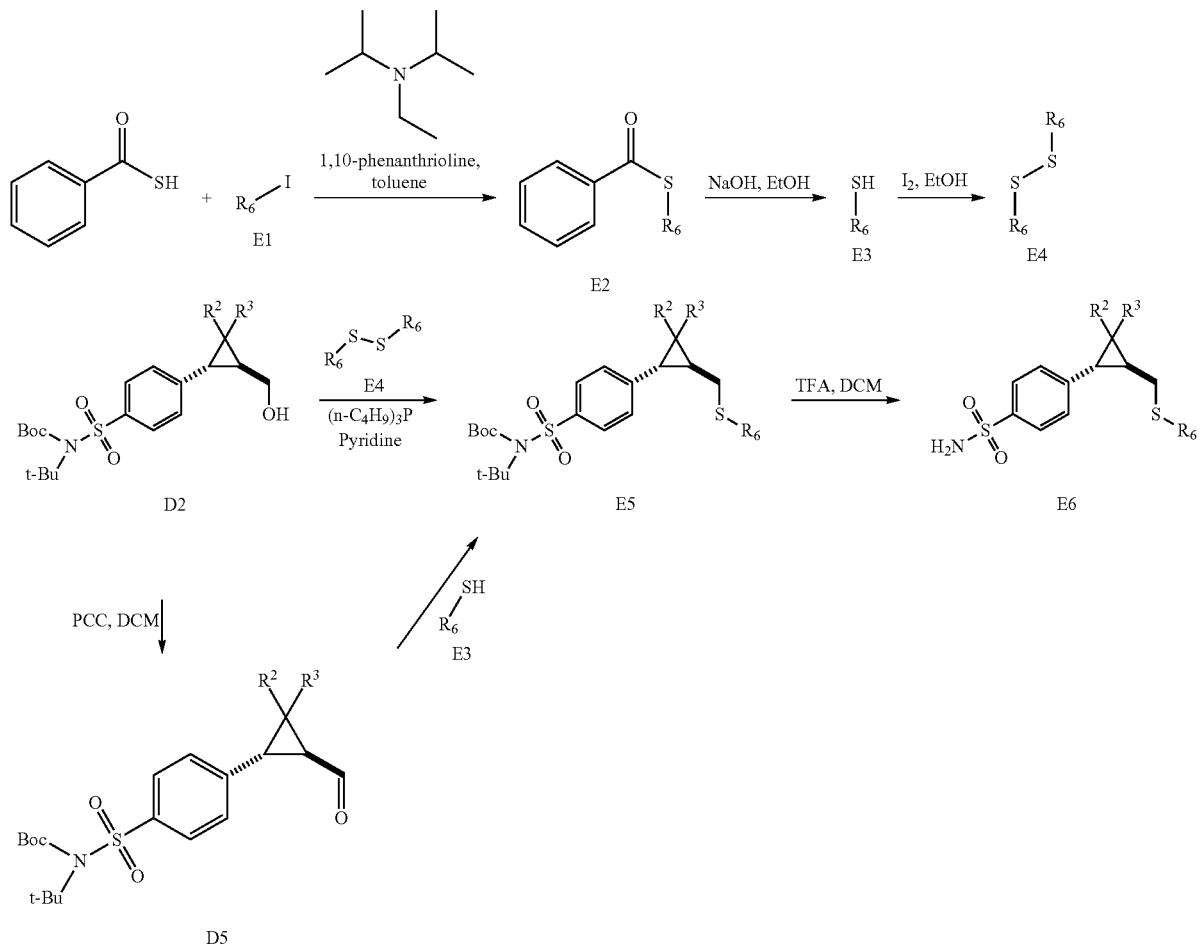

Aromatic or heteroaromatic disulfides E4 can be purchased from commercial sources or can be prepared from thiobenzoic acid. Esterification of thiobenzoic acid with aryl or heteroaryl iodide E1 at high temperature in presence of 1,10-phenanthroline and N,N-diisopropylethylamine in depicted in the diagram, the respective stereochemistry is assigned in an arbitrary absolute configuration. These structures depict single enantiomers as well as mixtures of enantiomers in all ratios, and/or mixtures of diastereoisomers in all ratios.

The compounds of formula (I) have been named according to the standards used in the program ACD/Name Chemist Version from Advanced Chemistry Development Inc., ACD/Labs 2012 Release (Build 53475, 31 Jan. 2012). NMR, HPLC, MS and Mp data provided in the examples described below are registered on:

NMR: Agilent DD2 (500 MHz), Agilent DD2 (600 MHz) or Varian DD2 (300 MHz) using residual signal of deuterated solvent as internal reference.

LCMS: Agilent 1100 Series LC/MSD, column Luna 5 µm C8, 150×4.6 mm, with mobile phase 80% ACN, 15% H2O, 5% buffer (3:1 MeOH/H2O, 315 mg HCO2NH4, 1 mL AcOH) and MS detection (ESI method).

Melting point: SRS OptiMelt—Automated Melting Point System

HRMS: Agilent Technologies 6230 TOF LC/MS system with 1260 Infinity LC modules

Analytical thin-layer chromatography (TLC) was performed on Merck silica gel 60F254 aluminium-backed plates which were visualised using fluorescence quenching under UV light or using an acidic anisaldehyde, acidic vanillin or a basic potassium permanganate dip. Flash chromatography was performed using a Teledyne IscoCombi-FlashRf purification system using standard RediSep® cartridges. Microwave irradiation was achieved using a CEM Explorer 48 Microwave Reactor. All reactions carried out using microwave irradiation were stirred.

Where necessary, anhydrous solvents were prepared using a Glascontour purification system or purchased from Sigma-Aldrich.

General Procedure A: Cyclopropanation of α,β-Unsaturated Esters

To a suspension of the phosphonium halide (A4) (1.2 equiv.) in anhydrous THF (0.3 M) at −78° C. was added n-BuLi (2.0 M in cyclohexane, 1.1 equiv.) under an nitrogen atmosphere. The resulting mixture was warmed to 0° C. and stirred for 30 min. The reaction mixture was cooled to −78° C. followed by the addition of a solution of the α,β-unsaturated ester (A3) (1.0 equiv.) in anhydrous THF (0.5 M). The reaction mixture was stirred for 2 h at 0° C., then slowly warmed to ambient temperature and stirred overnight. The solution was poured onto 1N HCl. The aqueous layer was extracted with ethyl acetate and the combined organic layers were sequentially washed with saturated NaHCO$_3$, brine, dried over Na$_2$SO$_4$, and concentrated in vacuo. The crude cyclopropane was purified by column chromatography to furnish the pure cyclopropyl ester (A5).

General Procedure B: Hydrolysis of Ester

To a stirred solution of cyclopropyl ester (A5) (1 equiv.) in THF:water 9:1 (8 ml/g of cyclopropane) was added LiOH.3H$_2$O (2 equiv.) and the mixture was stirred at ambient temperature for 16 h. After completion of the reaction, the reaction mixture was diluted with water and washed with diethyl ether. The aqueous layer was acidified using 1.5N HCl and extracted with EtOAc. The combined organic layers were washed with water and brine solution, dried over sodium sulphate and concentrated to afford the acid derivatives A6.

General Procedure C: Formation of Sulfonyl Chlorides

To chlorosulfonic acid (7-12 equiv.) at 0° C. under a nitrogen atmosphere was added cyclopropane derivative (A5) (1 equiv., neat or solution in minimum amount of sulfolane or chloroform), portion-wise/dropwise. The mixture was then stirred at ambient temperature for 1 h before pouring over ice/water mixture (50 g/1 g cyclopropane) with rapid stirring. The solid precipitate was collected by filtration and washed with water to yield the sulfonyl chloride (B1) which was used without further purification. Alternatively, the crude material from aqueous was extracted with EtOAc and evaporated to offer sulfonyl chloride (B1) which was used without further purification.

General Procedure D: Formation of Sulfonamides

To the sulfonyl chloride (B1) (1 equiv.) in a conical flask was added THF or 1,4-dioxane (70 ml/1 g cyclopropane), to this solution was added amine (B2) (excess) with rapid stirring. The mixture was stirred for 0.5-2 h and the volatiles removed in vacuo. The crude material was then taken up in ethyl acetate and water and the pH of the water layer was adjusted to neutral and the layers separated. The organic layer was further extracted with water and brine, then dried (MgSO4), filtered and concentrated in vacuo to give the desired sulfonamide (B3).

General Procedure E: Reduction of Esters to Alcohols

To a cooled (0° C.) solution of ester (B3 or C2) (1 equiv.) in anhydrous Et$_2$O or THF (50 ml/1 g ester) was added LiAlH$_4$ (4 equiv.) in one portion and the evolution of gas was observed. The reaction mixture was stirred for 20 min at 0° C. before warming to ambient temperature. After the reaction was complete and the reaction was cooled to 0° C. and quenched by careful addition of potassium sodium tartrate tetrahydrate (1.0 M aq. solution). The mixture was stirred at room temperature for 1 h before neutralising with HCl (2 M). The product was extracted with EtOAc and the combined organic extracts washed with brine, dried (MgSO$_4$) and concentrated in vacuo. The crude residue was purified by column chromatography to furnish the desired alcohol (B4 or C3).

General Procedure F: Bromination

To a stirred solution of cyclopropanecarboxylic acid (A6) (1 equiv.) in 10% aqueous sodium bicarbonate solution (40 ml/g of cyclopropane carboxylic acid) was added bromine (1 equiv.) drop-wise at room temperature. The resulting mixture was allowed to stir at room temperature until complete. Once complete the reaction was acidified with conc. HCl to pH ~2 and was extracted with DCM. The combined organic layers were dried over anhydrous MgSO$_4$, evaporated under reduced pressure to afford brominated cyclopropane carboxylic acids (C1), which were further purified by recrystallisation.

General Procedure G: Reduction of Carboxylic Acids to Alcohols

A solution of the cyclopropylcarboxylic acid (C1) (1 equiv.) in anhydrous THF (10 ml/g of cyclopropane), under a nitrogen atmosphere, was added slowly to a suspension of NaBH$_4$ (2.7 equiv.) in anhydrous THF (10 ml/g of cyclopropane) at 0° C. The mixture was stirred until the evolution of gas had ceased. Iodine (1.08 equiv.) in anhydrous THF (10 ml/g of cyclopropane) was then added drop-wise and the reaction mixture was then warmed to rt. Once complete the reaction mixture was carefully quenched with 2M HCl aq. sol. to pH 2 and allowed to stir at rt for 10 min. The solution was extracted with diethyl ether, washed with brine and dried over MgSO$_4$ before concentrating in vacuo. The crude residue was purified by column chromatography give the pure desired cyclopropyl alcohol (C3).

General Procedure H: Mitsunobu Reaction of Phenols and Alcohols

To a solution of the cyclopropyl alcohol (B4 or C3) (1 equiv.) and phenol (R$^6$OH) (1.2-2.0 equiv.) in anhydrous toluene or THF (25 ml/g of cyclopropyl alcohol), under a nitrogen atmosphere, at 0° C. was added PPh$_3$ (1.0-1.3 equiv.) followed by DIAD (1.0-1.4 equiv.) drop-wise. The reaction mixture was stirred at 0° C. for 30 minutes before warming to room temperature and stirring was continued until complete. The reaction mixture was concentrated in vacuo and the residue purified directly by column chromatography to furnish the desired ether (B7 or C4).

General Procedure I: Palladium Coupling of Sulfamides or Sulfonamides

A solution of cyclopropyl ether (C4) (1 equiv.), sulfonamide or sulfamide (1.2-7.0 equiv.) and potassium phosphate (1.1 equiv.) in 1,4-dioxane (10 ml/g of cyclopropyl ether) was purged with $N_2$ for 5 min. To this was added tBuXPhos (0.15 equiv.) and $Pd_2(dba)_3$ (0.05 equiv.) and the mixture was allowed to stir at 55-80° C. until complete. Once complete water was added and the mixture was extracted with ethyl acetate. The organics were combined and washed with water and brine before drying over $MgSO_4$ and concentrated in vacuo. The crude residue was purified directly by column chromatography or preparative TLC to furnish the desired sulfonamides or sulfamides (C7, C9 or C10).

General Procedure J: Removal of Boc Protecting Group

To a solution of Boc protected sulfamide (C9) (1 equiv.) in anhydrous DCM (10 ml/g of Boc protected sulfamide) at 0° C., under a nitrogen atmosphere, was added drop-wise TFA (5-10 ml/g of Boc protected sulfamide). Once addition was complete the mixture was allowed to attain ambient temperature and stirred until complete. Once complete the mixture was concentrated in vacuo, sat. aq. $NaHCO_3$ was added and the mixture was extracted with DCM. The combined organics were dried over $MgSO_4$ and concentrated in vacuo and the residue purified by column chromatography or preparative TLC to furnish the sulfamide (C11).

General Procedure K: Oxidation of Alcohols to Aldehydes

A solution of alcohol B4 or D2 (1.0 equiv.) in anhydrous dichloromethane (0.2 M) under an argon atmosphere was rapidly added to a slurry of pyridiniumchlorochromate (2.0-3.0 equiv.) in anhydrous dichloromethane (0.3 M) and this mixture was stirred at ambient temperature until complete. The mixture was passed through a plug of silica gel topped up with celite and or Celite only, eluting with diethyl ether or EtOAc in DCM. The filtrate was concentrated in vacuo and the crude residue which was either used without further purification or was purified by column chromatography to furnish the desired aldehyde (B5 or D5).

General Procedure L: Wittig Reaction

To a suspension of phosphonium halide (1.0-2.0 equiv.) in anhydrous THF (0.3 M) at −78° C. was added n-BuLi (2.0 M in cyclohexane, 1.0-2.0 equiv.) under an inert (nitrogen or argon) atmosphere. The resulting mixture was warmed to 0° C. and stirred for 30 min. The reaction mixture was cooled to −78° C. followed by the addition of a solution of aldehyde (B5 or D5) (1 equiv.) in anhydrous THF (0.5 M). The reaction mixture was stirred for 2 h at 0° C., then slowly warmed to ambient temperature and stirred overnight. The solution was poured onto 1N HCl. The aqueous layer was extracted with ethyl acetate and the combined organic layers were sequentially washed with saturated $NaHCO_3$, brine, dried over $Na_2SO_4$, and concentrated in vacuo. The crude alkene was purified by column chromatography to furnish the alkene (B6 or D6) as a mixture of E and Z isomers.

General Procedure M: Reduction of Alkenes

To a solution of alkene (B6 or D7) in ethanol (30 ml/g of alkene) was added $PtO_2$ and the reaction stirred under 1 atmosphere of hydrogen at ambient temperature until complete. Once complete the mixture was passed through a plug of Celite, eluting with diethyl ether. The filtrate was concentrated in vacuo and the crude residue was purified by column chromatography to furnish the desired cyclopropyl alkane (B8 or D7).

General Procedure N: Mitsunobu Reaction of Phenols and Alcohols Using Polymer Supported Triphenylphosphine.

To a solution of the cyclopropylalcohol (B4, C3 or D2) (1 equiv.) and phenol ($R^6OH$) (1.2 equiv.) in anhydrous toluene or THF (10-25 ml/g of cyclopropyl alcohol), under a nitrogen atmosphere, at ambient temperature was added polymer supported triphenylphosphine $PPh_3$-PS (1.0-2.0 equiv., 100-200 mesh, ~3.0 mmol/g loading, 2% cross-link with divinylbenzene), followed by DIAD (1.0-2.0 equiv.) drop-wise. The reaction mixture was stirred at ambient temperature until complete. The reaction mixture was filtered through sintered funnel, filtrate was concentrated in vacuo and the residue purified directly by column chromatography or preparative TLC to furnish the desired ether (B7, C4 or D3).

General Procedure O: Protection of Sulfonamide Alcohol

To a solution of sulfonamide alcohol (B4, $R^4$, $R^5$=H) (1.0 equiv.) in anhydrous THF (5-10 ml/g of alcohol) at 0° C., under a nitrogen atmosphere, was added di-tert-butyl dicarbonate (6-8.0 equiv.) followed by N,N'-dimethylaminopyridine (0.1 equiv.) and reaction mixture was stirred at 45-60° C. under nitrogen atmosphere until complete. Once complete, the mixture was diluted with sat. aq. $NaHCO_3$ and extracted with diethyl ether or EtOAc (25 mL/g of alcohol) twice. The combined organics were dried over $MgSO_4$ and concentrated in vacuo and the residue purified by column chromatography to furnish the protected sulfonamide (D1).

General Procedure P: Removal of O-Boc Protecting Group

To a solution of protected sulfonamide alcohol (D1, 1.0 equiv.) in MeOH or EtOH (0.1 M) was added 3.0 M NaOH (12.0-15.0 equiv.) and stirred at ambient temperature until complete. Once complete, the mixture was concentrated in vacuo without heating to half of the volume and then diluted with diethyl ether (25 mL/g of alcohol). The organic layer was separated and aqueous layer was washed with diethyl ether (25 mL/g of alcohol). The combined organics were dried over $MgSO_4$ and concentrated in vacuo and the residue purified by column chromatography to furnish the N-boc-N-tert-butyl protected sulfonamide (D2).

General Procedure Q: Esterification of Acid

Triethylorthoformate (5-10 mL/1 g of acid) and $H_2SO_4$ (~2 drops/1 g of acid) were added to a solution of acid (A6) in anhydrous ethanol (0.1) and reaction mixture was gently refluxed under am inert atmosphere (nitrogen or argon) till complete. Upon completion, the reaction mixture was concentrated to ⅓ of the reaction volume, poured in ice-water mixture and extracted with diethyl ether. The combined organic layer was washed with saturated $NaHCO_3$ solution, separated, dried over $MgSO_4$ and concentrated in vacuo to offer required ester (A5) as pale yellow oil that was used without further purification or passed through small silica gel column eluting with 10% EtOAc in hexane.

General Procedure R: Removal of N-Protecting Groups from Final Compounds

To a solution of N-boc-N-tert-butyl protected sulfonamide (D6, D3 or D9) in anhydrous DCM (10-20 mL/1 g of sulfonamide) at cooled to 0° C. was added TFA (2.5-5 mL/1 g of sulfonamide) and reaction mixture allowed to warm to room temperature and stirred for 2-5 h. The solvent were removed under vacuum and the crude was redissolved in DCM (20 mL/1 g of sulfonamide) and washed with saturated $NaHCO_3$ solution, water and brine, dried over $MgSO_4$ and concentrated in vacuo. The crude material was further purified by column chromatography or recrystallization from different organic solvents.

General Procedure S: Thioester Formation

In a sealed tube, CuI (0.1 equiv.) was added to an argon degased mixture of the iodoaryl (E1) (1.0 equiv.), thiobenzoic acid (1.0 equiv.), 1,10-phenanthroline (0.2 equiv.), N,N-diisopropylethylamine (2.0 equiv.) in toluene (0.15-0.20 M). The tube was sealed and stirred for 18 h at 110° C. After cooling to room temperature, the mixture was directly adsorbed on silica gel and purified by flash chromatography (SiO$_2$, cyclohexane/EtOAc, 1:0 to 8:2) to furnish the pure thioester (E2).

General Procedure T: Saponification of the Thioesters E2

An aqueous solution of NaOH 1N (3.0 equiv.) was added to a mixture of thioester (E2) (1.0 equiv.) in ethanol (0.15-0.20 M). The mixture was stirred for 18 h at room temperature before being concentrated in vacuo. The residue was dissolved in EtOAc and the organic layer was washed with an aqueous solution of 1.0N HCl, water, brine, dried over MgSO$_4$, and concentrated in vacuo. The crude mixture was purified by flash chromatography (SiO$_2$, cyclohexane/EtOAc, 1:0 to 9:1) to furnish the pure thiol (E3).

General Procedure U: Disulfide Formation

Under argon atmosphere, a solution of I$_2$ (1.4 equiv.) in ethanol (0.55 M) was added to a mixture of thiol (E3) (1.0 equiv.) in ethanol (0.40 M). After a dropwise addition, the mixture was stirred for 10 min at room temperature before being washed with an aqueous solution of Na$_2$S$_2$O$_3$ 10% until the mixture became clear. The ethanol was the removed in vacuo, the colorless mixture was extracted with EtOAc and the combined organic layers were washed with brine, dried over MgSO$_4$, and concentrated in vacuo to furnish the pure disulfide (E4).

General Procedure V: Sulfide Formation

Under argon atmosphere, to a solution of the alcohol (D2) (1.0 equiv.) in dry pyridine (0.20 M) were added the disulfide (E4) (2.0 to 3.0 equiv.) and tri-n-butylphosphine (2.0 to 3.0 equiv.). After being stirred at room temperature for 18 h, the reaction mixture was diluted with Et$_2$O, washed successively with an aqueous solution of NaOH 10%, HCl 10% and NaHCO$_3$ saturated, and dried over MgSO$_4$. Removal of the solvent gave a crude oil, which was purified by flash chromatography (SiO$_2$, cyclohexane/EtOAc, 1:0 to 9:1) to furnish the pure sulfide (E5).

General Procedure W: Removal of N-Protecting Groups from Sulfides

Under argon atmosphere, to a solution of the protected sulfonamide (E5) (1.0 equiv.) in dichloromethane (0.30 M) at 0° C. was added dropwise TFA (15.0 equiv.). The mixture was stirred for 18 h at room temperature before being directly absorbed on silica gel and purified by flash chromatography (SiO$_2$, cyclohexane/EtOAc, 1:0 to 7:3) to furnish the pure sulfonamide (E6).

Intermediate A: ±trans ethyl 2,2-dimethyl-3-phenylcyclopropanecarboxylate

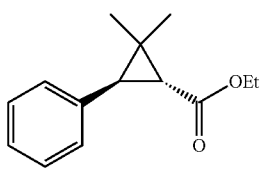 [SMILES: CCOC(=O)[C@@H]1[C@@H](c2ccccc2)C1(C)C]

Isopropyltriphenylphosphonium iodide (21.6 g, 50 mmol) and ethyl cinnamate (8.81 g, 50 mmol) were reacted as described under General Procedure A to furnish the title compound (6.58 g, 60%) as a colourless oil. ESIMS m/z [M+H]$^+$ 219.3.

Intermediate B: ±trans ethyl-2,2-dimethyl-3-(4-sulfamoylphenyl)cyclopropane-carboxylate

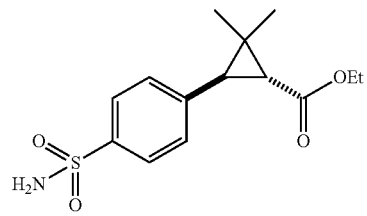

Intermediate A (1.55 g, 7.10 mmol) was reacted as described under General Procedure C followed by General Procedure D utilising ammonia in water to furnish the title compound which was purified by column chromatography (30% EtOAc/hexane→100% EtOAc) to give the title compound as a white solid (1.12 g, 53%). ESIMS m/z [M+NH$_4$]$^+$ 315.2.

Intermediate C: ±trans 4-[3-(hydroxymethyl)-2,2-dimethylcyclopropyl]benzene-sulfonamide

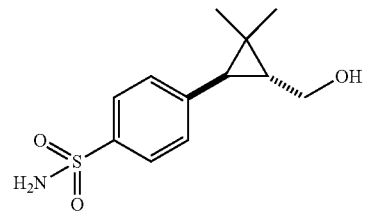

Intermediate B (1.07 g, 3.60 mmol) was reacted as described under General Procedure E to furnish the title compound as a white solid (742 mg, 81%) after column chromatography (80% EtOAc/hexane). ESIMS m/z [M+NH$_4$]$^+$273.2.

Intermediate D: ±trans ethyl 2-phenylspiro[2.4]heptane-1-carboxylate

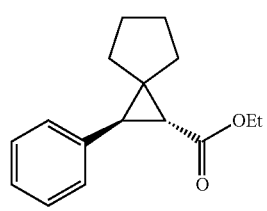 [SMILES: CCOC(=O)[C@@H]1[C@@H](c2ccccc2)C12CCCC2]

Cyclopentyltriphenylphosphonium bromide (10.3 g, 25 mmol) and ethyl cinnamate (4.40 g, 25 mmol) were reacted as described under General Procedure A to furnish the title compound (3.72 g, 61%) as a colorless oil. $^1$H NMR (300 MHz, CDCl$_3$) δ 7.32-7.11 (m, 5H), 4.22-4.13 (m, 2H), 2.77 (d, J=5.7 Hz, 1H), 2.15 (d, J=5.7 Hz, 1H), 1.91-1.85 (m, 2H), 1.72-1.27 (m, 9H).

Intermediate E: ±trans ethyl-2-(4-sulfamoylphenyl)spiro[2.4]heptane-1-carboxylate

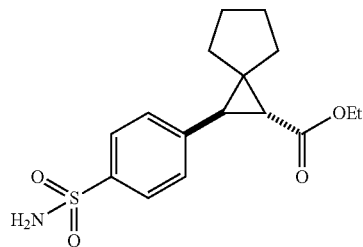

Intermediate D (3.5 g, 14.3 mmol) was reacted as described under General Procedure C followed by General Procedure D utilising ammonia in water to furnish the title compound (1.5 g, 33%) as a white solid after column chromatography. $^1$H NMR (300 MHz, CDCl$_3$) δ 7.87-7.82 (m, 2H), 7.26-7.23 (m, 2H), 4.88 (br s, 2H), 4.22-4.14 (m, 2H), 2.80-2.78 (m, 1H), 2.22-2.19 (m, 1H), 1.91-1.84 (m, 2H), 1.74-1.40 (m, 5H), 1.32-1.23 (m, 4H).

Intermediate F: ±trans 4-[2-(hydroxymethyl)spiro[2.4]hept-1-yl]benzenesulfonamide

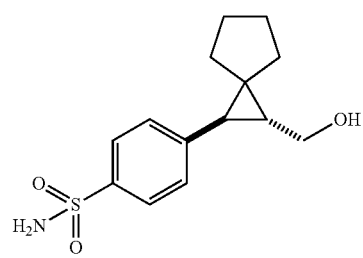

Intermediate E (1.5 g, 4.6 mmol) was reacted as described under General Procedure E to furnish the title compound as a white solid (1.01 g, 77%) which was used crude in the next step. $^1$H NMR (300 MHz, CDCl$_3$) δ 7.82-7.79 (m, 2H), 7.21-7.19 (m, 2H), 4.85 (br s, 2H), 3.87-3.81 (m, 1H), 3.75-3.68 (m, 1H), 3.48 (s, 1H), 1.90-1.20 (m, 10H).

Intermediate G: ±trans 4-(3-formyl-2,2-dimethylcyclopropyl)benzenesulfonamide

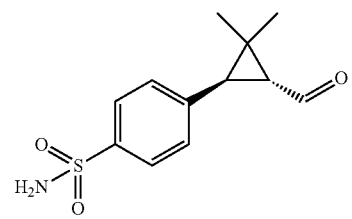 [SMILES: CC1(C)[C@H](C=O)[C@H]1c1ccc(S(N)(=O)=O)cc1]

Intermediate C (560 mg, 2.2 mmol) was reacted as described under General Procedure K to give the title compound which was purified by column chromatography (100% cyclohexane→60% EtOAc/cyclohexane) to furnish a colorless oil (409 mg, 73%). $^1$H NMR (300 MHz, CDCl$_3$) δ 9.63 (d, 1H), 7.87-7.84 (m, 2H), 7.33-7.30 (m, 2H), 5.00 (br s, 2H), 2.97 (d, 1H), 2.26 (dd, 1H), 1.44 (s, 3H), 0.98 (s, 3H).

Intermediate H: ±trans 4-[2-formylspiro[2.4]hept-1-yl]benzenesulfonamide

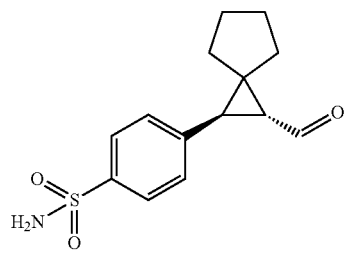 [SMILES: NS(=O)(=O)c1ccc([C@@H]2[C@@H](C=O)C23CCCC3)cc1]

Intermediate F (900 mg, 3.2 mmol) was reacted was reacted as described under General Procedure K to give the title compound which was purified by column chromatography (100% cyclohexane→60% EtOAc/cyclohexane) to furnish a colourless oil (701 mg, 78%). $^1$H NMR (300 MHz, CDCl$_3$) δ 9.51-9.49 (m, 1H), 7.87-7.84 (m, 2H), 7.26-7.23 (m, 2H), 5.03 (brs, 2H), 3.00-2.97 (m, 1H), 2.46-2.42 (m, 1H), 2.01-1.25 (m, 8H).

Intermediate I: (5-chloro-2-methoxybenzyl)(triphenyl)phosphonium bromide

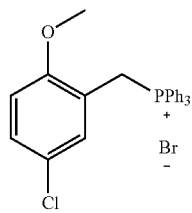

5-chloro-2-methoxybenzenemethanol (2.8 g, 16.2 mmol) and triphenylphosphine-hydrobromide (5.6 g, 16.2 mmol) were combined in toluene (50 ml) and heated to 80° C. overnight. The mixture was then cooled and the solid precipitate filtered off and washed with toluene to yield the titled compound (5.5 g, 66%) as a colourless solid.

Intermediate J: 4-{2-[(E/Z)-2-(5-chloro-2-methoxyphenyl)ethenyl]spiro[2.4]hept-1-yl}benzenesulfonamide

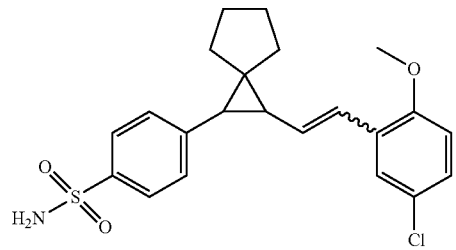 [SMILES: COc1ccc(Cl)cc1C=CC1C(c2ccc(S(N)(=O)=O)cc2)C12CCCC2]

Intermediate H (315 mg, 1.13 mmol) and Intermediate I (1.12 g, 2.25 mmol) were reacted as described under General Procedure L to furnish the title compound, which was purified by column chromatography (1:1 cyclohexame:ethyl acetate) to yield (120 mg, 26%) as a white solid. ESIMS m/z [M+Na]$^+$ 440.1.

Intermediate K: ±trans 2,2-dimethyl-3-phenylcyclopropanecarboxylic acid

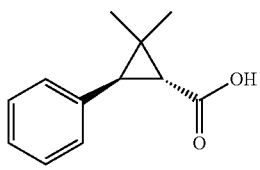

Intermediate A (6.58 g, 30.1 mmol) was reacted as described under General Procedure B to furnish the title compound (5.15 g, 90%) as a white solid. ESIMS m/z [M−H]$^-$ 189.2.

Intermediate L and M: (+)(R,R)-2,2-dimethyl-3-phenylcyclopropane-1-carboxylic acid and (−)(S,S)-2,2-dimethyl-3-phenylcyclopropane-1-carboxylic acid Intermediate L Intermediate M

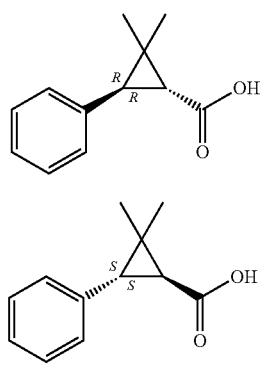

Intermediate K was separated into constituent enantiomers (Intermediate L and M) using SFC (Lux C4, CO$_2$/Methanol 17:3, 3 mLmin-1, 35° C., 100 bar), Intermediate L was the first eluting isomer (R,R) Rt=2.36 min, 100% ee, [α]$_D^{25.0}$+27.725°)(MeOH, c=1.020), and Intermediate M the second eluting isomer (S,S), Rt=3.01 min, 98.17% ee, [α]$_D^{26.1}$−27.800° (MeOH, c=1.000). Absolute stereochemistry assigned by x-ray crystallography.

Intermediate N: (1S,3S)-3-(4-bromophenyl)-2,2-dimethylcyclopropanecarboxylic acid

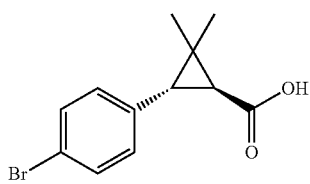

Intermediate M (2.4 g, 5.26 mmol) was reacted as described under General Procedure F to furnish the title compound as a white solid (1.942 g, 57%) after successive recrystalisations (Et$_2$O/hexane). $^1$H NMR (500 MHz, CDCl$_3$) δ 7.43-7.39 (m, 2H), 7.06-7.03 (m, 2H), 2.69-2.65 (m, 1H), 1.95-1.91 (m, 1H), 1.42 (s, 3H), 0.94 (s, 3H).

Intermediate O: [(1S,3S)-3-(4-bromophenyl)-2,2-dimethylcyclopropyl]methanol

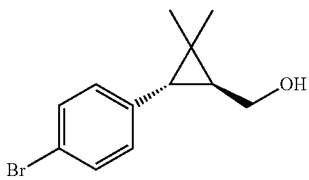

Intermediate N (1.234 g, 4.59 mmol) was reacted as described under General Procedure G to furnish the title compound (1.055 g, 90%) as brown oil after purification by column chromatography on silica (2.5% ethyl acetate in DCM). $^1$H NMR (500 MHz, CDCl$_3$) δ 7.39-7.36 (m, 2H), 7.05-7.01 (m, 2H), 3.90-3.86 (m, 1H), 3.72-3.69 (m, 1H), 1.71-1.69 (m, 1H), 1.44-1.37 (m, 1H), 1.28 (s, 3H), 0.84 (s, 3H).

Intermediate P: 2-{[(1S,3S)-3-(4-bromophenyl)-2,2-dimethylcyclopropyl]methoxy}-4-chloro-1-methoxybenzene

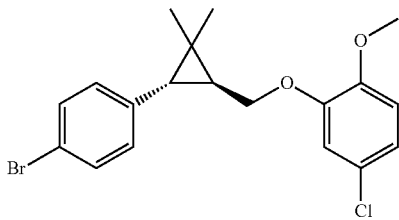 [SMILES: COc1ccc(Cl)cc1OC[C@H]1[C@H](c2ccc(Br)cc2)C1(C)C]

Intermediate O (160 mg, 0.63 mmol) and 5-chloro-2-methoxyphenol (120 mg, 0.76 mmol) were reacted as described under General Procedure H to furnish the title compound as a colourless oil (188 mg, 76%) after purification by preparative TLC (20% DCM in hexane). $^1$H NMR (500 MHz, CDCl$_3$) δ 7.39-7.37 (m, 2H), 7.04-7.03 (m, 2H), 6.92-6.89 (m, 2H), 6.80-6.78 (m, 2H), 4.26-4.22 (m, 1H), 4.11-4.07 (m, 1H), 3.84 (s, 3H), 1.81-1.80 (m, 1H), 1.58-1.54 (m, 1H), 1.26 (s, 3H), 0.86 (s, 3H).

Intermediate Q: 5-{[(1S,3S)-3-(4-bromophenyl)-2,2-dimethylcyclopropyl]methoxy}-2-methoxypyridine

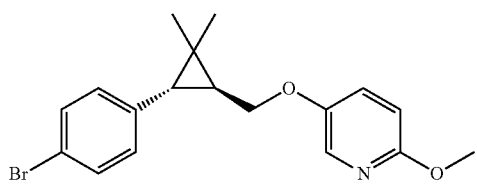 [SMILES: COc1ccc(OC[C@H]2[C@H](c3ccc(Br)cc3)C2(C)C)cn1]

Intermediate O (300 mg, 1.18 mmol) and 6-methoxypyridin-3-ol (176 mg, 1.40 mmol) were reacted as described under General Procedure H to furnish the title compound as a colourless oil (282 mg, 66%) after purification by column chromatography on silica (10% ethyl acetate in hexane). $^1$H NMR (500 MHz, CDCl$_3$) δ 7.85-7.83 (m, 1H), 7.40-7.38 (m, 2H), 7.26-7.24 (m, 1H), 7.06-7.02 (m, 2H), 6.69-6.68 (m, 1H), 4.23-4.19 (m, 1H), 4.01-3.97 (m, 1H), 3.90 (s, 3H), 1.81-1.80 (m, 1H), 1.54-1.50 (m, 1H), 1.27 (s, 3H), 0.86 (s, 3H).

Intermediate R: (1R,3R)-3-(4-bromophenyl)-2,2-dimethylcyclopropanecarboxylic acid

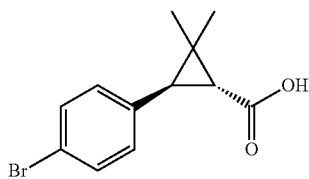

Intermediate L (5.0 g, 26.2 mmol) was reacted as described under General Procedure F to furnish the title compound (4.76 g, 67%) after successive recrystallizations (Et$_2$O/hexane). $^1$H NMR (500 MHz, CDCl$_3$) δ 7.43-7.39 (m, 2H), 7.06-7.03 (m, 2H), 2.69-2.65 (m, 1H), 1.95-1.91 (m, 1H), 1.42 (s, 3H), 0.94 (s, 3H).

Intermediate S: [(1R,3R)-3-(4-bromophenyl)-2,2-dimethylcyclopropyl]methanol

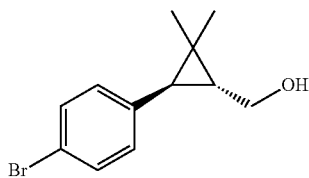

A solution of Intermediate R (3.5 g, 13.0 mmol), triethylorthoformate (6.5 ml, 39.0 mmol) and sulfuric acid (cat.) in ethanol were heated at reflux for 20 h. The reaction mixture was cooled to rt and was concentrated in vacuo. The residue was dissolved in EtOAc and water was added. The layers were separated and the aqueous was extracted with EtOAc. The organics were combined, washed with water and brine, dried of MgSO$_4$ and were concentrated in vacuo. Purification was achieved by filtration through a plug of silica, eluting with 5% EtOAc/hexane. The ester intermediate was reacted as described under General Procedure E to give the titled compound as colourless viscous oil (1.61 g, 52%). $^1$H NMR (500 MHz, CDCl$_3$) δ 7.39-7.36 (m, 2H), 7.05-7.01 (m, 2H), 3.90-3.86 (m, 1H), 3.72-3.69 (m, 1H), 1.71-1.69 (m, 1H), 1.44-1.37 (m, 1H), 1.28 (s, 3H), 0.84 (s, 3H).

Intermediate T: 5-{[(1R,3R)-3-(4-bromophenyl)-2,2-dimethylcyclopropyl]methoxy}-2-methoxypyridine

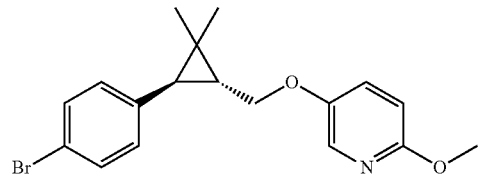 [SMILES: COc1ccc(OC[C@@H]2[C@@H](c3ccc(Br)cc3)C2(C)C)cn1]

Intermediate S (202 mg, 0.792 mmol) and 6-methoxypyridin-3-ol (119 mg, 0.950 mmol) were reacted as described under General Procedure H to furnish the title compound as a colourless oil (130 mg, 46%) after purification by flash chromatography on silica (80% DCM/hexane). $^1$H NMR (500 MHz, CDCl$_3$) δ 7.85-7.83 (m, 1H), 7.40-7.38 (m, 2H), 7.26-7.24 (m, 1H), 7.06-7.02 (m, 2H), 6.69-6.68 (m, 1H), 4.23-4.19 (m, 1H), 4.01-3.97 (m, 1H), 3.90 (s, 3H), 1.81-1.80 (m, 1H), 1.54-1.50 (m, 1H), 1.27 (s, 3H), 0.86 (s, 3H).

Intermediate U: 4-[(1R,3R)-3-(hydroxymethyl)-2,2-dimethylcyclopropyl]benzenesulfonamide

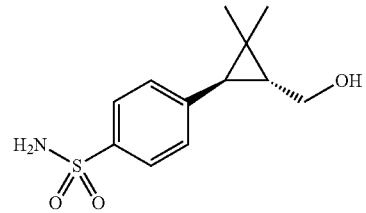 [SMILES: CC1(C)[C@H](CO)[C@H]1c1ccc(S(N)(=O)=O)cc1]

Enantio-pure Intermediate L was esterified following the General Procedure Q as pale-yellow oil (88%), that was converted to Intermediate U using the same steps (steps C, D and E) as described for its racemic analog Intermediate C as white solid. ESIMS m/z [M−H]$^-$ 254.0.

Intermediate V: 4-[(1S,3S)-3-(hydroxymethyl)-2,2-dimethylcyclopropyl]benzene-sulfonamide

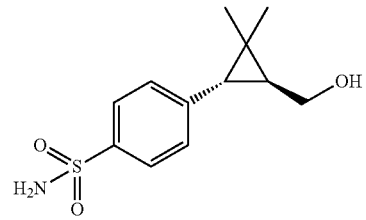 [SMILES: CC1(C)[C@@H](CO)[C@@H]1c1ccc(S(N)(=O)=O)cc1]

Enantio-pure Intermediate M (5.00 g, 26.3 mmol) was esterified following the General Procedure Q as pale-yellow oil (5.80 g, Quantitative). The ester (1.50 g, 6.87 mmol) was converted to Intermediate V, using the same steps (steps C, D and E) as described for its racemic analog Intermediate C, which was isolated as a white solid (805 mg, 46% over three steps) that did not require further purification. ESIMS m/z [M−H]$^-$ 254.1.

Intermediate W:
(1R,2S)-2-phenylcyclopropanecarboxylic acid and
Intermediate X:
(1S,2R)-2-phenylcyclopropanecarboxylic acid Intermediate W

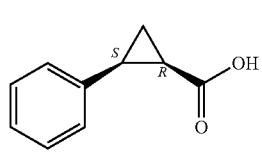

Intermediate X

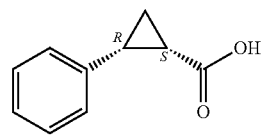

Commercially purchased ±cis-2-phenylcyclopropanecarboxylic acid was separated into constituent enantiomers (Intermediate W and Y) using SFC (Chiralpak AD-H, $CO_2$/Methanol 8:2, 3 mL/min, 100 bar), Intermediate W was the first eluting isomer at Rt 2.31 min and intermediate X was second eluting isomer at Rt 2.89 min. The stereochemistry of Intermediates W and X was arbitrarily assigned.

Intermediate Y:
(1R,2R)-2-phenylcyclopropanecarboxylic acid and
Intermediate Z:
(1S,2S)-2-phenylcyclopropanecarboxylic acid Intermediate Y

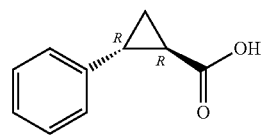

Intermediate Z

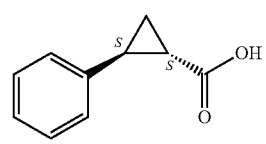

±trans-2-phenylcyclopropanecarboxylic acid was separated into constituent enantiomers (Intermediate Y and Z) using chiral SFC. Intermediate Y: $^1$HNMR (300 MHz, $CDCl_3$) δ $^1$HNMR (300 MHz, $CDCl_3$) δ 7.35-7.09 (m, 5H), 2.61 (ddd, 1H), 1.91 (dq, 1H), 1.67 (q, 1H), 1.42 (dq, 1H). ESIMS m/z $[M-H]^+$ 161.2. $[α]_D^{24.4}$–259.546 (c 0.119, MeOH). Absolute stereochemistry assigned by comparison with literature (JMC 2000, p3923; JMC 2011, p957).

Intermediate Z: $^1$HNMR (300 MHz, $CDCl_3$) δ 7.35-7.09 (m, 5H), 2.61 (ddd, 1H), 1.91 (dq, J=4.8, 3.9, 1H), 1.67 (q, 1H), 1.42 (dq, 1H). ESIMS m/z $[M-H]^+$ 161.2. $[α]_D^{24.5}$+249.261 (c 0.102, MeOH). Absolute stereochemistry assigned by comparison with literature (JMC 2000, p3923; JMC 2011, p957).

Intermediate AA: 4-[(1S,2R)-2-(hydroxymethyl)cyclopropyl]benzenesulfonamide

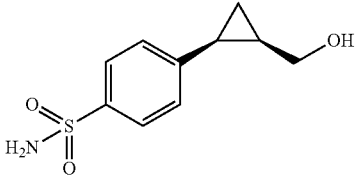 [SMILES: NS(=O)(=O)c1ccc([C@H]2C[C@H]2CO)cc1]

Intermediate W (3.01 g, 18.5 mmol) was converted to Intermediate AA using the general procedures Q, C, D and E to give the title compound as a white solid (1.52 g, 36% over 4 steps). ESIMS m/z $[M-H]^-$ 226.0.

Intermediate AB: 4-[(1R,2R)-2-(hydroxymethyl)cyclopropyl]benzenesulfonamide

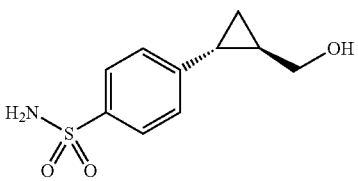 [SMILES: NS(=O)(=O)c1ccc([C@@H]2C[C@H]2CO)cc1]

Enantio-pure Intermediate Y was esterified following the General Procedure Q as pale-yellow oil (quantitative), that was converted to Intermediate AB using the same steps as described for Intermediate C (steps C, D and E), and isolated as a white solid (60% over the three steps). $^1$H NMR (500 MHz, DMSO-$d_6$) δ 7.67 (d, 2H), 7.22-7.24 (m, 4H), 4.63 (t, 1H), 3.51-3.46 (m, 1H), 3.37-3.32 (m, 1H), 1.90-1.86 (m, 1H), 1.37-1.33 (m, 1H), 0.98-0.91 (m, 2H).

Intermediate AC: 4-[(1S,2S)-2-(hydroxymethyl)cyclopropyl]benzenesulfonamide

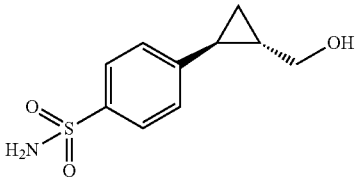 [SMILES: NS(=O)(=O)c1ccc([C@H]2C[C@@H]2CO)cc1]

Enantio-pure Intermediate Z (10.0 g, 61.6 mmol) was esterified following the General Procedure Q as pale-yellow oil (11.7 g, Quantitative). The ester (5.0 g, 26.3 mmol) was converted to Intermediate AC, using the same steps (steps C, D and E) as described for Intermediate C, and isolated as a white solid (1.55 g, 26% over three steps) that did not require further purification. $^1$H NMR (300 MHz, DMSO-$d_6$) δ 7.71-7.70 (m, 2H), 7.29-7.26 (m, 4H), 4.68 (t, 1H), 3.54-3.50 (m, 1H), 3.42-3.36 (m, 1H), 1.94-1.90 (m, 1H), 1.41-1.37 (m, 1H), 1.02-0.98 (m, 2H).

Intermediate AD: tert-butyl tert-butyl({4-[(1R,3R)-3-(hydroxymethyl)-2,2-dimethylcyclopropyl]phenyl}-sulfonyl)carbamate

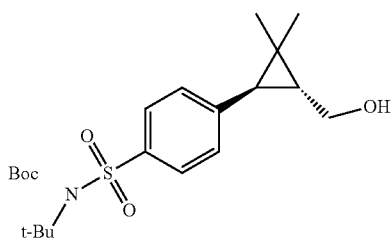 [SMILES: CC(C)(C)NS(=O)(=O)c1ccc([C@@H]2[C@@H](CO)C2(C)C)cc1 ; "Boc"]

Intermediate AK (3.0 g, 5.40 mmol) was reacted as described under General Procedure P to furnish the title compound (2.2 g, 89%) as a colorless oil. $^1$H NMR (300 MHz, CDCl$_3$) δ 7.92 (d, 2H), 7.24 (d, 2H), 3.91-3.68 (m, 2H), 1.79 (d, 1H), 1.49 (s, 9H), 1.46 (s, 9H), 1.47-1.44 (m, 1H), 1.29 (s, 3H), 0.83 (s, 3H).

Intermediate AE tert-butyl tert-butyl({4-[(1S,3S)-3-(hydroxymethyl)-2,2-dimethylcyclopropyl]phenyl}-sulfonyl)-carbamate

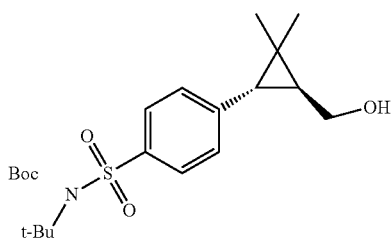 [SMILES: CC(C)(C)NS(=O)(=O)c1ccc([C@H]2[C@H](CO)C2(C)C)cc1 ; "Boc"]

Intermediate AJ (2.4 g, 4.32 mmol) was reacted as described under General Procedure P to furnish the title compound (1.6 g, 82%) as a colorless oil. $^1$H NMR (300 MHz, CDCl$_3$) δ 7.91 (d, 2H), 7.24 (d, 2H), 3.91-3.68 (m, 2H), 1.79 (d, J=5.8 Hz, 1H), 1.49 (s, 9H), 1.45 (s, 9H), 1.45-1.42 (m, 1H), 1.29 (s, 3H), 0.83 (s, 3H).

Intermediate AF: tert-butyl tert-butyl({4-[(1S,2S)-2-(hydroxymethyl)cyclopropyl]phenyl}sulfonyl)carbamate

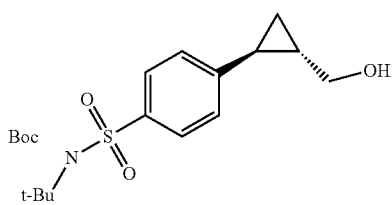 [SMILES: CC(C)(C)NS(=O)(=O)c1ccc([C@H]2C[C@@H]2CO)cc1 ; "Boc"]

Intermediate AC (519 mg, 2.28 mmol) was reacted with di-tert-butyl dicarbonate as described under General Procedure O to furnish the tri-boc protected compound as a colorless oil, which was further hydrolyzed according to General Procedure P to furnish the title compound as colorless oil (497 mg, 51% over 2 steps). $^1$H NMR (300 MHz, CDCl$_3$) δ 7.92-7.91 (m, 2H), 7.15-7.13 (m, 2H), 3.69-3.62 (m, 2H), 1.92-1.88 (m, 1H), 1.52 (s, 9H), 1.47 (s, 9H), 1.43-1.41 (m, 1H), 1.08-1.04 (m, 2H).

Intermediate AG: tert-butyl tert-butyl({4-[(1R,3R)-3-formyl-2,2-dimethylcyclopropyl]-phenyl}sulfonyl)-carbamate

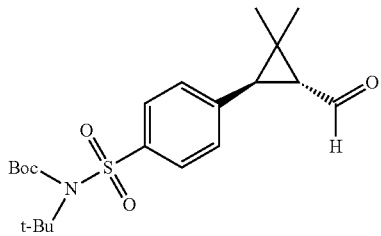 [SMILES: CC(C)(C)OC(=O)N(C(C)(C)C)S(=O)(=O)c1ccc([C@@H]2[C@@H](C=O)C2(C)C)cc1]

Intermediate AD (220 mg, 0.48 mmol) was reacted with PCC (291 mg, 1.35 mmol) as described under General Procedure K by eluting the reaction mixture through pad of silica gel topped up with celite with 5% EtOAc in DCM to give the title compound as colorless oil (198 mg, 90%). $^1$H NMR (500 MHz CDCl$_3$) δ 9.64 (s, 1H), 7.98 (d, 2H), 7.28 (d, 2H), 2.97-2.98 (m, 1H), 2.28-2.26 (m, 1H), 1.51 (s, 9H), 1.47 (s, 9H), 1.45 (s, 3H), 0.98 (s, 1H).

Intermediate AH: tert-butyl tert-butyl[(4-{(1R,3R)-3-[(E/Z)-2-(5-chloro-2-methoxyphenyl)ethenyl]-2,2-dimethylcyclopropyl}phenyl)sulfonyl]carbamate

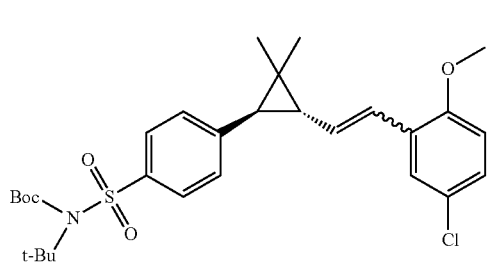 [SMILES: COc1ccc(Cl)cc1C=C[C@@H]1[C@@H](c2ccc(S(=O)(=O)N(C(=O)OC(C)(C)C)C(C)(C)C)cc2)C1(C)C]

Intermediate AG (198 mg, 0.44 mmol) and Intermediate I (263 mg, 0.53 mmol) were reacted as described under General Procedure L to furnish the title compound, which was purified by silica gel column chromatography (0%→4% EtOAc in hexane) to yield (195 mg, 75%) as colourless gum. $^1$H NMR (500 MHz CDCl$_3$) δ 7.95-7.92 (m, 2H), 7.36-7.12 (m, 4H), 6.85-6.78 (m, 1.5H), 6.62 (d, 0.5H), 6.14-6.09 (m, 0.5H), 5.67-5.63 (m, 0.5H), 3.84 (d, 3H), 2.14-1.99 (m, 2H), 1.51-1.46 (m, 18H), 1.32 (d, 3H), 0.91 (s, 3H).

Intermediate AI: 4-{(1R,3R)-3-[(E/Z)-2-(5-chloro-2-methoxyphenyl)ethenyl]-2,2-dimethylcyclopropyl}benzenesulfonamide

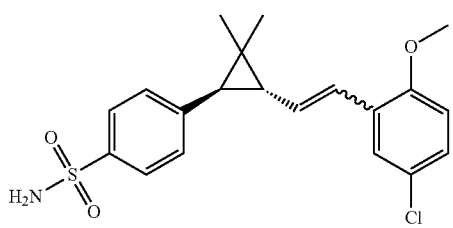 [SMILES: COc1ccc(Cl)cc1C=C[C@@H]1[C@@H](c2ccc(S(N)(=O)=O)cc2)C1(C)C]

Intermediate AH (165 mg, 0.28 mmol) was treated with TFA (1.5 mL) as described under General Procedure R to furnish the title compound (82 mg, 75%) as colourless gum after purification by silica gel column chromatography (10%→30% EtOAc in DCM. ESIMS m/z [M+H]+ 390.0

Intermediate AJ: [(1S,3S)-3-{4-[(tert-butoxycarbonyl)(tert-butyl)sulfamoyl]phenyl}-2,2-dimethylcyclopropyl]methyl tert-butyl carbonate

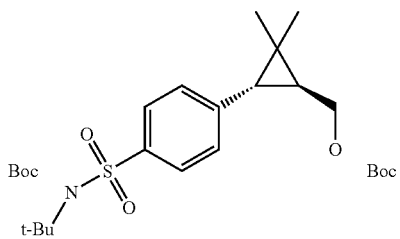 [SMILES: CC(C)(C)NS(=O)(=O)c1ccc([C@H]2[C@H](CO)C2(C)C)cc1 ; "Boc" ; "Boc"]

Intermediate V (1.4 g, 5.48 mmol) was reacted as described under General Procedure O to furnish the title compound (2.4 g, 79%) as a colorless oil.
¹H NMR (300 MHz, CDCl₃) δ 7.90 (d, 2H), 7.24 (d, 2H), 4.33-4.12 (m, 2H), 1.87 (d, 1H), 1.49 (s, 9H), 1.48 (s, 9H), 1.45 (s, 9H), 1.42-1.35 (m, 1H), 1.28 (s, 3H), 0.82 (s, 3H).

Intermediate AK: [(1R,3R)-3-{4-[(tert-butoxycarbonyl)(tert-butyl)sulfamoyl]phenyl}-2,2-dimethylcyclopropyl]methyl tert-butyl carbonate

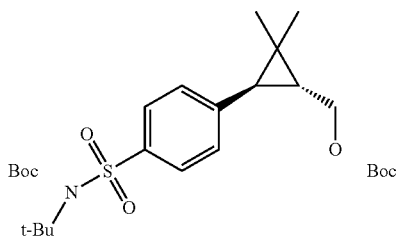 [SMILES: CC(C)(C)NS(=O)(=O)c1ccc([C@@H]2[C@@H](CO)C2(C)C)cc1 ; "Boc" ; "Boc"]

Intermediate U (1.8 g, 7.04 mmol) was reacted as described under General Procedure O to furnish the title compound (3.0 g, 77%) as a colorless oil.
¹H NMR (300 MHz, CDCl₃) δ 7.92 (d, 2H), 7.24 (d, 2H), 4.34-4.12 (m, 2H), 1.88 (d, 1H), 1.50 (s, 9H), 1.49 (s, 9H), 1.46 (s, 9H), 1.43-1.36 (m, 1H), 1.29 (s, 3H), 0.83 (s, 3H).

Intermediate AL: Thiobenzoic acid S-(5-chloro-2-methoxy-phenyl) ester

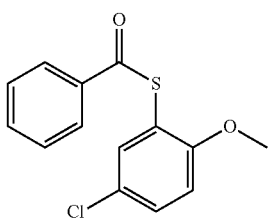 [SMILES: COc1ccc(Cl)cc1SC(=O)c1ccccc1]

4-Chloro-2-iodoanisole (2.0 g, 7.45 mmol) was reacted as described under General Procedure C to furnish the title compound (2.0 g, 96%) as an orange oil.
¹H NMR (300 MHz, CDCl₃) δ 8.05-8.01 (m, 2H), 7.64-7.58 (m, 1H), 7.53-7.46 (m, 3H), 7.40 (dd, 1H), 6.93 (d, 1H), 3.84 (s, 3H).

Intermediate AM: 5-Chloro-2-methoxy-benzenethiol

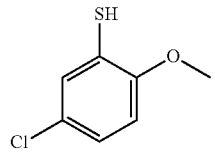

Intermediate AL (2.0 g, 7.17 mmol) was reacted as described under General Procedure D to furnish the title compound (770 mg, 61%) as a colorless oil.
¹H NMR (300 MHz, CDCl₃) δ 7.23 (d, 2H), 7.06 (dd, 1H), 6.75 (d, 1H), 3.87 (s, 3H), 3.86 (bs, 1H).

Intermediate AN: bis-(5-Chloro-2-methoxy-phenyl)-disulfide

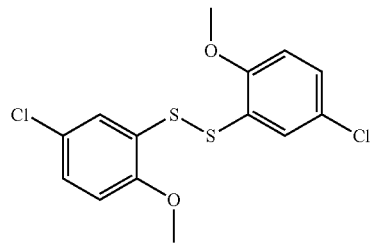 [SMILES: COc1ccc(Cl)cc1SSc1cc(Cl)ccc1OC]

Intermediate AM (770 mg, 4.41 mmol) was reacted as described under General Procedure E to furnish the title compound (765 mg, Quant.) as a yellow oil.
¹H NMR (300 MHz, CDCl₃) δ 7.23 (d, 2H), 7.06 (dd, 1H), 6.75 (d, 1H), 3.87 (s, 3H).

Intermediate AO: tert-butyl tert-butyl({4-[(1S,3S)-3-{[(5-chloro-2-methoxyphenyl)sulfanyl]methyl}-2,2-dimethylcyclopropyl]phenyl}sulfonyl)carbamate

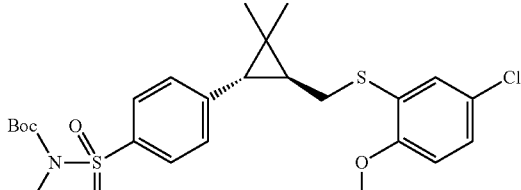

Intermediate AN (820 mg, 2.36 mmol) and Intermediate AE (500 mg, 1.10 mmol) were reacted as described under General Procedure F to furnish the title compound (640 mg, 95%) as a colorless oil.
¹H NMR (300 MHz, CDCl₃) δ 7.90 (d, 2H), 7.23 (d, 1H), 7.19 (d, 2H), 7.11 (dd, 1H), 6.75 (d, 1H), 3.87 (s, 3H), 3.17-2.99 (m, 2H), 1.78 (d, 1H), 1.50 (s, 9H), 1.47 (s, 9H), 1.42-1.35 (m, 1H), 1.26 (s, 3H), 0.80 (s, 3H).

Intermediate AP: tert-butyl tert-butyl({4-[(1R,3R)-3-{[(5-chloro-2-methoxyphenyl)sulfanyl]methyl}-2,2-dimethylcyclopropyl]phenyl}sulfonyl)carbamate

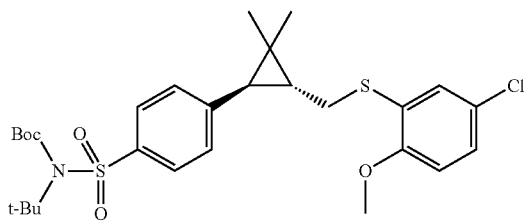 [SMILES: COc1ccc(Cl)cc1SC[C@@H]1[C@@H](c2ccc(S(=O)(=O)N(C(=O)OC(C)(C)C)C(C)(C)C)cc2)C1(C)C]

Intermediate AN (820 mg, 2.36 mmol) and Intermediate AD (540 mg, 1.18 mmol) were reacted as described under General Procedure F to furnish the title compound (540 mg, 75%) as a colorless oil.
$^1$H NMR (300 MHz, CDCl$_3$) δ 7.90 (d, 2H), 7.23 (d, 1H), 7.19 (d, 2H), 7.11 (dd, 1H), 6.75 (d, 1H), 3.87 (s, 3H), 3.17-2.99 (m, 2H), 1.78 (d, 1H), 1.51 (s, 9H), 1.47 (s, 9H), 1.42-1.35 (m, 1H), 1.26 (s, 3H), 0.80 (s, 3H).

Intermediate AQ: bis-(4-Methyl-phenyl)-disulfide

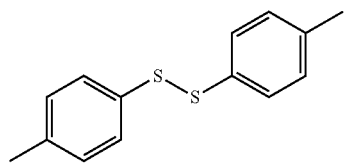

p-toluenethiol (1.0 g, 8.05 mmol) was reacted as described under General Procedure E to furnish the title compound (990 mg, Quant.) as a colorless oil. $^1$H NMR (300 MHz, CDCl$_3$) δ 7.38 (d, 2H), 7.11 (d, 2H), 2.32 (s, 3H).

Intermediate AR: tert-butyl tert-butyl({4-[(1S,3S)-2,2-dimethyl-3-{[(4-methylphenyl)sulfanyl]methyl}cyclopropyl]phenyl}sulfonyl)carbamate

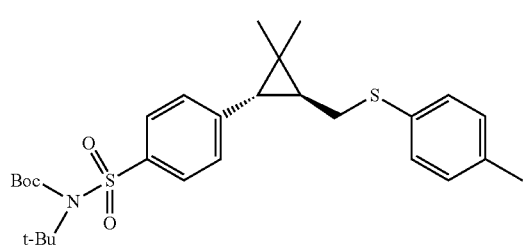 [SMILES: Cc1ccc(SC[C@H]2[C@H](c3ccc(S(=O)(=O)N(C(=O)OC(C)(C)C)C(C)(C)C)cc3)C2(C)C)cc1]

Intermediate AQ (815 mg, 3.3 mmol) and Intermediate AE (500 mg, 1.1 mmol) were reacted as described under General Procedure F to furnish the title compound (500 mg, 81%) as a colorless oil.
$^1$H NMR (300 MHz, CDCl$_3$) δ 7.89 (d, 2H), 7.30 (d, 2H), 7.17 (d, 2H), 7.08 (d, 2H), 3.17-2.95 (m, 2H), 2.31 (s, 3H), 1.72 (d, 1H), 1.50 (s, 9H), 1.47 (s, 9H), 1.40-1.37 (m, 1H), 1.20 (s, 3H), 0.77 (s, 3H).

Intermediate AS: tert-butyl tert-butyl({4-[(1R,3R)-2,2-dimethyl-3-{[(4-methylphenyl)sulfanyl]methyl}cyclopropyl]phenyl}sulfonyl)carbamate

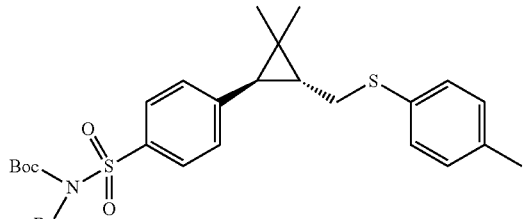

Intermediate AQ (320 mg, 1.32 mmol) and Intermediate AD (200 mg, 0.44 mmol) were reacted as described under General Procedure F to furnish the title compound (190 mg, 77%) as a colorless oil.
$^1$H NMR (300 MHz, CDCl$_3$) δ 7.87 (d, 2H), 7.28 (d, 2H), 7.15 (d, 2H), 7.07 (d, 2H), 3.15-2.94 (m, 2H), 2.30 (s, 3H), 1.81 (m, 1H), 1.48 (s, 9H), 1.45 (s, 9H), 1.45-1.40 (m, 1H), 1.19 (s, 3H), 0.76 (s, 3H).

Intermediate AT: 1-{[(1S,3S)-3-(4-bromophenyl)-2,2-dimethylcyclopropyl]methoxy}-4-fluoro-2-methoxybenzene

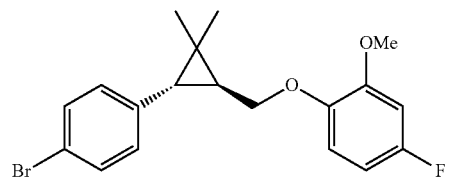 [SMILES: COc1cc(F)ccc1OC[C@H]1[C@H](c2ccc(Br)cc2)C1(C)C]

Intermediate O (250 mg, 0.98 mmol), 4-fluoro-2-methoxyphenol (0.13 mL, 1.2 mmol), TPP (282 mg, 1.1 mmol) and DIAD (0.21 mL, 1.1 mmol) in toluene were reacted as described under General Procedure H to furnish the title compound as a colourless oil (231 mg, 62%) after purification by column chromatography (30% DCM in hexane). $^1$H NMR (500 MHz, CDCl$_3$) δ 7.39-7.36 (m, 2H), 7.04-7.01 (m, 2H), 6.90-6.86 (m, 1H), 6.65-6.62 (m, 1H), 6.59-6.55 (m, 1H), 4.25-4.21 (m, 1H), 4.08-4.03 (m, 1H), 3.83 (s, 3H), 1.77-1.76 (m, 1H), 1.56-1.51 (m, 1H), 1.23 (s, 3H), 0.84 (s, 3H).

Intermediate AU: 1-{[(1S,3S)-3-(4-bromophenyl)-2,2-dimethylcyclopropyl]methoxy}-4-chloro-2-methoxybenzene

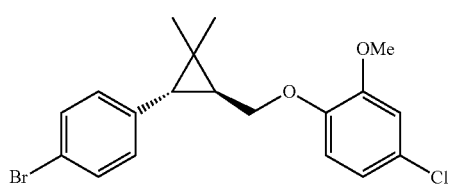 [SMILES: COc1cc(Cl)ccc1OC[C@H]1[C@H](c2ccc(Br)cc2)C1(C)C]

Intermediate O (250 mg, 0.98 mmol), 4-chloro-2-methoxyphenol (0.14 mL, 1.2 mmol), TPP (282 mg, 1.1 mmol) and DIAD (0.21 mL, 1.1 mmol) in toluene were reacted as described under General Procedure H to furnish the title compound as a colourless oil (268 mg, 69%) after purification by column chromatography (35% DCM in hexane). $^1$H NMR (500 MHz, CDCl$_3$) δ 7.39-7.36 (m, 2H), 7.05-7.01 (m, 2H), 6.96-6.79 (m, 3H), 4.26-4.22 (m, 1H), 4.10-4.06 (m, 1H), 3.84 (s, 3H), 1.79-1.78 (m, 1H), 1.57-1.52 (m, 1H), 1.25 (s, 3H), 0.86 (s, 3H).

Intermediate AV: 3-{[(1S,3S)-3-(4-bromophenyl)-2,2-dimethylcyclopropyl]methoxy}-2-methylpyridine

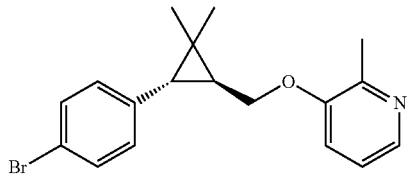 [SMILES: Cc1ncccc1OC[C@H]1[C@H](c2ccc(Br)cc2)C1(C)C]

Intermediate O (1.00 g, 3.9 mmol), 3-hydroxy-2-methylpyridine (513 mg, 4.7 mmol), TPP (1.33 g, 5.1 mmol) and DIAD (1.08 mL, 5.49 mmol) in toluene were reacted as described under General Procedure H to furnish the title compound as a colourless oil (561 mg, 41%) after purification by column chromatography on neutral alumina (10% EtOAc/hexane). $^1$H NMR (500 MHz, CDCl$_3$) δ 8.10-8-07 (m, 1H), 7.42-7.39 (m, 2H), 7.12-7-04 (m, 4H), 4.24-4.20 (m, 1H), 4.06-4.02 (m, 1H), 2.51 (s, 3H), 1.86-1.84 (m, 1H), 1.56-1.52 (m, 1H), 1.29 (s, 3H), 0.88 (s, 3H).

Intermediate AW: 5-{[(1S,3S)-3-(4-bromophenyl)-2,2-dimethylcyclopropyl]methoxy}-2-methylpyridine

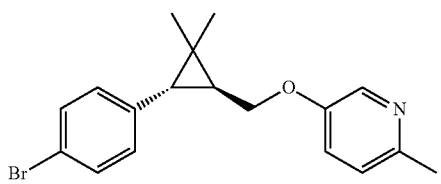 [SMILES: Cc1ccc(OC[C@H]2[C@H](c3ccc(Br)cc3)C2(C)C)cn1]

Intermediate O (1.00 g, 3.9 mmol), 5-hydroxy-2-methylpyridine (513 mg, 4.7 mmol), TPP (1.33 g, 5.1 mmol) and DIAD (1.08 mL, 5.49 mmol) in toluene were reacted as described under General Procedure H to furnish the title compound as a colourless oil (735 mg, 54%) after purification by column chromatography on neutral alumina (10% EtOAc/hexane). ESIMS m/z [M+H]$^+$ 346.1, 348.1.

Intermediate AX: tert-butyl ({4-[(1S,3S)-3-{[(6-methoxypyridin-3-yl)oxy]methyl}-2,2-dimethylcyclopropyl]phenyl}sulfamoyl)carbamate

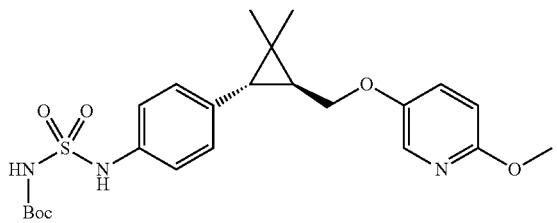 [SMILES: COc1ccc(OC[C@H]2[C@H](c3ccc(NS(=O)(=O)NC(=O)OC(C)(C)C)cc3)C2(C)C)cn1]

Intermediate Q (209 mg, 0.577 mmol) and tert-butylaminosulfonylcarbamate (136 mg, 0.692 mmol) were reacted as described under General Procedure I to furnish the title compound as a (16 mg, 6%) after purification by column chromatography (30% EtOAc/hexane) followed by preparative TLC (20%→30% EtOAc/hexane). ESIMS m/z [M+H]$^+$ 478.2.

Intermediate AY: [(1S,3S)-3-(4-bromophenyl)-2,2-dimethylcyclopropyl]methyl 5-fluoro-2-methylphenyl ether

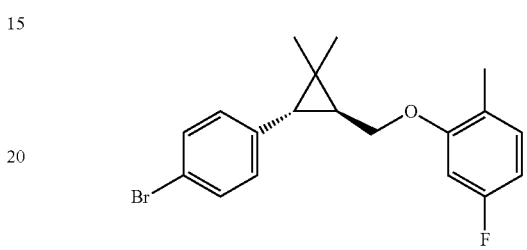

Intermediate O (500 mg, 2.0 mmol), 5-fluoro-2-methylphenol (297 mg, 2.4 mmol), TPP (668 mg, 2.5 mmol) and DIAD (0.54 mL, 2.74 mmol) in THF were reacted as described under General Procedure H to furnish the title compound as a colourless oil (529 mg, 74%) after purification by column chromatography on silica (10% DCM/hexane). $^1$H NMR (500 MHz, CDCl$_3$) δ 7.45-7.38 (m, 2H), 7.09-7.04 (m, 3H), 6.61-6.53 (m, 2H), 4.19-4.15 (m, 1H), 4.03-3.99 (m, 1H), 2.19 (s, 3H), 1.85-1.84 (m, 1H), 1.54-1.51 (m, 1H), 1.28 (s, 3H), 0.88 (s, 3H).

Intermediate AZ: [(1S,3S)-3-(4-bromophenyl)-2,2-dimethylcyclopropyl]methyl 4-fluoro-2-methylphenyl ether

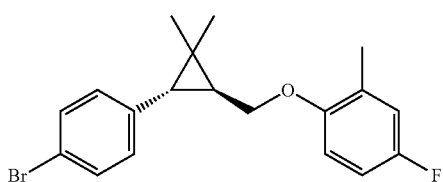 [SMILES: Cc1cc(F)ccc1OC[C@H]1[C@H](c2ccc(Br)cc2)C1(C)C]

Intermediate O (300 mg, 1.2 mmol), 4-fluoro-2-methylphenol (178 mg, 1.4 mmol), TPP (401 mg, 1.5 mmol) and DIAD (0.32 mL, 1.6 mmol) in toluene were reacted as described under General Procedure H to furnish the title compound as a colourless oil (248 mg, 58%) after purification by column chromatography on silica (2.5% EtOAc/hexane). $^1$H NMR (500 MHz, CDCl$_3$) δ 7.45-7.38 (m, 2H), 7.07-7.05 (m, 2H), 6.88-6.74 (m, 3H), 4.19-4.15 (m, 1H), 4.02-3.98 (m, 1H), 2.24 (s, 3H), 1.83-1.81 (m, 1H), 1.54-1.50 (m, 1H), 1.27 (s, 3H), 0.87 (s, 3H).

Intermediate BA: tert-butyl tert-butyl[(4-{(1S,2R)-2-[(E/Z)-2-(5-chloro-2-methoxyphenyl)ethenyl]cyclopropyl}phenyl)sulfonyl]carbamate

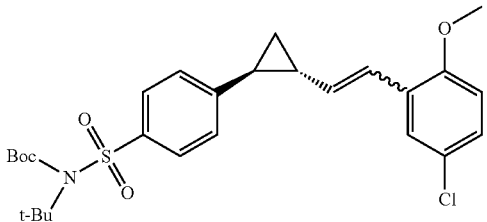 [SMILES: COc1ccc(Cl)cc1C=C[C@H]1C[C@@H]1c1ccc(S(=O)(=O)N(C(=O)OC(C)(C)C)C(C)(C)C)cc1]

Intermediate AF (198 mg, 0.46 mmol) was reacted with PCC (300 mg, 1.39 mmol) as described under General Procedure K and was isolated by eluting the reaction mixture through pad of silica gel topped up with celite with 5% EtOAc in DCM. The aldehyde thus obtained and Intermediate I (300 mg, 0.60 mmol) were reacted as described under General Procedure L to furnish the title compound, which was purified by silica gel column chromatography (10% EtOAc/hexane) to yield (214 mg, 82%) as colourless gum. $^1$H NMR (500 MHz CDCl$_3$) δ 7.93 (d, 2H), 7.34-7.33 (m, 0.6H), 7.17-7.12 (m, 3.4H), 6.78-6.73 (m, 1.6H), 6.48 (d, 0.4H), 5.92-5.5.87 (m, 0.6H), 5.38-5.33 (m, 0.4H), 3.82 (s, 1.8H), 3.76 (s, 1.2H), 2.11-1.90 (m, 2H), 1.53-1.52 (m, 9H), 1.47-1.60 (m, 9), 1.41-1.25 (m, 2H).

Intermediate BB: tert-butyl tert-butyl[(4-{(1S,3S)-3-[(E/Z)-2-(5-chloro-2-methoxyphenyl)ethenyl]-2,2-dimethylcyclopropyl}phenyl)sulfonyl]carbamate

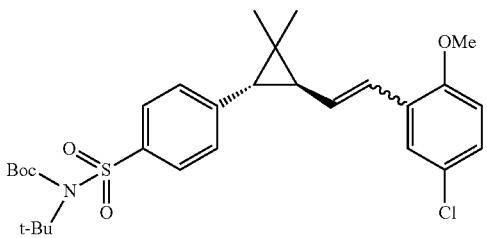 [SMILES: COc1ccc(Cl)cc1C=C[C@H]1[C@H](c2ccc(S(=O)(=O)N(C(=O)OC(C)(C)C)C(C)(C)C)cc2)C1(C)C]

Intermediate AE (249 mg, 0.55 mmol) was reacted with PCC (353 mg, 1.64 mmol) as described under General Procedure K and was isolated by eluting the reaction mixture through pad of silica gel topped up with celite with 5% EtOAc in DCM. The aldehyde thus obtained and Intermediate I (354 mg, 0.71 mmol) were reacted as described under General Procedure L to furnish the title compound, which was purified by silica gel column chromatography (5% EtOAc/hexane) to yield (244 mg, 75%) as colourless gum. $^1$H NMR (500 MHz, CDCl3) δ 7.96-7.92 (m, 2H), 7.37 (s, 1H), 7.31 (d, 0.8H), 7.21 (d, 1.2H), 7.21-7.18 (m, 0.6H), 7.14-7.11 (m, 0.4H), 6.85-6.82 (m, 1H), 6.78 (d, 0.4H), 6.62 (d, 0.6H), 6.14-6.09 (m, 0.4H), 5.67-5.63 (m, 0.6H), 3.85-3.84 (m, 3H), 2.14-2.12 (m, 0.4H), 2.09-2.06 (m, 0.6H), 2.04-2.00 (m, 1H), 1.51-1.46 (m, 18H), 1.33-1.31 (m, 3H), 0.91 (s, 3H).

Intermediate BC: tert-butyl tert-butyl({4-[(1S,3S)-2,2-dimethyl-3-{[(2-methylpyrimidin-5-yl)oxy]methyl}cyclopropyl]phenyl}sulfonyl)carbamate

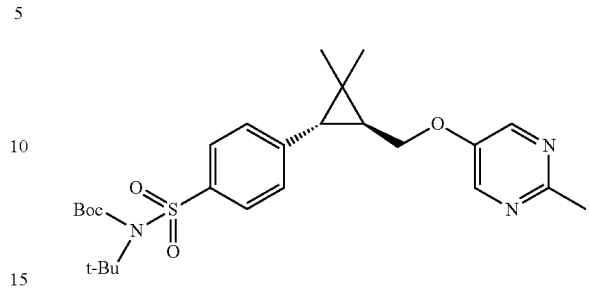

Intermediate AE (157 mg, 0.35 mmol) was reacted with 2-methylpyrimidin-5-ol (57 mg, 0.52 mmol), TPP-PS (230 mg, 0.69 mmol) and DIAD (0.14 mL, 0.69 mmol) in THF using General Procedure N. Purification by successive rounds of preparative TLC (70% Et$_2$O/hexane followed by 20% EtOAc/DCM) gave the title compound as a colourless gum (82 mg, 43%). $^1$H NMR (500 MHz, CDCl$_3$) δ 8.35 (s, 2H), 7.94-7.86 (m, 2H), 7.29-7.26 (m, 2H), 4.32-4.28 (m, 1H), 4.14-4.10 (m, 1H), 2.68 (s, 3H), 1.96-1.95 (m, 1H), 1.68-1.63 (m, 1H), 1.51 (s, 9H), 1.48 (s, 9H), 1.32 (s, 3H), 0.89 (s, 3H).

Intermediate BD: tert-butyl tert-butyl[(4-{(1S,3S)-2,2-dimethyl-3-[(pyrimidin-5-yloxy)methyl]cyclopropyl}phenyl)sulfonyl]carbamate

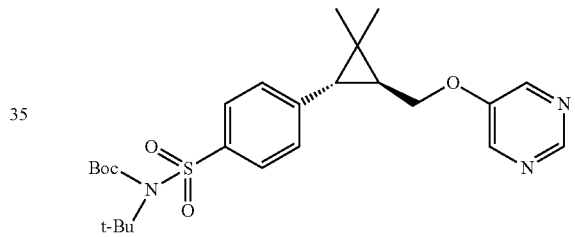

Intermediate AE (164 mg, 0.36 mmol) was reacted with 5-hydroxypyrimidine (57 mg, 0.54 mmol), TPP-PS (240 mg, 0.72 mmol) and DIAD (0.14 mL, 0.72 mmol) in THF using General Procedure N. Purification by successive rounds of preparative TLC (70% Et$_2$O/hexane followed by 80% Et$_2$O/hexane) gave the title compound as a colourless gum (52 mg, 26%). 1H NMR (500 MHz, CDCl3) δ 8.87 (s, 1H), 8.45 (s, 2H), 7.97-7.95 (m, 2H), 7.29-7.26 (m, 2H), 4.35-4.32 (m, 1H), 4.19-4.15 (m, 1H), 1.98-1.96 (m, 1H), 1.68-1.66 (m, 1H), 1.51 (s, 9H), 1.48 (s, 9H), 1.33 (s, 3H), 0.90 (s, 3H).

Intermediate BE: tert-butyl tert-butyl({4-[(1R,3R)-3-{[(5-chloropyridin-2-yl)oxy]methyl}-2,2-dimethylcyclopropyl]phenyl}sulfonyl)carbamate

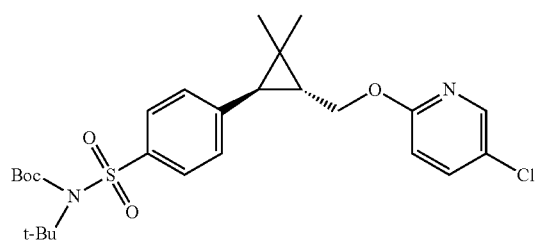 [SMILES: CC(C)(C)OC(=O)N(C(C)(C)C)S(=O)(=O)c1ccc([C@@H]2[C@@H](COc3ccc(Cl)cn3)C2(C)C)cc1]

Intermediate AD (324 mg, 0.71 mmol) was reacted with 5-chloropyridin-2-ol (101 mg, 0.78 mmol), TPP (205 mg, 0.78 mmol), DIAD (156 mg, 0.77 mmol) as described under General Procedure H to furnish the title compound (134 mg, 33%) as a colourless thick oil after silica gel column chromatography (0%→30% EtOAc in hexane). $^1$H NMR (500 MHz, CDCl$_3$) δ 8.09 (d, 1H), 7.93 (d, 2H), 7.53 (dd 1H), 7.27 (d, 2H), 6.73 (d, 1H), 4.53-4.50 (m, 1H), 4.38-4.35 (m, 1H), 1.92 (d, 1H), 1.69-1.65 (m, 1H), 1.50 (s, 9H), 1.48 (s, 9H), 1.32 (s, 3H), 0.86 (s, 3H).

Example 1: ±trans 4-{3-[(5-chloro-2-methoxyphenoxy)methyl]-2,2-dimethylcyclopropyl}benzenesulfonamide

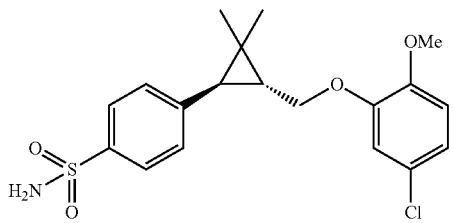 [SMILES: COc1ccc(Cl)cc1OC[C@@H]1[C@@H](c2ccc(S(N)(=O)=O)cc2)C1(C)C]

Intermediate C (100 mg, 0.4 mmol) and 5-chloro-2-methoxyphenol (63 mg, 0.44 mmol) were reacted as described under General Procedure H to furnish the title compound as a white solid after purification by column chromatography (10→70% cyclohexane/CH$_2$Cl$_2$). $^1$H NMR (300 MHz, DMSO-d$_6$) δ 7.72-7.68 (m, 2H), 7.38-7.35 (m, 2H), 7.26 (s, 2H), 7.07-7.06 (m, 1H), 6.97-6.90 (m, 2H), 4.27-4.20 (m, 1H), 4.11-4.04 (m, 1H), 3.74 (s, 3H), 1.97-1.94 (m, 1H), 1.73-1.67 (m, 1H), 1.22 (s, 3H), 0.80 (s, 3H). ESIMS m/z [M+H]$^+$396.3. Mp=158-160° C.

Example 2: ±trans 4-{2-[(5-chloro-2-methoxyphenoxy)methyl]spiro[2.4]hept-1-yl}benzenesulfonamide

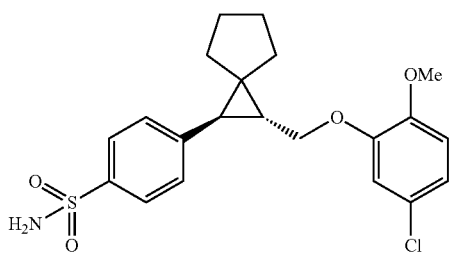 [SMILES: COc1ccc(Cl)cc1OC[C@@H]1[C@@H](c2ccc(S(N)(=O)=O)cc2)C12CCCC2]

Intermediate F (100 mg, 0.4 mmol) and 5-chloro-2-methoxyphenol (63 mg, 0.44 mmol) were reacted as described under General Procedure H to furnish the title compound as a white solid after column chromatography (10→70% cyclohexane/CH$_2$Cl$_2$). $^1$H NMR (300 MHz, DMSO-d$_6$) δ 7.72-7.68 (m, 2H), 7.31-7.28 (m, 2H), 7.25 (s, 3H), 7.06-7.05 (m, 1H), 6.93-6.89 (m, 2H), 4.22-4.16 (m, 1H), 4.04-3.98 (m, 1H), 3.72 (s, 3H), 2.09-2.07 (m, 1H), 1.93-1.38 (m, 8H), 1.15-1.09 (m, 1H). ESIMS m/z [M+H]$^+$ 422.3. Mp=56-58° C.

Example 3: ±trans 4-[3-{[4-fluoro-2-(trifluoromethyl)phenoxy]methyl}-2,2-dimethyl-cyclopropyl]benzenesulfonamide

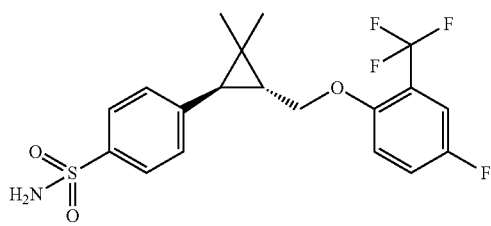 [SMILES: CC1(C)[C@H](COc2ccc(F)cc2C(F)(F)F)[C@H]1c1ccc(S(N)(=O)=O)cc1]

Intermediate C (58 mg, 0.23 mmol) and 4-fluoro-2-(trifluoromethyl) phenol (49 mg, 0.27 mmol) were reacted as described under General Procedure H to furnish the title compound, which was purified by column chromatography (5% ethyl acetate in DCM→20% ethyl acetate in DCM), as a colourless solid. $^1$H NMR (300 MHz, CDCl$_3$) δ 7.86-7.82 (m, 2H), 7.35-7.27 (m, 3H), 7.23-7.16 (m, 1H), 6.99-6.94 (m, 1H), 4.79-4.74 (m, 2H), 4.29-4.23 (m, 1H), 4.17-4.11 (m, 1H), 1.98-1.96 (m, 1H), 1.68-1.61 (m, 1H), 1.31 (s, 3H), 0.89 (s, 3H). ESIMS m/z [M−H]$^-$ 416.2.

Example 4: ±trans 4-{2-[2-(5-chloro-2-methoxyphenyl)ethyl]spiro[2.4]hept-1-yl}benzenesulfonamide

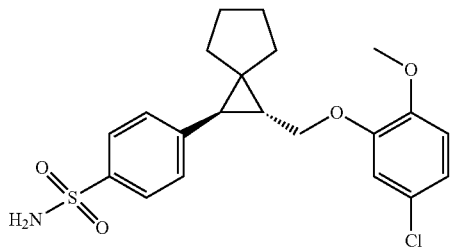 [SMILES: COc1ccc(Cl)cc1OC[C@@H]1[C@@H](c2ccc(S(N)(=O)=O)cc2)C12CCCC2]

Intermediate J (100 mg, 0.24 mmol) was reacted as described under General Procedure M to furnish the title compound. $^1$H NMR (300 MHz, DMSO-d$_6$) δ 7.68-7.65 (m, 2H), 7.22-7.15 (m, 6H), 6.93-6.89 (m, 1H), 3.72 (s, 3H), 2.71-2.57 (m, 2H), 1.75-0.99 (m, 12H). ESIMS m/z [M+Na]$^+$442.6.

Example 5: N-(4-{(1S,3S)-3-[(5-chloro-2-methoxyphenoxy)methyl]-2,2-dimethylcyclopropyl}phenyl)methanesulfonamide

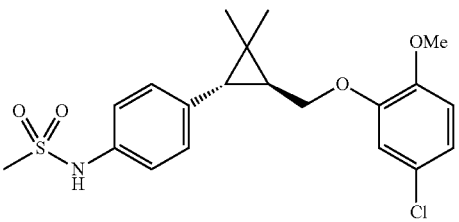 [SMILES: COc1ccc(Cl)cc1OC[C@H]1[C@H](c2ccc(NS(C)(=O)=O)cc2)C1(C)C]

Intermediate P (40 mg, 0.10 mmol) and methane sulfonamide (11 mg, 0.12 mmol) were reacted as described under General Procedure I to furnish the title compound as a colourless solid after preparative TLC (30% ethyl acetate in hexane). $^1$HNMR (500 MHz, CDCl$_3$) δ 7.17-7.11 (m, 4H), 6.92-6.89 (m, 2H), 6.81-6.79 (m, 1H), 6.27 (s, 1H), 4.26-4.23 (m, 1H), 4.11-4.07 (m, 1H), 3.85 (s, 3H), 2.99 (s, 3H), 1.84-1.83 (m, 1H), 1.59-1.57 (m, 1H), 1.27 (s, 3H), 0.87 (s, 3H). HRMS (ESI) calcd. for C$_{20}$H$_{24}$ClNO$_4$S (M−H)$^-$ 408.1042, found 408.1040.

Example 6: N-{4-[(1S,3S)-3-{[(6-methoxypyridin-3-yl)oxy]methyl}-2,2-dimethylcyclopropyl]phenyl}methanesulfonamide

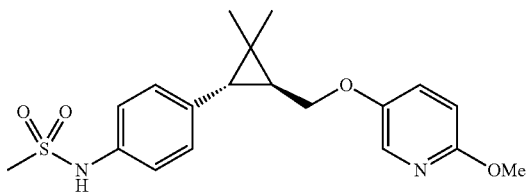 [SMILES: COc1ccc(OC[C@H]2[C@H](c3ccc(NS(C)(=O)=O)cc3)C2(C)C)cn1]

Intermediate Q (50 mg, 0.14 mmol) and methane sulfonamide (16 mg, 0.17 mmol) were reacted as described under General Procedure I to furnish the title compound product as a colourless oil after preparative TLC (30% ethyl acetate in hexane). $^1$H NMR (500 MHz, CDCl$_3$) δ 7.85-7.84 (m, 1H), 7.26-7.24 (m, 1H), 7.18-7.13 (m, 4H), 6.70-6.68 (m, 1H), 6.43 (s, 1H), 4.23-4.20 (m, 1H), 4.02-3.98 (m, 1H), 3.89 (s, 3H), 3.00 (s, 3H), 1.84-1.83 (m, 1H), 1.54-1.50 (m, 1H), 1.28 (s, 3H), 0.87 (s, 3H). HRMS (ESI) calcd. for C$_{19}$H$_{24}$N$_2$O$_4$S (M−H)$^-$ 375.1384, found 375.1382.

Example 7: N-(4-{(1S,3S)-3-[(4-fluoro-2-methyl-phenoxy)methyl]-2,2-dimethyl-cyclopropyl}phenyl)methanesulfonamide

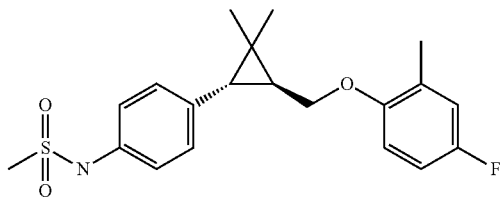 [SMILES: Cc1cc(F)ccc1OC[C@H]1[C@H](c2ccc(NS(C)(=O)=O)cc2)C1(C)C]

Intermediate AZ (52 mg, 0.14 mmol) and methane sulfonamide (16 mg, 0.17 mmol) were reacted as described under General Procedure I to furnish the title compound as an off-white solid after column chromatography (20% ethyl acetate/hexane). $^1$H NMR (500 MHz, CDCl$_3$) δ 7.19-7.13 (m, 4H), 6.88-6.74 (m, 3H), 6.46 (s, 1H), 4.19-4.16 (m, 1H), 4.02-3.99 (m, 1H), 3.00 (s, 3H), 2.24 (s, 3H), 1.85-1.84 (m, 1H), 1.54-1.50 (m, 1H), 1.28 (s, 3H), 0.88 (s, 3H). ESIMS m/z [M−H]$^-$ 376.1.

Example 8: N-(4-{(1S,3S)-3-[(4-fluoro-2-methyl-phenoxy)methyl]-2,2-dimethylcyclopropyl}phenyl) sulfuric diamide

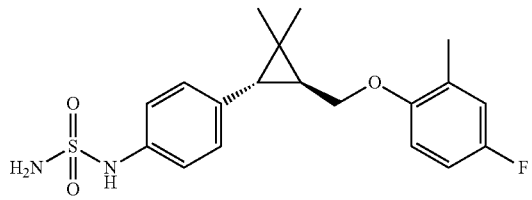 [SMILES: Cc1cc(F)ccc1OC[C@H]1[C@H](c2ccc(NS(N)(=O)=O)cc2)C1(C)C]

Intermediate AZ (178 mg, 0.49 mmol) and sulfamide (57 mg, 0.58 mmol) were reacted as described under General Procedure I to furnish the title compound as a colourless solid after column chromatography (30% ethyl acetate/hexane). $^1$H NMR (500 MHz, CDCl$_3$) δ 7.20-7.11 (m, 4H), 6.89-6.74 (m, 3H), 6.33 (s, 1H), 4.64 (s, 2H), 4.19-4.15 (m, 1H), 4.03-3.99 (m, 1H), 2.24 (s, 3H), 1.85-1.84 (m, 1H), 1.57-1.50 (m, 1H), 1.28 (s, 3H), 0.88 (s, 3H). ESIMS m/z [M−H]$^-$ 377.1.

Example 9: N-(4-{(1S,3S)-3-[(5-fluoro-2-methyl-phenoxy)methyl]-2,2-dimethyl-cyclopropyl}phenyl) sulfuric diamide

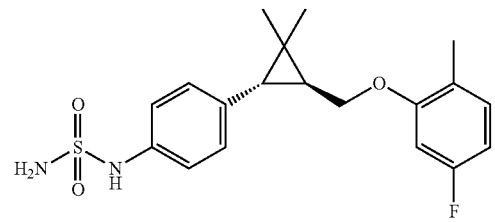 [SMILES: Cc1ccc(F)cc1OC[C@H]1[C@H](c2ccc(NS(N)(=O)=O)cc2)C1(C)C]

Intermediate AY (202 mg, 0.56 mmol) and sulfamide (64 mg, 0.67 mmol) were reacted as described under General Procedure I to furnish the title compound as a colourless solid after column chromatography (33% ethyl acetate/hexane). $^1$H NMR (500 MHz, CDCl$_3$) δ 7.22-7.14 (m, 4H), 7.08-7.03 (m, 1H), 6.60-6.53 (m, 2H), 6.36 (s, 1H), 4.65 (s, 2H), 4.19-4.15 (m, 1H), 4.04-4.00 (m, 1H), 2.20 (s, 3H), 1.88-1.86 (m, 1H), 1.55-1.50 (m, 1H), 1.29 (s, 3H), 0.89 (s, 3H). ESIMS m/z [M−H]$^-$ 377.1.

Example 10: 4-[(1S,3S)-3-{[4-fluoro-2-(trifluoromethyl)phenoxy]methyl}-2,2-dimethyl-cyclopropyl]benzenesulfonamide

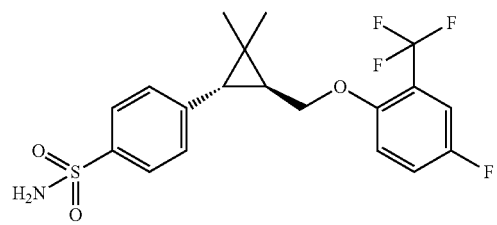 [SMILES: CC1(C)[C@@H](COc2ccc(F)cc2C(F)(F)F)[C@@H]1c1ccc(S(N)(=O)=O)cc1]

Example 10 was prepared from Intermediate V (45 mg, 0.18 mmol), 4-fluoro-2-trifluoromethylphenol (38 mg, 0.21 mmol), TPP (169 mg, 0.19 mmol) and DIAD (38 µL, 0.19 mmol) in THF using General Procedure H. Purification by column chromatography on silica, eluting with 5% EtOAc/DCM and recrystallization from Et2O/hexane gave the title compound as a white solid. ¹H NMR (500 MHz, CDCl₃) δ 7.86-7.82 (m, 2H), 7.36-7.28 (m, 3H), 7.22-7.16 (m, 1H), 6.98-6.95 (m, 1H), 4.73 (s, 2H), 4.28-4.25 (m, 1H), 4.17-4.10 (m, 1H), 1.98-1.96 (m, 1H), 1.67-1.63 (m, 1H), 1.31 (s, 3H), 0.89 (s, 3H). ESIMS m/z [M–H]⁻ 416.0.

Example 11: 4-{(1S,3S)-3-[(5-chloro-2-methoxyphenoxy)methyl]-2,2-dimethyl-cyclopropyl}benzenesulfonamide

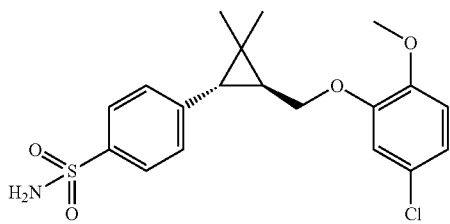 [SMILES: COc1ccc(Cl)cc1OC[C@H]1[C@H](c2ccc(S(N)(=O)=O)cc2)C1(C)C]

Example 11 was prepared from Intermediate V (150 mg, 0.59 mmol), 5-chloro-2-methoxyphenol (112 mg, 0.71 mmol), TPP (169 mg, 0.65 mmol) and DIAD (0.13 mL, 0.65 mmol) in THF using General Procedure H. Purification by column chromatography on silica, eluting with 50% Et2O/Hexane then 10% EtOAc/DCM followed by an additional purification using column chromatography (70% Et2O/Hexane) and recrystallization from Et2O/hexane gave the title compound as a white solid. ¹H NMR (500 MHz, CDCl₃) δ 7.84-7.81 (m, 2H), 7.33-7.28 (m, 2H), 6.93-6.89 (m, 2H), 6.81-6.78 (m, 1H), 4.72 (s, 2H), 4.26-4.22 (m, 1H), 4.16-4.10 (m, 1H), 3.84 (s, 3H), 1.93-1.92 (m, 1H), 1.70-1.66 (m, 1H), 1.30 (s, 3H), 0.88 (s, 3H). ESIMS m/z [M–H]⁻ 394.0.

Example 12: 4-{(1R,3R)-3-[(5-chloro-2-methoxyphenoxy)methyl]-2,2-dimethyl-cyclopropyl}benzenesulfonamide

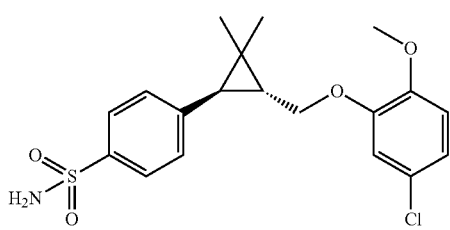 [SMILES: COc1ccc(Cl)cc1OC[C@@H]1[C@@H](c2ccc(S(N)(=O)=O)cc2)C1(C)C]

Intermediate U (200 mg, 0.78 mmol) was reacted with 4-chloro-2-methoxy phenol (136 mg, 0.08 mmol), TPP (205 mg, 0.78 mmol), DIAD (158 mg, 0.78 mmol) as described under General Procedure H to furnish the title compound as off-white solid after column chromatography (15%→100% ethyl acetate in hexane). ¹H NMR (500 MHz, CDCl₃) δ 7.82 (d, 2H), 7.31 (d, 2H), 6.92-6.90 (m, 2H), 6.80 (d, 1H), 4.76 (s, 2H), 4.26-4.22 (m, 1H), 4.16-4.12 (m, 1H), 3.84 (s, 3H), 1.92 (d, 1H), 1.68 (q, 1H), 1.30 (s, 3H), 0.88 (s, 3H). ESIMS m/z [M–H]⁻ 394.0.

Example 13: 4-[(1S,3S)-3-(4-methyl-phenylsulfanylmethyl)-2,2-dimethyl-cyclopropyl]-benzenesulfonamide

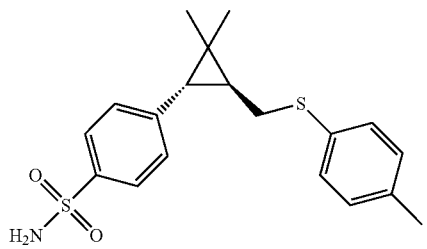 [SMILES: Cc1ccc(SC[C@H]2[C@H](c3ccc(S(N)(=O)=O)cc3)C2(C)C)cc1]

Intermediate AR (500 mg, 0.89 mmol) was reacted as described under General Procedure G to furnish the title compound as a white foam. ¹H NMR (300 MHz, CDCl₃) δ 7.79 (d, 2H), 7.30 (d, 2H), 7.21 (d, 2H), 7.09 (d, 2H), 4.96 (bs, 2H), 3.17-2.96 (m, 2H), 2.32 (s, 3H), 1.74 (d, 1H), 1.42-1.35 (m, 1H), 1.25 (s, 3H), 0.79 (s, 3H). ESIMS m/z (M+Na⁺) 384.3.

Example 14: 4-[(1R,3R)-3-(5-Chloro-2-methoxyphenylsulfanylmethyl)-2,2-dimethyl-cyclopropyl]-benzenesulfonamide

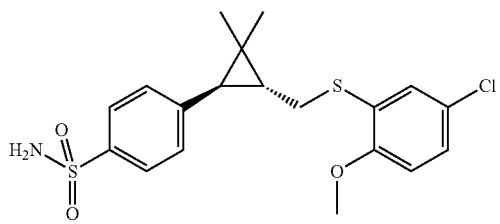 [SMILES: COc1ccc(Cl)cc1SC[C@@H]1[C@@H](c2ccc(S(N)(=O)=O)cc2)C1(C)C]

Intermediate AP (540 mg, 0.88 mmol) was reacted as described under General Procedure G to furnish the title compound as a colorless oil. ¹H NMR (300 MHz, CDCl₃) δ 7.79 (d, 2H), 7.23-7.19 (m, 3H), 7.11 (dd, 1H), 6.74 (d, 1H), 4.98 (bs, 2H), 3.86 (s, 3H), 3.15-2.97 (m, 2H), 1.77 (d, 1H), 1.42-1.35 (m, 1H), 1.25 (s, 3H), 0.80 (s, 3H). ESIMS m/z (M+Na⁺) 434.5.

Example 15: 4-[(1R,3R)-3-(4-methyl-phenylsulfanylmethyl)-2,2-dimethyl-cyclopropyl]-benzenesulfonamide

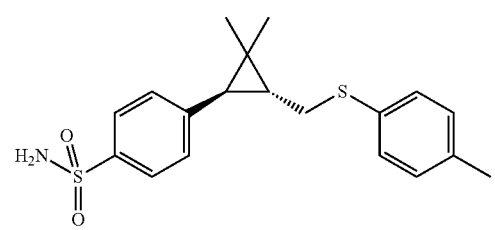 [SMILES: Cc1ccc(SC[C@@H]2[C@@H](c3ccc(S(N)(=O)=O)cc3)C2(C)C)cc1]

Intermediate AS (190 mg, 0.34 mmol) was reacted as described under General Procedure G to furnish the title compound as a colorless oil. ¹H NMR (300 MHz, CDCl₃) δ 7.79 (d, 2H), 7.30 (d, 2H), 7.22 (d, 2H), 7.09 (d, J=8.1 Hz, 2H), 4.74 (bs, 2H), 3.18-2.96 (m, 2H), 2.32 (s, 3H), 1.74 (d, 1H), 1.39 (m, 1H), 1.21 (s, 3H), 0.78 (s, 3H). ESIMS m/z (M−H⁻) 360.3.

Example 16: 4-[(1S,3S)-3-(5-Chloro-2-methoxy-phenylsulfanylmethyl)-2,2-dimethyl-cyclopropyl]-benzenesulfonamide

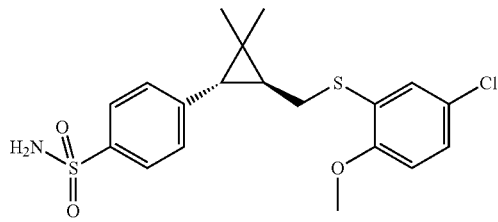 [SMILES: COc1ccc(Cl)cc1SC[C@H]1[C@H](c2ccc(S(N)(=O)=O)cc2)C1(C)C]

Intermediate AO (640 mg, 1.05 mmol) was reacted as described under General Procedure G to furnish the title compound as a white solid. ¹H NMR (300 MHz, CDCl₃) δ 7.68 (d, 2H), 7.30-7.25 (m, 4H), 7.24 (d, 1H), 7.16 (dd, 1H), 6.95 (d, 1H), 3.78 (s, 3H), 3.13 (d, 2H), 1.87 (d, 1H), 1.44-1.37 (m, 1H), 1.22 (s, 3H), 0.75 (s, 3H). ESIMS m/z (M+Na⁺) 434.5.

Example 17: N-{4-[(1S,3S)-3-{[(6-methoxypyridin-3-yl)oxy]methyl}-2,2-dimethyl-cyclopropyl]phenyl}sulfuric diamide

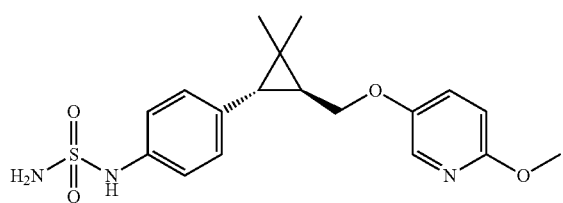 [SMILES: COc1ccc(OC[C@H]2[C@H](c3ccc(NS(N)(=O)=O)cc3)C2(C)C)cn1]

Intermediate AX (15 mg, 31 mmol) was reacted as described under General Procedure J to furnish the title compound as a white solid after column chromatography (10%→20% EtOAc/DCM). ¹H NMR (500 MHz, CDCl₃) δ 7.85-7.84 (m, 1H), 7.26-7.23 (m, 1H), 7.19-7.13 (m, 4H), 6.68 (d, 1H), 6.38 (s, 1H), 4.67 (s, 2H), 4.23-4.19 (m, 1H), 4.02-3.98 (m, 1H), 3.89 (s, 3H), 1.83 (d, 1H), 1.54-1.49 (m, 1H), 1.27 (s, 3H), 0.88 (s, 3H). ESIMS m/z [M−H]⁻ 376.1.

Example 18: N-{4-[(1S,3S)-2,2-dimethyl-3-{[(6-methylpyridin-3-yl)oxy]methyl}-cyclopropyl]phenyl}sulfuric diamide

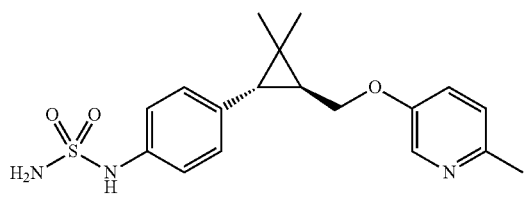 [SMILES: Cc1ccc(OC[C@H]2[C@H](c3ccc(NS(N)(=O)=O)cc3)C2(C)C)cn1]

Intermediate AW (81 mg, 0.23 mmol) and sulfamide (157 mg, 1.6 mmol) were reacted as described under General Procedure I to furnish the title compound as a colourless solid after preparative TLC (70% ethyl acetate/hexane). ¹H NMR (500 MHz, CDCl₃) δ 8.22-8.20 (m, 1H), 7.20-7.12 (m, 5H), 7.06 (d, 1H), 6.57-6.42 (br m, 1H), 4.78-4.70 (br m, 2H), 4.25-4.21 (m, 1H), 4.07-4.03 (m, 1H), 2.49 (s, 3H), 1.86-1.84 (m, 1H), 1.55-1.50 (m, 1H), 1.28 (s, 3H), 0.88 (s, 3H). ESIMS m/z [M−H]⁻ 360.1.

Example 19: N-{4-[(1S,3S)-2,2-dimethyl-3-{[(2-methylpyridin-3-yl)oxy]methyl}-cyclopropyl]phenyl}methanesulfonamide

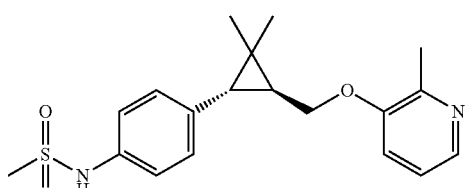

Intermediate AV (71 mg, 0.21 mmol) and methane sulphonamide (137 mg, 1.4 mmol) were reacted as described under General Procedure I to furnish the title compound as a white solid after preparative TLC (60% ethyl acetate/hexane). ¹HNMR (500 MHz, CDCl₃) δ 8.10-8.08 (m, 1H), 7.20-7.11 (m, 4H), 7.10-7.06 (m, 2H), 6.28 (s, 1H), 4.24-4.20 (m, 1H), 4.07-4.04 (m, 1H), 3.00 (s, 3H), 2.51 (s, 3H), 1.88 (d, 1H), 1.55-1.52 (m, 1H), 1.30 (s, 3H), 0.90 (s, 3H). ESIMS m/z [M−H]⁻ 359.1.

Example 20: N-{4-[(1S,3S)-2,2-dimethyl-3-{[(2-methylpyridin-3-yl)oxy]methyl}-cyclopropyl]phenyl}sulfuric diamide

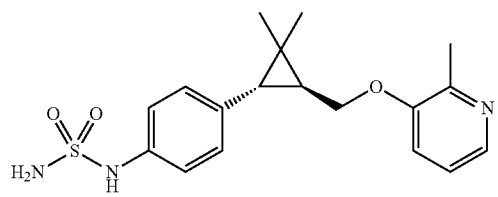 [SMILES: Cc1ncccc1OC[C@H]1[C@H](c2ccc(NS(N)(=O)=O)cc2)C1(C)C]

Intermediate AV (67 mg, 0.19 mmol) and sulfamide (130 mg, 1.4 mmol) were reacted as described under General Procedure I to furnish the title compound as a white solid after preparative TLC (70% ethyl acetate/hexane). ¹H NMR (500 MHz, DMSO-d₆) δ 9.37 (br s, 1H), 8.04-8.02 (m, 1H), 7.42 (d, 1H), 7.23-7.19 (m, 1H), 7.18-7.10 (m, 4H), 7.10-7.04 (m, 2H), 4.38-4.34 (m, 1H), 4.13-4.09 (m, 1H), 2.42 (s, 3H), 1.92 (d, 1H), 1.60-1.55 (m, 1H), 1.28 (s, 3H), 0.86 (s, 3H). ESIMS m/z [M−H]⁻ 360.1.

Example 21: 4-[(1R,3R)-3-{[(2,6-dimethoxypyridin-3-yl)oxy]methyl}-2,2-dimethyl-cyclopropyl]benzenesulfonamide

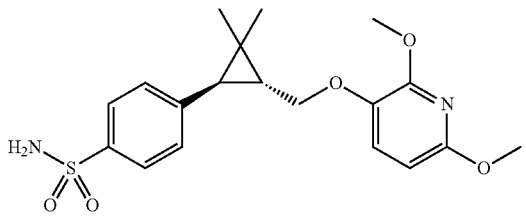 [SMILES: COc1ccc(OC[C@@H]2[C@@H](c3ccc(S(N)(=O)=O)cc3)C2(C)C)c(OC)n1]

Intermediate U (200 mg, 0.78 mmol) was reacted with 2,6-dimethoxypyridin-3-ol (182 mg, 1.17 mmol), TPP (205 mg, 0.78 mmol), DIAD (158 mg, 0.78 mmol) as described under General Procedure H to furnish the title compound as pale-yellow semi-solid after PLC purification (50% diethyl ether in hexane), followed by column chromatography (50% diethyl ether in hexane). $^1$H NMR (500 MHz, CDCl$_3$) δ 7.81 (d, 2H), 7.27 (d, 2H), 7.19 (d, 1H), 6.20 (d, 1H), 4.98 (s, 2H), 4.22-4.19 (m, 1H), 4.06-4.03 (m, 1H), 3.96 (s, 3H), 3.87 (s, 3H), 1.85 (d, 1H), 1.66-1.61 (m, 1H), 1.25 (s, 3H), 0.84 (s, 3H). ESIMS m/z [M−H]⁻ 391.1.

Example 22: 4-[(1R,3R)-3-{[2-(difluoromethoxy)-5-fluorophenoxy]methyl}-2,2-dimethylcyclopropyl]benzenesulfonamide

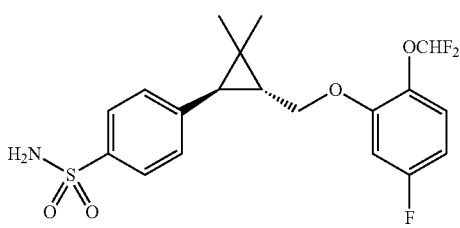 [SMILES: CC1(C)[C@H](COc2cc(F)ccc2OC(F)F)[C@H]1c1ccc(S(N)(=O)=O)cc1]

Intermediate U (200 mg, 0.78 mmol) was reacted with 2-(difluoromethoxy)-5-fluorophenol (209 mg, 1.17 mmol), TPP (205 mg, 0.78 mmol), DIAD (158 mg, 0.78 mmol) as described under General Procedure H to furnish the title compound as pale-yellow gum after column chromatography (50% diethyl ether in hexane), followed by PLC purification (50% diethyl ether in hexane). $^1$H NMR (500 MHz, CDCl$_3$) δ 7.85 (d, 2H), 7.32 (d, 2H), 7.15-7.12 (m, 1H), 6.74-6.34 (m, 3H), 4.87 (s, 2H), 4.26-4.23 (m, 1H), 4.13-4.10 (m, 1H), 1.97 (d, 1H), 1.66 (q, 1H), 1.32 (s, 3H), 0.89 (s, 3H). ESIMS m/z [M−H]⁻ 414.0.

Example 23: N-(4-{(1S,3S)-3-[(4-chloro-2-methoxyphenoxy)methyl]-2,2-dimethyl-cyclopropyl}phenyl)sulfuric diamide

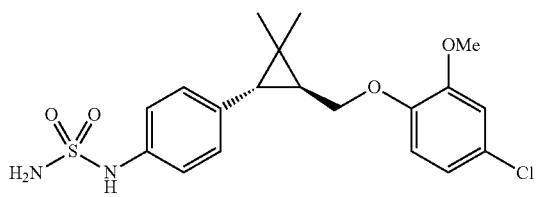 [SMILES: COc1cc(Cl)ccc1OC[C@H]1[C@H](c2ccc(NS(N)(=O)=O)cc2)C1(C)C]

Intermediate AU (65 mg, 0.16 mmol) and sulfamide (110 mg, 1.2 mmol) were reacted as described under General Procedure I to furnish the title compound as a white solid after preparative TLC (40% ethyl acetate/hexane followed by 80% Et2O/Hexane). $^1$H NMR (500 MHz, CDCl$_3$) δ 7.18-7.10 (m, 4H), 6.90-6.84 (m, 3H), 6.34 (s, 1H), 4.65 (s, 2H), 4.26-4.22 (m, 1H), 4.10-4.06 (m, 1H), 3.85 (s, 3H), 1.81 (d, 1H), 1.60-1.54 (m, 1H), 1.25 (s, 3H), 0.86 (s, 3H). ESIMS m/z [M−H]⁻ 409.0.

Example 24: N-(4-{(1S,3S)-3-[(4-fluoro-2-methoxyphenoxy)methyl]-2,2-dimethyl-cyclopropyl}phenyl)sulfuric diamide

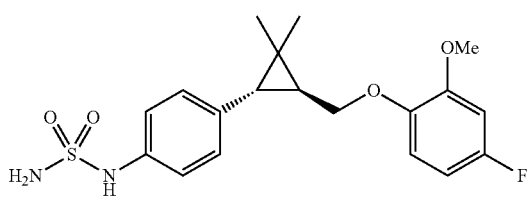 [SMILES: COc1cc(F)ccc1OC[C@H]1[C@H](c2ccc(NS(N)(=O)=O)cc2)C1(C)C]

Intermediate AT (64 mg, 0.17 mmol) and sulfamide (114 mg, 1.2 mmol) were reacted as described under General Procedure I to furnish the title compound as a off-white solid after preparative TLC (35% ethyl acetate in hexane). $^1$H NMR (500 MHz, CDCl$_3$) δ 7.16-7.11 (m, 4H), 6.90-6.86 (m, 1H), 6.66-6.62 (m, 1H), 6.60-6.55 (m, 1H), 6.33 (br s, 1H), 4.64 (s, 2H), 4.26-4.22 (m, 1H), 4.08-4.04 (m, 1H), 3.84 (s, 3H), 1.79 (d, 1H), 1.57-1.53 (m, 1H), 1.24 (s, 3H), 0.85 (s, 3H). ESIMS m/z [M−H]⁻ 393.1.

Example 25: 4-{(1S,3S)-2,2-dimethyl-3-[(pyridin-3-yloxy)methyl]cyclopropyl}-benzenesulfonamide

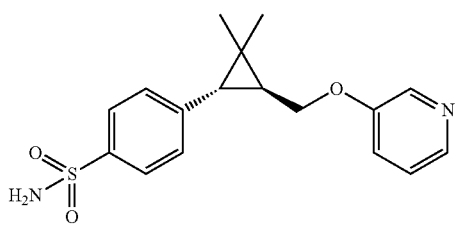 [SMILES: CC1(C)[C@@H](COc2cccnc2)[C@@H]1c1ccc(S(N)(=O)=O)cc1]

Example 25 was prepared from Intermediate V (100 mg, 0.39 mmol), 3-hydroxypyridine (45 mg, 47 mmol), TPP-PS (144 mg, 0.43 mmol) and DIAD (85 μL, 0.43 mmol) in THF using General Procedure N. Purification by preparative TLC on silica, eluting with 100% Et$_2$O (plate run twice), gave the title compound as a colourless glassy solid. $^1$H NMR (500 MHz, CDCl$_3$) δ 8.37-8.34 (m, 1H), 8.25-8.23 (m, 1H), 7.84 (d, 2H), 7.32 (d, 2H), 7.25-7.23 (m, 2H), 4.27 (s, 2H), 4.29-4.25 (m, 1H), 4.14-4.09 (m, 1H), 1.96 (d, 1H), 1.67 (q, 1H), 1.33 (s, 3H), 0.90 (s, 3H). ESIMS m/z [M−H]⁻ 331.1.

Example 26: 4-[(1S,3S)-3-{[(2,6-dimethoxypyridin-3-yl)oxy]methyl}-2,2-dimethyl-cyclopropyl]benzenesulfonamide

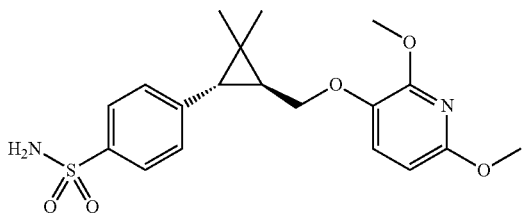 [SMILES: COc1ccc(OC[C@H]2[C@H](c3ccc(S(N)(=O)=O)cc3)C2(C)C)c(OC)n1]

Intermediate U (200 mg, 0.78 mmol) was reacted with 2,6-dimethoxypyridin-3-ol (182 mg, 1.17 mmol), TPP (205 mg, 0.78 mmol), DIAD (158 mg, 0.78 mmol) as described under General Procedure H to furnish the title compound as white powder after 2 PLC purifications (first PLC in 30% EtOAc in hexane and second in 50% diethyl ether in hexane). $^1$H NMR (500 MHz, CDCl$_3$) δ 7.82 (d, 2H), 7.29 (d, 2H), 7.20 (d, 1H), 6.21 (d, 1H), 4.82 (s, 2H), 4.24-4.21 (m, 1H), 4.08-4.05 (m, 1H), 3.98 (s, 3H), 3.89 (s, 3H), 1.87 (d, 1H), 1.67-1.63 (m, 1H), 1.27 (s, 3H), 0.86 (s, 3H). ESIMS m/z [M+H]$^+$ 393.1.

Example 27: 4-[(1R,3R)-2,2-dimethyl-3-{[(6-methylpyridin-3-yl)oxy]methyl}-cyclopropyl]benzenesulfonamide

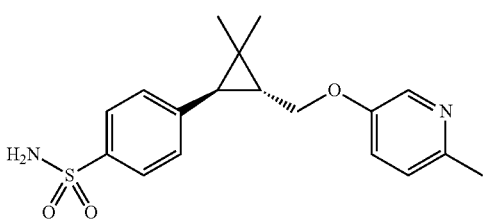 [SMILES: Cc1ccc(OC[C@@H]2[C@@H](c3ccc(S(N)(=O)=O)cc3)C2(C)C)cn1]

Intermediate U (150 mg, 0.58 mmol) was reacted with 6-methyl pyridin-3-ol (109 mg, 0.70 mmol), TPP-PS (195 mg, 0.58 mmol), DIAD (119 mg, 0.58 mmol) as described under General Procedure N to furnish the title compound as white solid after PLC (50% diethyl ether in hexane) purification, followed by silica gel column chromatography (2%→4% MeOH in DCM). $^1$H NMR (500 MHz, CDCl$_3$) δ 8.22 (d, 1H), 7.84 (d, 2H), 7.31 (d, 2H), 7.16-7.06 (m, 2H), 4.83 (s, 2H), 4.26-4.23 (m, 1H), 4.10-4.06 (m, 1H), 2.49 (s, 3H), 1.94 (d, 1H), 1.65 (q, 1H), 1.32 (s, 3H), 0.89 (s, 3H). ESIMS m/z [M+H]$^+$ 347.1.

Example 28: 4-{(1R,3R)-3-[(2-cyano-4-fluorophenoxy)methyl]-2,2-dimethyl-cyclopropyl}benzenesulfonamide

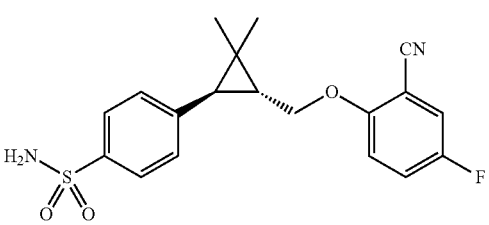 [SMILES: CC1(C)[C@H](COc2ccc(F)cc2C#N)[C@H]1c1ccc(S(N)(=O)=O)cc1]

Intermediate U (150 mg, 0.58 mmol) was reacted with 5-fluoro-2-hydroxybenzonitrile (97 mg, 0.70 mmol), TPP-PS (195 mg, 0.58 mmol), DIAD (119 mg, 0.58 mmol) as described under General Procedure N to furnish the title compound as white solid after preparative TLC (30% diethyl ether in hexane) purification, followed by silica gel column chromatography (2%→5% MeOH in DCM). $^1$H NMR (500 MHz, CDCl$_3$) δ 7.84 (d, 2H), 7.34 (d, 2H), 7.30-7.24 (m, 2H), 6.98-6.95 (m, 1H), 4.76 (s, 2H), 4.33-4.29 (m, 1H), 4.21-4.17 (m, 1H), 1.99 (d, 1H), 1.67 (q, 1H), 1.34 (s, 3H), 0.91 (s, 3H). ESIMS m/z [M-H]$^-$ 373.1.

Example 29: 4-{(1R,3R)-3-[(4-fluoro-2-methoxyphenoxy)methyl]-2,2-dimethyl-cyclopropyl}benzenesulfonamide

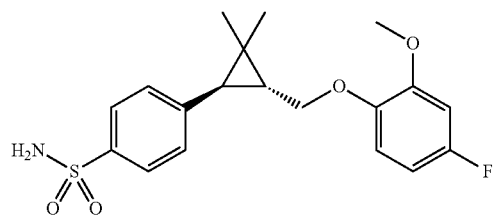 [SMILES: COc1cc(F)ccc1OC[C@@H]1[C@@H](c2ccc(S(N)(=O)=O)cc2)C1(C)C]

Intermediate U (150 mg, 0.58 mmol) was reacted with 4-fluoro-2-methoxyphenol (77 mg, 0.70 mmol), TPP-PS (195 mg, 0.58 mmol), DIAD (119 mg, 0.58 mmol) as described under General Procedure N to furnish the title compound as white solid after preparative TLC (50% diethyl ether in hexane) purification, followed by trituration from 50% diethyl ether in hexane. $^1$H NMR (500 MHz, CDCl$_3$) δ 7.82 (d, 2H), 7.28 (d, 2H), 6.90-6.87 (m, 1H), 6.66-6.55 (m, 2H), 4.82 (s, 2H), 4.25-4.21 (m, 1H), 4.12-4.08 (m, 1H), 3.84 (s, 3H), 1.88 (d, 1H), 1.66 (q, 1H), 1.27 (s, 3H), 0.86 (s, 3H). ESIMS m/z [M-H]$^-$ 378.1.

Example 30: 4-{(1S,3S)-3-[(4-fluoro-2-methoxyphenoxy)methyl]-2,2-dimethyl-cyclopropyl}benzenesulfonamide

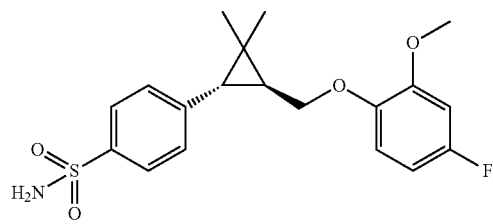 [SMILES: COc1cc(F)ccc1OC[C@H]1[C@H](c2ccc(S(N)(=O)=O)cc2)C1(C)C]

Example 30 was prepared from Intermediate V (120 mg, 0.47 mmol), 4-fluoro-2-methoxyphenol (64 μL, 0.56 mmol), TPP (136 mg, 0.52 mmol) and DIAD (0.10 mL, 0.52 mmol) in THF using General Procedure H. Purification by preparative TLC on silica, eluting with 70% Et$_2$O/Hexane, gave the title compound as a very pale yellow viscous oil. $^1$H NMR (500 MHz, CDCl3) δ 7.83-7.80 (m, 2H), 7.30-7.28 (m, 2H), 6.90-6.86 (m, 1H), 6.66-6.63 (m, 1H), 6.59-6.55 (m, 1H), 4.79 (s, 2H), 4.25-4.21 (m, 1H), 4.12-4.07 (m, 1H), 3.84 (s, 3H), 1.88 (d, 1H), 1.66 (q, 1H), 1.27 (s, 3H), 0.86 (s, 3H). ESIMS m/z [M-H]$^-$ 378.1.

Example 31: 4-{(1S,3S)-3-[(4-fluoro-2-methylphenoxy)methyl]-2,2-dimethylcyclopropyl}benzenesulfonamide

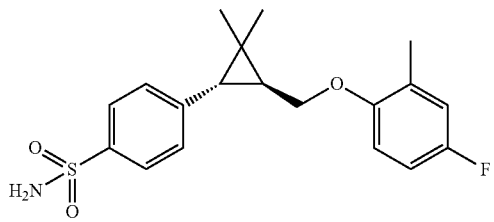 [SMILES: Cc1cc(F)ccc1OC[C@H]1[C@H](c2ccc(S(N)(=O)=O)cc2)C1(C)C]

Example 31 was prepared from Intermediate V (120 mg, 0.47 mmol), 4-fluoro-2-methylphenol (71 mg, 0.56 mmol), TPP (136 mg, 0.52 mmol) and DIAD (0.10 mL, 0.52 mmol) in THF using General Procedure H. Purification by preparative TLC on silica, eluting with 5% EtOAc/DCM, followed by further purification by preparative TLC on silica, eluting with 70% Et$_2$O/Hexane, gave the title compound as a colourless viscous oil. $^1$H NMR (500 MHz, CDCl3) δ 7.85-7.83 (m, 2H), 7.34-7.31 (m, 2H), 6.88-6.86 (m, 1H), 6.84-6.82 (m, 1H), 6.77-6.74 (m, 1H), 4.84 (s, 2H), 4.19-4.15 (m, 1H), 4.06-4.02 (m, 1H), 2.24 (s, 3H), 1.93 (d, 1H), 1.64 (q, 1H), 1.31 (s, 3H), 0.89 (s, 3H). ESIMS m/z [M−H]$^-$ 362.1.

Example 32: 4-{(1S,3S)-3-[(2-cyano-4-fluorophenoxy)methyl]-2,2-dimethylcyclopropyl}benzenesulfonamide

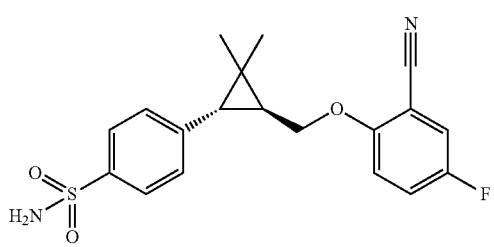 [SMILES: CC1(C)[C@@H](COc2ccc(F)cc2C#N)[C@@H]1c1ccc(S(N)(=O)=O)cc1]

Example 32 was prepared from Intermediate V (120 mg, 0.47 mmol), 5-fluoro-2-hydroxybenzonitrile (77 mg, 0.56 mmol), TPP (136 mg, 0.52 mmol) and DIAD (0.10 mL, 0.52 mmol) in THF using General Procedure H. Purification by preparative TLC on silica, eluting with 70% Et$_2$O/Hexane, gave a partially purified product. This product was further purified by preparative TLC on silica, eluting with 10% EtOAc/DCM, to give the title compound as a colourless glassy solid. $^1$H NMR (500 MHz, CDCl3) δ 7.86-7.83 (m, 2H), 7.36-7.33 (m, 2H), 7.29-7.23 (m, 2H), 6.97-6.94 (m, 1H), 4.70 (s, 2H), 4.33-4.29 (m, 1H), 4.21-4.17 (m, 1H), 2.01-1.99 (m, 1H), 1.69-1.65 (m, 1H), 1.34 (s, 3H), 0.91 (s, 3H). ESIMS m/z [M−H]$^-$ 373.1.

Example 33: 4-[(1S,3S)-2,2-dimethyl-3-{[(6-methylpyridin-3-yl)oxy]methyl}-cyclopropyl]benzenesulfonamide

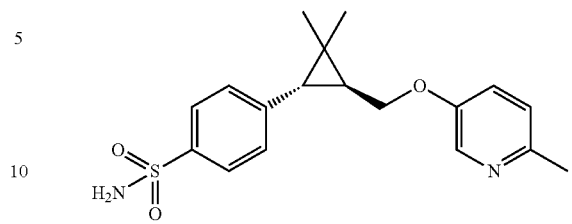

Example 33 was prepared from Intermediate V (120 mg, 0.47 mmol), 5-hydroxy-2-methylpyridine (62 mg, 0.56 mmol), TPP (136 mg, 0.52 mmol) and DIAD (0.10 mL, 0.52 mmol) in THF using General Procedure H. Purification by preparative TLC on silica, eluting with 60% EtOAc/DCM, followed by a second round of preparative TLC on silica, eluting with 5% MeOH/DCM, gave the title compound as a white solid. $^1$H NMR (500 MHz, CDCl3) δ 8.23-8.22 (m, 1H), 7.85-7.82 (m, 2H), 7.33-7.30 (m, 2H), 7.16-7.13 (m, 1H), 7.08-7.06 (m, 1H), 4.78 (s, 2H), 4.26-4.22 (m, 1H), 4.10-4.06 (m, 1H), 2.49 (s, 3H), 1.94 (d, 1H), 1.65 (q, 1H), 1.32 (s, 3H), 0.89 (s, 3H). ESIMS m/z [M−H]$^-$ 345.1.

Example 34: 4-[(1S,3S)-2,2-dimethyl-3-{[(2-methylpyridin-3-yl)oxy]methyl}-cyclopropyl]benzenesulfonamide

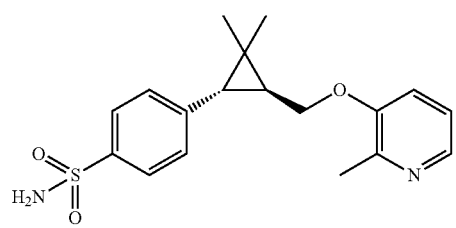 [SMILES: Cc1ncccc1OC[C@H]1[C@H](c2ccc(S(N)(=O)=O)cc2)C1(C)C]

Example 34 was prepared from Intermediate V (120 mg, 0.47 mmol), 3-hydroxy-2-methylpyridine (62 mg, 0.56 mmol), TPP (136 mg, 0.52 mmol) and DIAD (0.10 mL, 0.52 mmol) in THF using General Procedure H. Purification by successive rounds of preparative TLC on silica, eluting with 60% EtOAc/DCM, then 5% MeOH/DCM, gave the title compound as a white solid. $^1$H NMR (500 MHz, CDCl3) δ 8.10-8.08 (m, 1H), 7.85-7.82 (m, 2H), 7.34-7.31 (m, 2H), 7.10-7.07 (m, 2H), 4.70 (s, 2H), 4.24-4.20 (m, 1H), 4.09-4.05 (m, 1H), 2.49 (s, 3H), 1.97-1.95 (m, 1H), 1.68-1.65 (m, 1H), 1.32 (s, 3H), 0.90 (s, 3H). ESIMS m/z [M−H]$^-$ 345.1.

Example 35: 4-{(1R,3R)-3-[(4-fluoro-2-methylphenoxy)methyl]-2,2-dimethylcyclopropyl}benzenesulfonamide

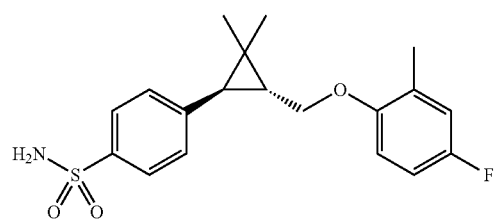 [SMILES: Cc1cc(F)ccc1OC[C@@H]1[C@@H](c2ccc(S(N)(=O)=O)cc2)C1(C)C]

Intermediate U (150 mg, 0.58 mmol) was reacted with 4-fluoro-2-methylphenol (100 mg, 0.79 mmol), TPP-PS (195 mg, 0.58 mmol), DIAD (119 mg, 0.58 mmol) as described under General Procedure N to furnish the title compound as white solid after preparative TLC (50% diethyl ether in hexane) purification, followed by trituration from 50% diethyl ether in hexane. $^1$H NMR (500 MHz, CDCl$_3$) δ 7.82 (d, 2H), 7.32 (d, 2H), 6.88-6.75 (m, 3H), 4.83 (s, 2H), 4.19-4.16 (m, 1H), 4.06-4.02 (m, 1H), 2.24 (s, 3H), 1.92 (d, 1H), 1.64 (q, 1H), 1.31 (s, 3H), 0.89 (s, 3H). ESIMS m/z [M−H]$^−$ 362.1.

Example 36: 4-{(1S,3S)-3-[(5-fluoro-2-methoxyphenoxy)methyl]-2,2-dimethylcyclopropyl}benzenesulfonamide

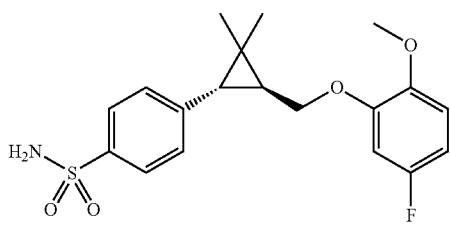 [SMILES: COc1ccc(F)cc1OC[C@H]1[C@H](c2ccc(S(N)(=O)=O)cc2)C1(C)C]

Intermediate V (150 mg, 0.58 mmol) was reacted with 5-fluoro-2-methoxyphenol (125 mg, 1.16 mmol), TPP-PS (195 mg, 0.58 mmol), DIAD (119 mg, 0.58 mmol) as described under General Procedure N to furnish the title compound as white solid after preparative TLC (70% diethyl ether in hexane) purification, followed by silica gel column chromatography (10% EtOAc in hexane). $^1$H NMR (500 MHz, CDCl$_3$) δ 7.82 (d, 2H), 7.31 (d, 2H), 6.83-6.80 (m, 1H), 6.71-6.60 (m, 2H), 4.76 (s, 2H), 4.25-4.22 (m, 1H), 4.15-4.12 (m, 1H), 3.83 (s, 3H), 1.92 (d, 1H), 1.69 (q, 1H), 1.31 (s, 3H), 0.88 (s, 3H). ESIMS m/z [M−H]$^−$ 378.1.

Example 37: 4-{(1R,2R)-2-[(2-cyano-4-fluorophenoxy)methyl]cyclopropyl}-benzenesulfonamide

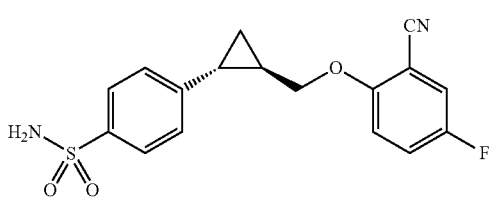 [SMILES: N#Cc1cc(F)ccc1OC[C@@H]1C[C@H]1c1ccc(S(N)(=O)=O)cc1]

Intermediate Y (150 mg, 0.66 mmol) was reacted with 5-fluoro-2-hydroxybenzonitrile (137 mg, 0.99 mmol), TPP-PS (221 mg, 0.66 mmol), DIAD (133 mg, 0.66 mmol) as described under General Procedure N to furnish the title compound as white solid after silica gel column chromatography (5%→20% EtOAc in hexane). $^1$H NMR (500 MHz, CDCl$_3$) δ 7.83 (d, 2H), 7.29-7.24 (m, 4H), 6.94-6.91 (m, 1H), 4.77 (s, 2H), 4.21-4.18 (m, 1H), 4.06-4.02 (m, 1H), 2.14-2.10 (m, 1H), 1.68-1.64 (m, 1H), 1.26-1.21 (m, 2H). ESIMS m/z [M−H]$^−$ 345.0.

Example 38: 4-[(1R,2R)-2-{[4-fluoro-2-(trifluoromethyl)phenoxy]methyl}-cyclopropyl]benzenesulfonamide

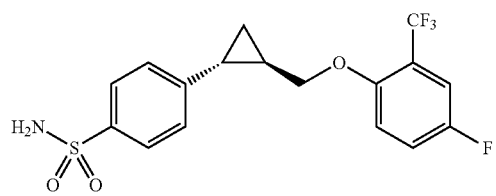

Intermediate Y (150 mg, 0.66 mmol) was reacted with 4-fluoro-2-trifluoromethylphenol (178 mg, 0.99 mmol), TPP-PS (221 mg, 0.66 mmol), DIAD (133 mg, 0.66 mmol) as described under General Procedure N to furnish the title compound as white solid after silica gel column chromatography (10%→30% EtOAc in DCM), followed by trituration from 50% diethyl ether in hexane. $^1$H NMR (500 MHz, CDCl$_3$) δ 7.82 (d, 2H), 7.32-7.17 (m, 4H), 6.95-6.93 (m, 1H), 4.75 (s, 2H), 4.22-4.20 (m, 1H), 4.01-3.97 (m, 1H), 2.12-2.09 (m, 1H), 1.64-1.58 (m, 1H), 1.24-1.17 (m, 2H). ESIMS m/z [M−H]$^−$ 388.0.

Example 39: 4-[(1R,2R)-2-{[(2,6-dimethoxypyridin-3-yl)oxy]methyl}cyclopropyl]-benzenesulfonamide

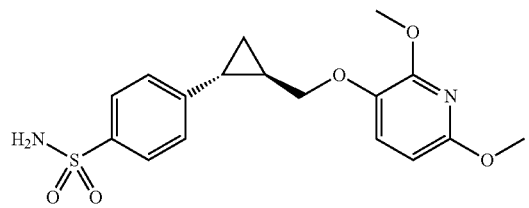 [SMILES: COc1ccc(OC[C@@H]2C[C@H]2c2ccc(S(N)(=O)=O)cc2)c(OC)n1]

Intermediate Y (200 mg, 0.88 mmol) was reacted with 2,6-dimethoxypyridin-3-ol (205 mg, 1.32 mmol), TPP-PS (292 mg, 0.88 mmol), DIAD (178 mg, 0.88 mmol) as described under General Procedure N to furnish the title compound as off-white solid after preparative TLC purification (70% diethyl ether in hexane), followed by silica gel column chromatography (10%→20% EtOAc in DCM). $^1$H NMR (500 MHz, CDCl$_3$) δ 7.80 (d, 2H), 7.16-7.13 (m, 3H), 6.19 (d, 1H), 4.79 (s, 2H), 4.01-3.91 (m, 5H), 3.87 (s, 3H), 1.97-1.93 (m, 1H), 1.66-1.62 (m, 1H), 1.15-1.10 (m, 2H). ESIMS m/z [M−H]$^−$ 363.0.

Example 40: 4-{(1R,2R)-2-[(5-chloro-2-methoxyphenoxy)methyl]cyclopropyl}-benzenesulfonamide

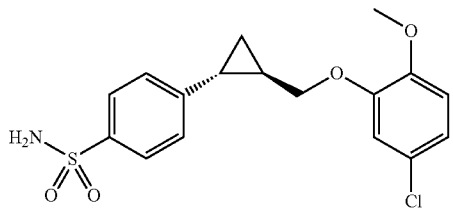 [SMILES: COc1ccc(Cl)cc1OC[C@@H]1C[C@H]1c1ccc(S(N)(=O)=O)cc1]

Intermediate Y (150 mg, 0.66 mmol) was reacted with 5-chloro-2-methoxyphenol (157 mg, 0.99 mmol), TPP-PS (221 mg, 0.66 mmol), DIAD (133 mg, 0.66 mmol) as described under General Procedure N to furnish the title compound as white solid after preparative TLC purification (70% diethyl ether in hexane), followed by silica gel column chromatography (10%→20% EtOAc in DCM). $^1$H NMR (500 MHz, CDCl$_3$) δ 7.80 (d, 2H), 7.16 (d, 2H), 6.84-6.81 (m, 1H), 6.64-6.54 (m, 2H), 4.78 (s, 2H), 4.04-4.02 (m, 1H), 3.99-3.95 (m, 1H), 3.81 (s, 3H), 1.99-1.96 (m, 1H), 1.70-1.66 (m, 1H), 1.17-1.13 (m, 2H). ESIMS m/z [M–H]$^-$ 366.0.

Example 41: 4-{(1R,2R)-2-[(4-fluoro-2-methoxy-phenoxy)methyl]cyclopropyl}-benzenesulfonamide

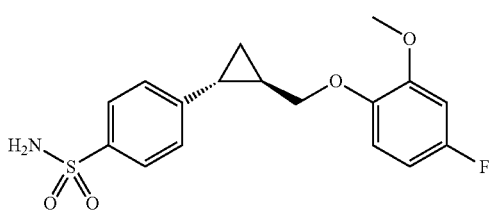 [SMILES: COc1cc(F)ccc1OC[C@@H]1C[C@H]1c1ccc(S(N)(=O)=O)cc1]

Intermediate Y (200 mg, 0.88 mmol) was reacted with 4-fluoro-2-methoxyphenol (188 mg, 1.32 mmol), TPP-PS (292 mg, 0.88 mmol), DIAD (178 mg, 0.88 mmol) as described under General Procedure N to furnish the title compound as white solid after silica gel column chromatography (30%→70% diethyl ether in hexane). $^1$H NMR (500 MHz, CDCl$_3$) δ 7.81 (d, 2H), 7.18 (d, 2H), 6.92-6.86 (m, 2H), 6.79 (d, 1H), 4.74 (s, 2H), 4.05-4.00 (m, 2H), 3.82 (s, 3H), 2.03-1.99 (m, 1H), 1.72-1.68 (m, 1H), 1.20-1.15 (m, 2H). ESIMS m/z [M–H]$^-$ 350.1.

Example 42: 4-[(1R,3R)-3-{[2-(difluoromethoxy)phenoxy]methyl}-2,2-dimethyl-cyclopropyl]benzenesulfonamide

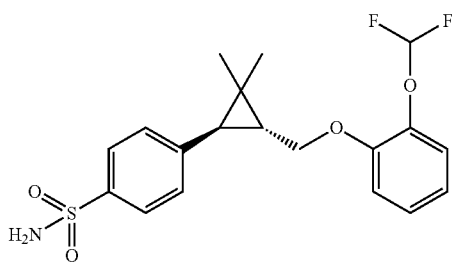 [SMILES: CC1(C)[C@H](COc2ccccc2OC(F)F)[C@H]1c1ccc(S(N)(=O)=O)cc1]

Example 42 was prepared from Intermediate U (150 mg, 0.59 mmol), 2-(difluoromethoxy)phenol (141 mg, 0.88 mmol), TPP-PS (196 mg, 0.59 mmol) and DIAD (0.12 mL, 0.59 mmol) in THF using General Procedure N. Purification by preparative TLC on silica, eluting with 60% Et$_2$O/pentane, followed by preparative TLC on silica, eluting with 10% EtOAc/DCM, gave the title compound as a white solid. $^1$H NMR (500 MHz, CDCl3) δ 7.84-7.83 (m, 2H), 7.33-7.32 (m, 2H), 7.20-7.17 (m, 2H), 7.02-7.00 (m, 1H), 6.97-6.94 (m, 1H), 6.57 (t, 1H), 4.75 (s, 2H), 4.29-4.26 (m, 1H), 4.16-4.12 (m, 1H), 1.95 (d, 1H), 1.67 (q, 1H), 1.31 (s, 3H), 0.89 (s, 3H). ESIMS m/z [M–H]$^-$ 396.1.

Example 43: 4-{(1R,3R)-3-[(5-fluoro-2-methoxyphenoxy)methyl]-2,2-dimethyl-cyclopropyl}benzenesulfonamide

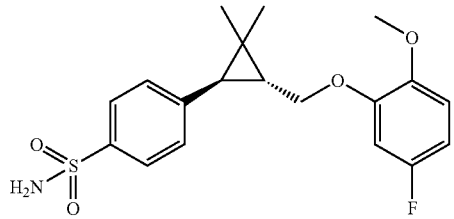 [SMILES: COc1ccc(F)cc1OC[C@@H]1[C@@H](c2ccc(S(N)(=O)=O)cc2)C1(C)C]

Example 43 was prepared from Intermediate U (150 mg, 0.59 mmol), 5-fluoro-2-methoxyphenol (125 mg, 0.88 mmol), TPP-PS (196 mg, 0.59 mmol) and DIAD (0.12 mL, 0.59 mmol) in THF using General Procedure N. Purification by two rounds of preparative TLC on silica, eluting with 60% Et$_2$O/pentane, gave the title compound as a white solid. $^1$H NMR (500 MHz, CDCl3) δ 7.83-7.82 (m, 2H), 7.32-7.30 (m, 2H), 6.83-6.80 (m, 1H), 6.71-6.68 (m, 1H), 6.64-6.60 (m, 1H), 4.71 (s, 2H), 4.25-4.21 (m, 1H), 4.15-4.11 (m, 1H), 3.83 (s, 3H), 1.94 (d, 1H), 1.69 (q, 1H), 1.31 (s, 3H), 0.88 (s, 3H). ESIMS m/z [M–H]$^-$ 378.1.

Example 44: 4-{(1S,2S)-2-[(4-fluoro-2-methoxyphenoxy)methyl]cyclopropyl}-benzenesulfonamide

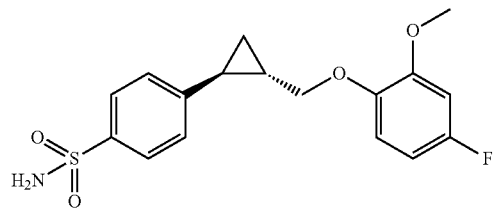 [SMILES: COc1cc(F)ccc1OC[C@H]1C[C@@H]1c1ccc(S(N)(=O)=O)cc1]

Example 44 was prepared from Intermediate AC (150 mg, 0.66 mmol), 4-fluoro-2-methoxyphenol (113 mg, 0.99 mmol), TPP-PS (220 mg, 0.66 mmol) and DIAD (0.13 mL, 0.66 mmol) in THF using General Procedure N. The crude material was first partially purified by preparative TLC on silica, eluting with 65% Et$_2$O/pentane. Further purification was achieved by flash chromatography on silica, eluting with 80% Et$_2$O/hexane, followed by recrystallization with Et$_2$O/hexane to give the title compound as a white solid. $^1$H NMR (500 MHz, CDCl$_3$) δ 7.8-7.78 (m, 2H), 7.18-7.16 (m, 2H), 6.84-6.81 (m, 1H), 6.64-6.62 (m, 1H), 6.58-6.54 (m, 1H), 4.71 (s, 2H), 4.06-4.02 (m, 1H), 3.99-3.96 (m, 1H), 3.81 (s, 3H), 1.99-1.96 (m, 1H), 1.70-1.66 (m, 1H), 1.17-1.14 (m, 2H). ESIMS m/z [M–H]$^-$ 350.1.

Example 45: 4-{(1S,2S)-2-[(2-cyano-4-fluorophenoxy)methyl]cyclopropyl}-benzenesulfonamide

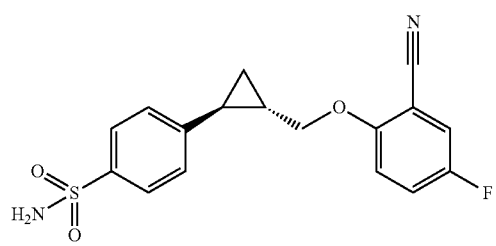 [SMILES: N#Cc1cc(F)ccc1OC[C@H]1C[C@@H]1c1ccc(S(N)(=O)=O)cc1]

Example 45 was prepared from Intermediate AC (150 mg, 0.66 mmol), 5-fluoro-2-hydroxybenzonitrile (136 mg, 0.99 mmol), TPP-PS (220 mg, 0.66 mmol) and DIAD (0.13 mL, 0.66 mmol) in THF using General Procedure N. The crude material was first partially purified by preparative TLC on silica, eluting with 65% Et2O/pentane. Further purification was achieved by flash chromatography on silica, eluting with 80% Et₂O/hexane, followed by recrystallization with Et₂O/hexane and a final round of preparative TLC on silica, eluting with 10% EtOAc/DCM to give the title compound as a white solid. ¹H NMR (500 MHz, CDCl₃) δ 7.84-7.82 (m, 2H), 7.30-7.21 (m, 4H), 6.94-6.91 (m, 1H), 4.73 (s, 2H), 4.21-4.18 (m, 1H), 4.05-4.02 (m, 1H), 2.14-2.10 (m, 1H), 1.68-1.64 (m, 1H), 1.26-1.21 (m, 2H). ESIMS m/z [M–H]⁻ 345.0.

Example 46: 4-[(1S,2S)-2-{[4-fluoro-2-(trifluoromethyl)phenoxy]methyl}cyclopropyl]-benzenesulfonamide

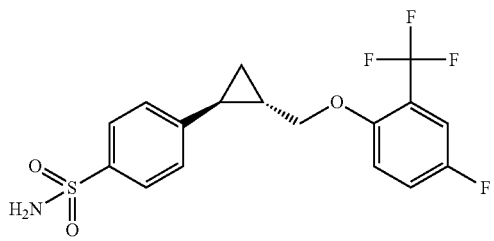 [SMILES: NS(=O)(=O)c1ccc([C@H]2C[C@@H]2COc2ccc(F)cc2C(F)(F)F)cc1]

Example 46 was prepared from Intermediate AC (150 mg, 0.66 mmol), 4-fluoro-2-(trifluoromethyl)phenol (178 mg, 0.99 mmol), TPP-PS (220 mg, 0.66 mmol) and DIAD (0.13 mL, 0.66 mmol) in THF using General Procedure N. The crude material was first partially purified by preparative TLC on silica, eluting with 65% Et₂O/pentane. Further purification was achieved by recrystallization from Et₂O/hexane to give the title compound as a white solid. ¹H NMR (500 MHz, DMSO-d₆) δ 7.74-7.72 (m, 2H), 7.5-7.52 (m, 2H), 7.37-7.28 (m, 5H), 4.28-4.25 (m, 1H), 4.16-4.13 (m, 1H), 2.15-2.11 (m, 1H), 1.67-1.61 (m, 1H), 1.20-1.17 (m, 2H). ESIMS m/z [M–H]⁻ 388.0.

Example 47: 4-{(1S,2S)-2-[(5-chloro-2-methoxyphenoxy)methyl]cyclopropyl}-benzenesulfonamide

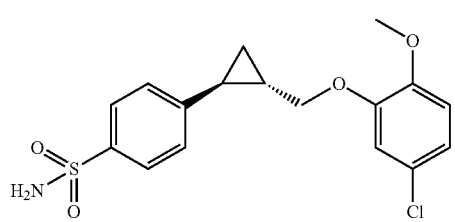 [SMILES: COc1ccc(Cl)cc1OC[C@H]1C[C@@H]1c1ccc(S(N)(=O)=O)cc1]

Example 47 was prepared from Intermediate AC (150 mg, 0.66 mmol), 5-chloro-2-methoxyphenol (157 mg, 0.99 mmol), TPP-PS (220 mg, 0.66 mmol) and DIAD (0.13 mL, 0.66 mmol) in THF using General Procedure N. The crude material was first partially purified by preparative TLC on silica, eluting with 70% Et₂O/pentane. Further purification was achieved by flash chromatography on silica, eluting with 80% Et2O/hexane, to give the title compound as a white solid. ¹H NMR (500 MHz, CDCl₃) δ 7.82-7.80 (m, 2H), 7.20-7.18 (m, 2H), 6.92-6.90 (m, 1H), 6.87-6.86 (m, 1H), 6.80-6.78 (m, 1H), 4.70 (s, 2H), 4.07-4.01 (m, 2H), 3.83 (s, 3H), 2.03-2.00 (m, 1H), 1.72-1.68 (m, 1H), 1.20-1.15 (m, 2H). ESIMS m/z [M–H]⁻ 366.0.

Example 48: 4-{(1R,3R)-3-[2-(2-methoxyphenyl)ethyl]-2,2-dimethylcyclopropyl}-benzenesulfonamide

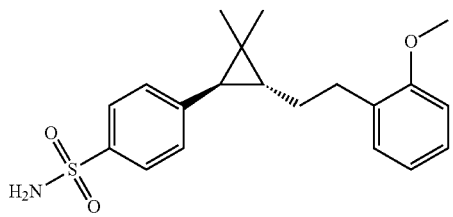 [SMILES: COc1ccccc1CC[C@@H]1[C@@H](c2ccc(S(N)(=O)=O)cc2)C1(C)C]

10% Pd over charcoal (40 mg) was added to a solution of Intermediate AI (80 mg, 0.20 mmol) in MeOH (10 mL) and stirred under atmosphere of hydrogen gas until complete (~24 h). Reaction mixture was filtered through celite plug and purified by silica gel chromatography (DCM) to furnish the title compound as colourless gum. ¹H NMR (500 MHz CDCl₃) δ 7.78 (d, 2H), 7.24 (d, 2H), 7.19-7.12 (m, 2H), 6.89-6.83 (m, 2H), 4.71 (s, 2H), 3.80 (s, 3H), 2.79-2.74 (m, 2H), 1.85-1.74 (m, 2H), 1.15 (s, 3H), 0.77 (s, 3H). ESIMS m/z [M–H]⁻ 358.1.

Example 49: 4-{(1R,2R)-2-[2-(5-chloro-2-methoxyphenyl)ethyl]spiro[2.4]hept-1-yl}benzenesulfonamide and Example 50: 4-{(1S,2S)-2-[2-(5-chloro-2-methoxyphenyl)ethyl]spiro[2.4]hept-1-yl}benzenesulfonamide Example 49

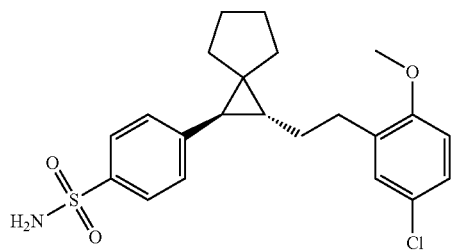

Example 50

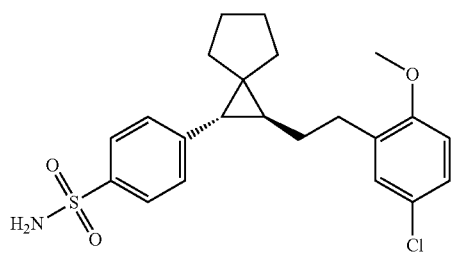

Racemic Example 4 was separated into constituent enantiomers using HPLC (Chiralpak AD-H, 20×250 mm, 5μ, n-Hexane/Ethanol 8:2, 10 mL/min), Example 49 was the first eluting isomer at Rt 11.05 min and Example 50 was second eluting isomer at Rt 12.67 min. The stereochemistry of separated enantiomers was arbitrarily assigned.

Example 51: 4-{(1S,2S)-2-[2-(5-chloro-2-methoxy-phenyl)ethyl]cyclopropyl}-benzenesulfonamide

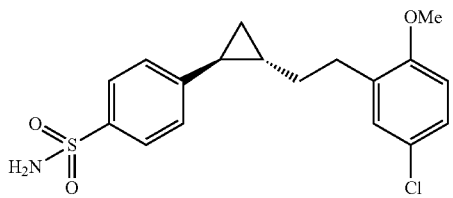 [SMILES: COc1ccc(Cl)cc1CC[C@H]1C[C@@H]1c1ccc(S(N)(=O)=O)cc1]

Intermediate BA (161 mg, 0.29 mmol) was reacted with PtO$_2$ (100 mg, 0.44 mmol), under the conditions described in General Procedure M. The crude material thus obtained was then treated with TFA (1 mL) as described in General Procedure R to give the title compound as a white solid. $^1$H NMR (500 MHz, CDCl3) δ 7.78-7.76 (m, 2H), 7.12-7.10 (m, 1H), 7.08-7.02 (m, 3H), 6.71-6.70 (m, 1H), 4.70 (s, 2H), 3.69 (s, 3H), 2.76-2.66 (m, 2H), 1.82-1.75 (m, 1H), 1.65-1.55 (m, 2H), 1.13-1.07 (m, 1H), 0.98-0.93 (m, 1H), 0.93-0.88 (m, 1H). ESIMS m/z [M−H]$^-$ 364.0.

Example 52: 4-{(1S,3S)-3-[2-(5-chloro-2-methoxy-phenyl)ethyl]-2,2-dimethyl-cyclopropyl}benzenesulfonamide

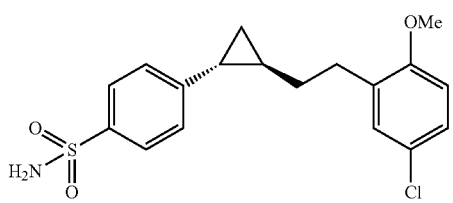 [SMILES: COc1ccc(Cl)cc1CC[C@@H]1C[C@H]1c1ccc(S(N)(=O)=O)cc1]

Intermediate BB (243 mg, 0.41 mmol) was treated with TFA (2.0 mL) under the conditions described in General Procedure R followed by treatment with PtO$_2$ (16 mg, 0.044 mmol) under the conditions described in General Procedure M to give the title compound as a colourless solid after purification by column chromatography (30% EtOAc/hexane) followed by preparative TLC (5% EtOAc/DCM). $^1$H NMR (500 MHz, CDCl3) δ 7.80-7.78 (m, 2H), 2.24-7.21 (m, 2H), 7.12-7.07 (m, 2H), 6.74 (d, 1H), 4.69 (s, 2H), 3.79 (s, 3H), 2.77-2.68 (m, 2H), 1.86-1.78 (m, 1H), 1.78-1.68 (m, 1H), 1.60-1.51 (m, 1H), 1.15-1.09 (m, 4H), 0.77 (s, 3H). ESIMS m/z [M−H]$^-$ 392.1.

Example 53: 4-{(1S,2R)-2-[(5-chloro-2-methoxy-phenoxy)methyl]cyclopropyl}-benzenesulfonamide

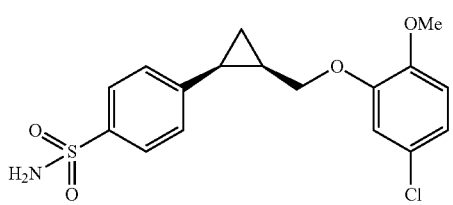 [SMILES: COc1ccc(Cl)cc1OC[C@@H]1C[C@@H]1c1ccc(S(N)(=O)=O)cc1]

Example 53 was prepared from Intermediate AA (150 mg, 0.66 mmol), 5-chloro-2-methoxyphenol (157 mg, 0.99 mmol), TPP-PS (220 mg, 0.66 mmol) and DIAD (0.13 mL, 0.66 mmol) in THF using General Procedure N. Purification by flash chromatography on silica, eluting with 80% Et$_2$O/pentane, followed by recrystallization from Et$_2$O, gave the title compound as a white solid. $^1$H NMR (500 MHz, CDCl$_3$) δ 7.82-7.81 (m, 2H), 7.20-7.18 (m, 2H), 6.92-6.90 (m, 1H), 6.88-6.85 (m, 1H), 6.80-6.78 (m, 1H), 4.70 (s, 2H), 4.07-3.99 (m, 2H), 3.83 (s, 3H), 2.03-2.00 (m, 1H), 1.72-1.69 (m, 1H), 1.20-1.16 (m, 2H). ESIMS m/z [M−H]$^-$ 366.0.

Example 54: 4-{(1R,3R)-3-[2-(5-chloro-2-methoxy-phenyl)ethyl]-2,2-dimethyl-cyclopropyl}benzenesulfonamide

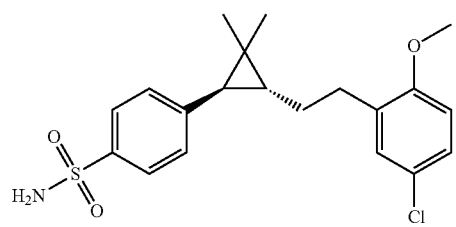 [SMILES: COc1ccc(Cl)cc1CC[C@@H]1[C@@H](c2ccc(S(N)(=O)=O)cc2)C1(C)C]

Intermediate AI (180 mg, 0.50 mmol) was hydrogenated as described in General Procedure M and crude was purified by silica gel chromatography (DCM) to furnish the title compound as colourless gum. $^1$H NMR (500 MHz CDCl$_3$) δ 7.80 (d, 2H), 7.24 (d, 2H), 7.24-7.23 (d, 2H), 7.13-7.09 (m, 2H), 6.75 (d, 1H), 4.76 (s, 2H), 3.80 (s, 3H), 2.76-2.70 (m, 2H), 1.85-1.72 (m, 2H), 1.60-1.51 (m, 1H), 1.15-1.10 (s, 4H), 0.78 (s, 3H). ESIMS m/z [M−H]$^-$ 392.1.

Example 55: 4-[(1R,3R)-3-{[(5-chloropyridin-2-yl)oxy]methyl}-2,2-dimethyl-cyclopropyl]benzenesulfonamide

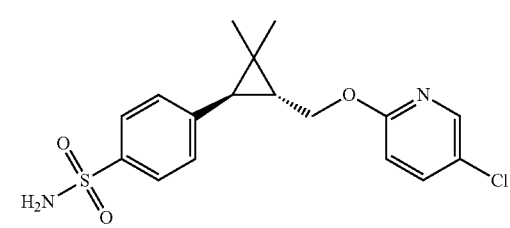 [SMILES: CC1(C)[C@H](COc2ccc(Cl)cn2)[C@H]1c1ccc(S(N)(=O)=O)cc1]

Example 55 was prepared from Intermediate BE (134 mg, 0.24 mmol) under the conditions described in General Procedure R. Purification by silica gel column chromatography (0%→50% EtOAc in hexane) gave the title compound as a white solid. $^1$H NMR (500 MHz, CDCl$_3$) δ 8.09 (d, 1H), 7.83 (d, 2H), 7.53 (dd 1H), 7.31 (d, 2H), 6.72 (d, 1H), 4.85 (s, 2H), 4.53-4.49 (m, 1H), 4.39-4.35 (m, 1H), 1.93 (d, 1H), 1.69-1.65 (m, 1H), 1.32 (s, 3H), 0.87 (s, 3H). ESIMS m/z [M+H]$^+$ 367.1.

Example 56: 4-[(1S,3S)-2,2-dimethyl-3-{[(2-methylpyrimidin-5-yl)oxy]methyl}-cyclopropyl]benzenesulfonamide

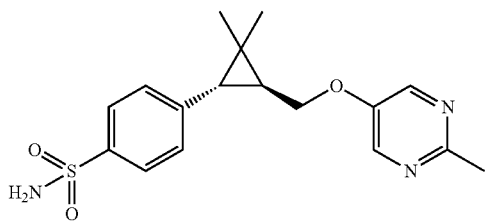 [SMILES: Cc1ncc(OC[C@H]2[C@H](c3ccc(S(N)(=O)=O)cc3)C2(C)C)cn1]

Example 56 was prepared from Intermediate BC under the conditions described in General Procedure R. Purification by recrystallization from Et$_2$O gave the title compound as a white solid. $^1$H NMR (500 MHz, CDCl$_3$) δ 8.35 (s, 2H), 7.86-7.84 (m, 2H), 7.33-7.31 (m, 2H), 4.78 (s, 2H), 4.32-4.28 (m, 1H), 4.15-4.11 (m, 1H), 2.68 (s, 3H), 1.98-1.97 (m, 1H), 1.68-1.64 (m, 1H), 1.33 (s, 3H), 0.90 (s, 3H). ESIMS m/z [M–H]$^-$ 346.1

Example 57: 4-{(1S,3S)-2,2-dimethyl-3-[(pyrimidin-5-yloxy)methyl]cyclopropyl}-benzenesulfonamide

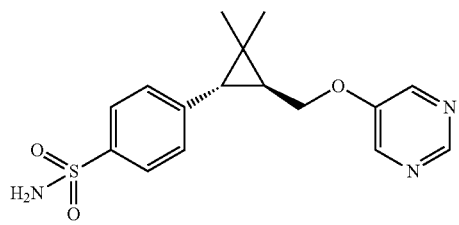 [SMILES: CC1(C)[C@@H](COc2cncnc2)[C@@H]1c1ccc(S(N)(=O)=O)cc1]

Example 57 was prepared from Intermediate BD under the conditions described in General Procedure R. Purification by recrystallization from Et$_2$O gave the title compound as a white solid. $^1$H NMR (500 MHz, CDCl$_3$) δ 8.88 (s, 1H) 8.46 (s, 2H), 7.87-7.86 (m, 2H), 7.34-7.33 (m, 2H), 4.81 (s, 2H), 4.37-4.33 (m, 1H), 4.21-4.17 (m, 1H), 1.99 (d, 1H), 1.71-1.67 (m, 1H), 1.35 (s, 3H), 0.92 (s, 3H). ESIMS m/z [M–H]$^-$ 332.0.

Example 58: 4-{(1S,2R)-2-[(2-cyano-4-fluorophenoxy)methyl]cyclopropyl}-benzenesulfonamide

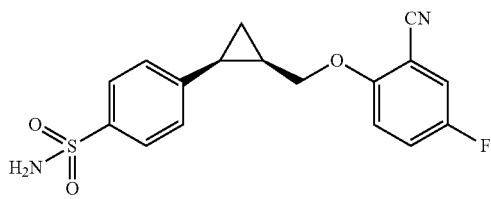 [SMILES: N#Cc1cc(F)ccc1OC[C@@H]1C[C@@H]1c1ccc(S(N)(=O)=O)cc1]

Example 58 was prepared from Intermediate AA (150 mg, 0.66 mmol), 5-fluoro-2-hydroxybenzonitrile (136 mg, 0.99 mmol), TPP-PS (220 mg, 0.66 mmol) and DIAD (0.13 mL, 0.66 mmol) in THF using General Procedure N. Purification by flash chromatography on silica, eluting with 80% Et$_2$O/n-hexane, followed by recrystallization from Et$_2$O, gave the title compound as a white solid. $^1$H NMR (500 MHz, CDCl$_3$) δ 7.84-7.82 (m, 2H), 7.30-7.22 (m, 4H), 6.93-6.91 (m, 1H), 4.70 (s, 2H), 4.21-4.18 (m, 1H), 4.05-4.02 (m, 1H), 2.14-2.10 (m, 1H), 1.68-1.65 (m, 1H), 1.26-1.24 (m, 2H). ESIMS m/z [M–H]$^-$ 345.0.

Evaluation of Modulators of α7 nAChRs Using the IonFlux$^{HT}$ Automated Patch Clamp System Compound Preparation:

Acetylcholine was freshly prepared for each plate run and used at an EC$_{20}$ concentration (approximately 60 μM for rat α7/CHO) to induce α7 nAChR currents on the IonFlux$^{HT}$. To prepare the ACh solution for a single plate, 6 μl of the 100 mM ACh stock was diluted into 10 ml of 0.3% DMSO/external solution Test compounds were prepared for a 6-point dose response from 0.03-10 μM. Working stocks were prepared from serial dilutions of 10 mM DMSO stock solutions to give a final DMSO concentration of 0.3%. 80 μl of the final concentration of each compound was added to the appropriate wells in an IonFlux$^{HT}$ assay plate.

Cell Preparation:

2×T175 flasks of α7/CHO cells (~60-70% confluent) were washed twice with PBS and trypsinized (2 ml) for 3.5 minutes at 37° C./5% CO$_2$. Cells were collected in F-12K complete media, counted and the number required for the assay was calculated, for example, 2×10$^6$ cells in a final volume of 670 μl of external solution were required to load one zone (one quarter) of an IonFlux$^{HT}$ assay plate. The correct number of cells was pelleted by centrifuge, the supernatant was discarded and the cell pellet was resuspend in external solution at the required concentration so that cells were added in a volume of 80 μl per well to the IonFlux$^{HT}$ assay plate.

Calculation of the Effect of Compounds on ACh Mediated Currents in α7 nAChRs:

The effect of test compounds on EC$_{20}$ ACh-evoked currents was calculated by the formula:

$$\text{Potentiation (\%)} = \left(\frac{\text{average peak ACh } EC20 + PAM}{\text{average peak ACh } EC20} - 1\right) * 100$$

IonFlux™ Assay

The rinse protocol was the initial step in preparation of the IonFlux$^{HT}$ plate. 80 μl of MilliQ water was added to every well (except Out wells) and the IonFlux$^{HT}$ assay plate was run through the water rinse protocol on the machine. At the end of the run, the water was discarded from the wells. This action was repeated twice.

Briefly, to prepare the plate for the assay aliquots of cells, compounds and internal and external solutions were added to wells of the prepared IonFlux$^{HT}$ plate (80 μl/well) (solutions made to manufacturer's specifications). Automated whole cell patch-clamp recordings were made using the standard IonFlux$^{HT}$ single application protocol. Vacuum was held at 6 psi/hg throughout the experiment and membrane potential was held at −80 mV for 35 sec and then at −60 mV during data acquisition. Two ACh (EC$_{20}$) pulses were applied at the beginning of the assay, 90 seconds apart, to provide an ACh baseline response then cells were perfused with modulators for 89 sec before ACh (EC$_{20}$) was applied for 1 s. The calculation of percent potentiation of the acetylcholine response for each well was performed by the data analysis software supplied with the IonFlux$^{HT}$. This data was then entered into GraphPad Prism to determine $EC_{50}$ values from fitted curves.

The following compounds were tested in accordance with the above-procedure for activity and the $EC_{50}$ values determined are reported:

Exp. 1: $Ec_{50}$ (nM)=105; Exp. 2: $Ec_{50}$ (nM)=143; Exp. 4: $Ec_{50}$ (nM)=48; Exp. 5: $Ec_{50}$ (nM)=193; Exp. 6: $Ec_{50}$ (nM)=596; Exp. 7: $Ec_{50}$ (nM)=1047; Exp. 8: $Ec_{50}$ (nM)=517; Exp. 9: $Ec_{50}$ (nM)=1750; Exp. 10: $Ec_{50}$ (nM)=429; Exp. 11: $Ec_{50}$ (nM)=3641; Exp. 12: $Ec_{50}$ (nM)=1347; Exp. 13: $Ec_{50}$ (nM)=70; Exp. 14: $Ec_{50}$ (nM)=452; Exp. 15: $Ec_{50}$ (nM)=75; Exp. 16: $Ec_{50}$ (nM)=125; Exp. 17: $Ec_{50}$ (nM)=4357; Exp. 18: $Ec_{50}$ (nM)=2295; Exp. 19: $Ec_{50}$ (nM)=350; Exp. 20: $Ec_{50}$ (nM)=3305; Exp. 21: $Ec_{50}$ (nM)=3877; Exp. 22: $Ec_{50}$ (nM)=743; Exp. 23: $Ec_{50}$ (nM)=546; Exp. 24: $Ec_{50}$ (nM)=906; Exp. 25: $Ec_{50}$ (nM)=4165; Exp. 26: $Ec_{50}$ (nM)=606; Exp. 27: $Ec_{50}$ (nM)=3972; Exp. 28: $Ec_{50}$ (nM)=3102; Exp. 29: $Ec_{50}$ (nM)=1245; Exp. 30: $Ec_{50}$ (nM)=2520; Exp. 31: $Ec_{50}$ (nM)=200; Exp. 32: $Ec_{50}$ (nM)=811; Exp. 33: $Ec_{50}$ (nM)=546; Exp. 34: $Ec_{50}$ (nM)=1616; Exp. 35: $Ec_{50}$ (nM)=395; Exp. 36: $Ec_{50}$ (nM)=164; Exp. 37: $Ec_{50}$ (nM)=6004; Exp. 38: $Ec_{50}$ (nM)=1136; Exp. 39: $Ec_{50}$ (nM)=5365; Exp. 40: $Ec_{50}$ (nM)=1065; Exp. 41: $Ec_{50}$ (nM)=2592; Exp. 42: $Ec_{50}$ (nM)=625; Exp. 43: $Ec_{50}$ (nM)=1561; Exp. 44: $Ec_{50}$ (nM)=2942; Exp. 45: $Ec_{50}$ (nM)=2505; Exp. 46: $Ec_{50}$ (nM)=701; Exp. 47: $Ec_{50}$ (nM)=3699; Exp. 48: $Ec_{50}$ (nM)=612; Exp. 49: $Ec_{50}$ (nM)=64; Exp. 50: $Ec_{50}$ (nM)=190; Exp. 51: $Ec_{50}$ (nM)=626; Exp. 52: $Ec_{50}$ (nM)=54; Exp. 53: $Ec_{50}$ (nM)=2195; Exp. 54: $Ec_{50}$ (nM)=124; Exp. 55: $Ec_{50}$ (nM)=1470; Exp. 56: $Ec_{50}$ (nM)>10000; Exp. 57: $Ec_{50}$ (nM)>10000; Exp. 58: $Ec_{50}$ (nM)>10000

What is claimed is:

1. A compound of Formula IVA:

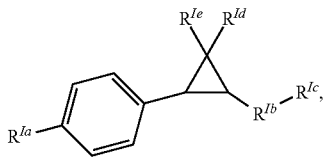

Formula IVA or a salt thereof,
wherein:
  $R^{Ia}$ is a moiety of the formula: (a) $NH_2$—$SO_2$—; (b) $NR'_2$—$SO_2NR''$—, wherein R' is independently for each occurrence: (i) —H; (ii) linear-, branched-, or cyclic-alkyl of up to 6 carbon atoms; or (iii) one of R' is —H and the other is t-BOC; and R" is: (a) —H; or (b) linear-, branched-, or cyclic-alkyl of up to 6 carbon atoms; or (iv) one of R' is —H and the other R' together with R" and the —N—$SO_2$—N— moiety to which they are attached form a heterocycle of up to 6 ring atoms;
  $R^{Ib}$ has the formula: —$CH_2$—X—, wherein X is —O—, —S—, $CH_2$—;
  $R^{Id}$ and $R^{Ie}$ are independently for each occurrence —H or linear-, branched-, or cyclic-alkyl of up to 6 carbon atoms; or
  $R^{Id}$ and $R^{Ie}$ together with the cyclopropyl moiety to which they are attached from a spirocycle of up to 8 carbon atoms;

$R^{Ic}$ is:
  (a) a heteroaryl of the formula:

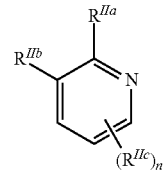

wherein:
    n=0, 1, or 2;
    one of $R^{IIa}$ or $R^{IIb}$ is a bond to the cyclopropyl core of Formula IVA and the other is —H or —$R^{IIc}$, wherein,
      $R^{IIc}$ is: (i) linear-, branched-, or cyclic-alkoxy of up to 6 carbon, which may optionally be substituted with one or more halogen; (ii) linear-, branched-, or cyclic-alkyl of up to 6 carbon atoms, which may optionally be substituted with halogen or linear-, branched-, or cyclic-alkoxy of up to 6 carbon atoms;
  (b) heteroaryl of the formula

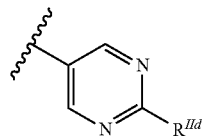

wherein:
    $R^{IId}$ is —H or linear-, branched-, or cyclic-alkyl of up to 6 carbon atoms; or
  (c) aryl of the formula

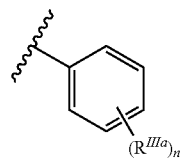

wherein:
    n=1 or 2;
    $R^{IIIa}$ is: (i) halogen; (ii) —CN; (iii) linear-, branched-, or cyclic-alkoxy of up to 6 carbon atoms which may optionally be substituted with one or more (1) halogen; or (2) linear-, branched-, or cyclic alkoxy of up to 6 carbon atoms; (iv) linear-, branched-, or cyclic-alkyl of up to 6 carbon atoms which may optionally be substituted with one or more: (1) halogen; or (2) linear-, branched-, or cyclic alkoxy of up to 6 carbon atoms.

2. A compound of claim 1, or a salt thereof, wherein, $R^{Id}$ and $R^{Ie}$ are independently for each occurrence: (a) —H, or (b) methyl.

3. A compound of claim 2, or a salt thereof, wherein $R^{Id}$ and $R^{Ie}$ are joined together to form, together with the cyclopropyl moiety to which they are attached, a spirocyclo moiety of 7 carbon atoms.

4. A compound, or a salt thereof, of claim 1 wherein, —R$^{Ib}$-R$^{Ic}$ is —CH$_2$—X—R$^{AH}$, wherein:

X is —CH$_2$—, —S—, or —O—; and

R$^{AH}$ is:

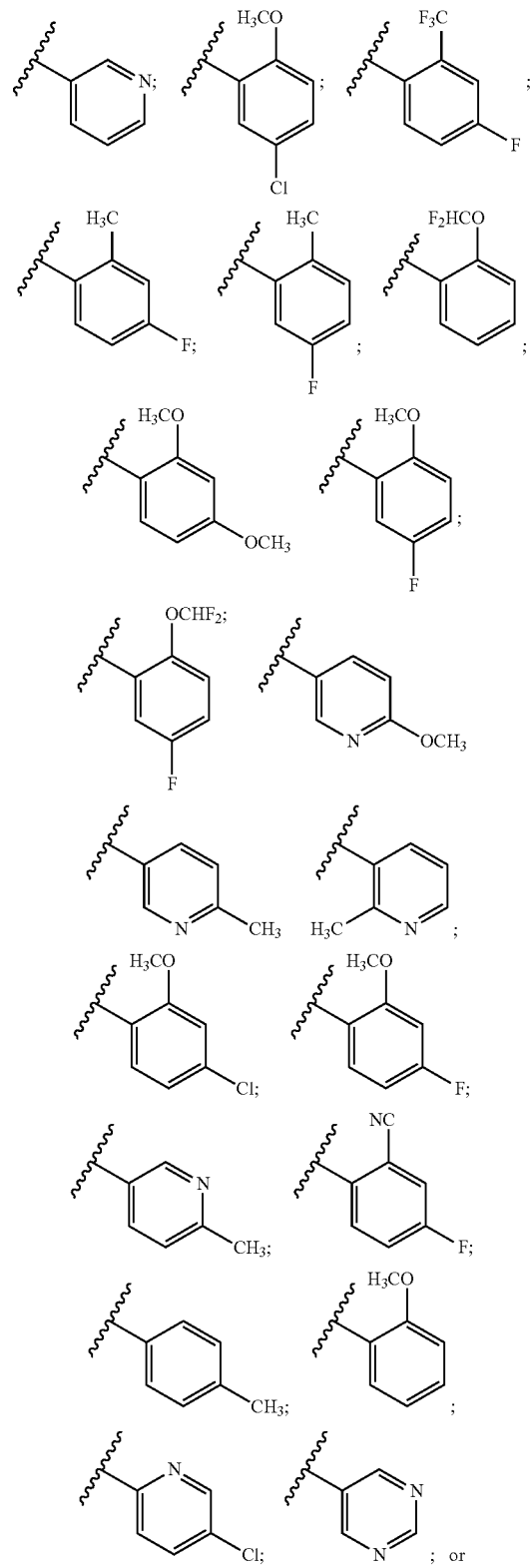

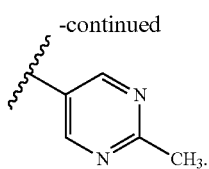

5. A compound which is:
- ±trans 4-{3-[(5-chloro-2-methoxyphenoxy)methyl]-2,2-dimethylcyclopropyl}benzene-sulfonamide;
- ±trans 4-{2-[(5-chloro-2-methoxyphenoxy)methyl]spiro[2.4]hept-1-yl}benzenesulfonamide;
- ±trans 4-[(1R,3R)-3-{[4-fluoro-2-(trifluoromethyl)phenoxy]methyl}-2,2-dimethylcyclopropyl]-benzene sulfonamide;
- ±trans 4-{(1R,2R)-2-[2-(5-chloro-2-methoxyphenyl)ethyl]spiro[2.4]hept-1-yl}benzene-sulfonamide;
- N-(4-{(1S,3S)-3-[(5-chloro-2-methoxyphenoxy)methyl]-2,2-dimethylcyclopropyl}phenyl)-methanesulfonamide;
- N-{4-[(1S,3S)-3-{[(6-methoxypyridin-3-yl)oxy]methyl}-2,2-dimethylcyclopropyl]phenyl}-methanesulfonamide;
- N-(4-{(1S,3S)-3-[(4-fluoro-2-methylphenoxy)methyl]-2,2-dimethylcyclopropyl}phenyl)-methanesulfonamide;
- N-(4-{(1S,3S)-3-[(4-fluoro-2-methylphenoxy)methyl]-2,2-dimethylcyclopropyl}phenyl) sulfuric diamide;
- N-(4-{(1S,3S)-3-[(5-fluoro-2-methylphenoxy)methyl]-2,2-dimethylcyclopropyl}phenyl) sulfuric diamide;
- 4-[(1S,3S)-3-{[4-fluoro-2-(trifluoromethyl)phenoxy]methyl}-2,2-dimethylcyclopropyl]benzene-sulfonamide;
- 4-{(1S,3S)-3-[(5-chloro-2-methoxyphenoxy)methyl]-2,2-dimethylcyclopropyl}benzene-sulfonamide;
- 4-{(1R,3R)-3-[(5-chloro-2-methoxyphenoxy)methyl]-2,2-dimethylcyclopropyl}benzene-sulfonamide;
- 4-[(1S,3S)-2,2-dimethyl-3-{[(4-methylphenyl)sulfanyl]methyl}cyclopropyl]benzene-sulfonamide;
- 4-[(1R,3R)-3-{[(5-chloro-2-methoxyphenyl)sulfanyl]methyl}-2,2-dimethylcyclopropyl]benzene-sulfonamide;
- 4-[(1R,3R)-2,2-dimethyl-3-{[(4-methylphenyl)sulfanyl]methyl}cyclopropyl]benzene-sulfonamide;
- 4-[(1S,3S)-3-{[(5-chloro-2-methoxyphenyl)sulfanyl]methyl}-2,2-dimethylcyclopropyl]benzene-sulfonamide;
- N-{4-[(1S,3S)-3-{[(6-methoxypyridin-3-yl)oxy]methyl}-2,2-dimethylcyclopropyl]phenyl}-sulfuric diamide;
- N-{4-[(1S,3S)-2,2-dimethyl-3-{[(6-methylpyridin-3-yl)oxy]methyl}cyclopropyl]phenyl}sulfuric diamide;
- N-{4-[(1S,3S)-2,2-dimethyl-3-{[(2-methylpyridin-3-yl)oxy]methyl}cyclopropyl]phenyl}-methanesulfonamide;
- N-{4-[(1S,3S)-2,2-dimethyl-3-{[(2-methylpyridin-3-yl)oxy]methyl}cyclopropyl]phenyl}sulfuric diamide;
- 4-[(1R,3R)-3-{[(2,6-dimethoxypyridin-3-yl)oxy]methyl}-2,2-dimethylcyclopropyl]benzene-sulfonamide;
- 4-[(1R,3R)-3-{[2-(difluoromethoxy)-5-fluorophenoxy]methyl}-2,2-dimethylcyclopropyl]-benzenesulfonamide;
- N-(4-{(1S,3S)-3-[(4-chloro-2-methoxyphenoxy)methyl]-2,2-dimethylcyclopropyl}phenyl)-sulfuric diamide;
- N-(4-{(1S,3S)-3-[(4-fluoro-2-methoxyphenoxy)methyl]-2,2-dimethylcyclopropyl}phenyl)-sulfuric diamide;

4-{(1S,3S)-2,2-dimethyl-3-[(pyridin-3-yloxy)methyl]
cyclopropyl}benzenesulfonamide;
4-[(1S,3S)-3-{[(2,6-dimethoxypyridin-3-yl)oxy]methyl}-
2,2-dimethylcyclopropyl]-benzenesulfonamide;
4-[(1R,3R)-2,2-dimethyl-3-{[(6-methylpyridin-3-yl)oxy]
methyl}cyclopropyl]benzene-sulfonamide;
4-{(1R,3R)-3-[(2-cyano-4-fluorophenoxy)methyl]-2,2-
dimethylcyclopropyl}benzene-sulfonamide;
4-{(1R,3R)-3-[(4-fluoro-2-methoxyphenoxy)methyl]-2,
2-dimethylcyclopropyl}benzene-sulfonamide;
4-{(1S,3S)-3-[(4-fluoro-2-methoxyphenoxy)methyl]-2,2-
dimethylcyclopropyl}benzene-sulfonamide;
4-{(1S,3S)-3-[(4-fluoro-2-methylphenoxy)methyl]-2,2-
dimethylcyclopropyl}benzene-sulfonamide;
4-{(1S,3S)-3-[(2-cyano-4-fluorophenoxy)methyl]-2,2-
dimethylcyclopropyl}benzene-sulfonamide;
4-[(1S,3S)-2,2-dimethyl-3-{[(6-methylpyridin-3-yl)oxy]
methyl}cyclopropyl]benzene-sulfonamide;
4-[(1S,3S)-2,2-dimethyl-3-{[(2-methylpyridin-3-yl)oxy]
methyl}cyclopropyl]benzene-sulfonamide;
4-{(1R,3R)-3-[(4-fluoro-2-methylphenoxy)methyl]-2,2-
dimethylcyclopropyl}benzene-sulfonamide;
4-{(1S,3S)-3-[(5-fluoro-2-methoxyphenoxy)methyl]-2,2-
dimethylcyclopropyl}benzene-sulfonamide;
4-{(1R,2R)-2-[(2-cyano-4-fluorophenoxy)methyl]
cyclopropyl}benzenesulfonamide;
4-[(1R,2R)-2-{[4-fluoro-2-(trifluoromethyl)phenoxy]
methyl}cyclopropyl]benzenesulfonamide;
4-[(1R,2R)-2-{[(2,6-dimethoxypyridin-3-yl)oxy]
methyl}cyclopropyl]benzenesulfonamide;
4-{(1R,2R)-2-[(5-chloro-2-methoxyphenoxy)methyl]
cyclopropyl}benzenesulfonamide;
4-{(1R,2R)-2-[(4-fluoro-2-methoxyphenoxy)methyl]
cyclopropyl}benzenesulfonamide;
4-[(1R,3R)-3-{[2-(difluoromethoxy)phenoxy]methyl}-2,
2-dimethylcyclopropyl]benzene-sulfonamide;
4-{(1R,3R)-3-[(5-fluoro-2-methoxyphenoxy)methyl]-2,
2-dimethylcyclopropyl}benzene-sulfonamide;
4-{(1S,2S)-2-[(4-fluoro-2-methoxyphenoxy)methyl]
cyclopropyl}benzenesulfonamide;
4-{(1S,2S)-2-[(2-cyano-4-fluorophenoxy)methyl]
cyclopropyl}benzenesulfonamide;
4-[(1S,2S)-2-{[4-fluoro-2-(trifluoromethyl)phenoxy]
methyl}cyclopropyl]benzene sulfonamide;
4-{(1S,2S)-2-[(5-chloro-2-methoxyphenoxy)methyl]
cyclopropyl}benzenesulfonamide;
4-{(1R,3R)-3-[2-(2-methoxyphenyl)ethyl]-2,2-
dimethylcyclopropyl}benzenesulfonamide;
4-{(1R,2R)-2-[2-(5-chloro-2-methoxyphenyl)ethyl]spiro
[2.4]hept-1-yl}benzenesulfonamide;
4-{(1S,2S)-2-[2-(5-chloro-2-methoxyphenyl)ethyl]spiro
[2.4]hept-1-yl}benzenesulfonamide;
4-{(1S,2S)-2-[2-(5-chloro-2-methoxyphenyl)ethyl]
cyclopropyl}benzenesulfonamide;
4-{(1S,3S)-3-[2-(5-chloro-2-methoxyphenyl)ethyl]-2,2
dimethylcyclopropyl}benzene-sulfonamide;
4-{(1S,2R)-2-[(5-chloro-2-methoxyphenoxy)methyl]
cyclopropyl}benzenesulfonamide;
4-{(1R,3R)-3-[2-(5-chloro-2-methoxyphenyl)ethyl]-2,2-
dimethylcyclopropyl}benzene-sulfonamide; or
4-[(1R,3R)-3-{[(5-chloropyridin-2-yl)oxy]methyl}-2,2-
dimethylcyclopropyl]benzene-sulfonamide;
4-[(1S,3S)-2,2-dimethyl-3-{[(2-methylpyrimidin-5-yl)
oxy]methyl}cyclopropyl]benzene-sulfonamide;
4-{(1S,3S)-2,2-dimethyl-3-[(pyrimidin-5-yloxy)methyl]
cyclopropyl}benzenesulfonamide; or
4-{(1S,2R)-2-[(2-cyano-4-fluorophenoxy)methyl]
cyclopropyl}benzenesulfonamide;
or a pharmaceutically acceptable salt of any of the foregoing.

6. A pharmaceutical formulation comprising at least one compound of claim 1 and at least one excipient.

7. A method of treating Alzheimer's disease (AD), schizophrenia, or Parkinson's disease (PD) comprising administering to a patient in need thereof a therapeutically effective amount of a pharmaceutical formulation of claim 6.

\* \* \* \* \*